US012291717B2

(12) United States Patent
Poleganov et al.

(10) Patent No.: US 12,291,717 B2
(45) Date of Patent: May 6, 2025

(54) RNA REPLICON FOR REPROGRAMMING SOMATIC CELLS

(71) Applicants: BIONTECH RNA PHARMACEUTICALS GMBH, Mainz (DE); TRON-TRANSLATIONALE ONKOLOGIE AN DER UNIVERSITÄTSMEDIZIN DER JOHANNES GUTENBERG-UNIVERSITAT MAINZ GEMEIN-NUTZIGE GMBH, Mainz (DE)

(72) Inventors: Marco Alexander Poleganov, Mainz (DE); Mario Perkovic, Mainz (DE); Ugur Sahin, Mainz (DE); Tim Beissert, Mainz (DE)

(73) Assignees: BIONTECH RNA PHARMACEUTICALS GMBH, Mainz (DE); TRON-Translationale Onkologie An Der Universitätsmedizin Der Johannes Gutenberg-Universität Mainz Gemeinnützige GMBH, Mainz (DE)

( * ) Notice: Subject to any disclaimer, the term of this patent is extended or adjusted under 35 U.S.C. 154(b) by 690 days.

(21) Appl. No.: 16/645,707

(22) PCT Filed: Sep. 11, 2018

(86) PCT No.: PCT/EP2018/074486
§ 371 (c)(1),
(2) Date: Mar. 9, 2020

(87) PCT Pub. No.: WO2019/053012
PCT Pub. Date: Mar. 21, 2019

(65) Prior Publication Data
US 2020/0277627 A1 Sep. 3, 2020

(30) Foreign Application Priority Data

Sep. 13, 2017 (WO) ................ PCT/EP2017/073063

(51) Int. Cl.
*C12N 15/86* (2006.01)
*C12N 5/074* (2010.01)

(52) U.S. Cl.
CPC ........... *C12N 15/86* (2013.01); *C12N 5/0696* (2013.01); *C12N 2501/602* (2013.01); *C12N 2501/603* (2013.01); *C12N 2501/604* (2013.01); *C12N 2501/605* (2013.01); *C12N 2501/606* (2013.01); *C12N 2501/608* (2013.01); *C12N 2506/1307* (2013.01); *C12N 2770/36143* (2013.01)

(58) Field of Classification Search
None
See application file for complete search history.

(56) References Cited

U.S. PATENT DOCUMENTS

| | | | | |
|---|---|---|---|---|
| 2009/0075384 A1* | 3/2009 | Kamrud | ................ | A61P 37/04 435/235.1 |
| 2015/0159143 A1* | 6/2015 | Dowdy | ................ | C12N 9/127 435/7.1 |
| 2017/0037376 A1 | 2/2017 | Pei et al. | | |

FOREIGN PATENT DOCUMENTS

| | | |
|---|---|---|
| CN | 104630136 | 5/2015 |
| CN | 105407922 | 3/2016 |
| CN | 105829525 | 8/2016 |
| JP | 2015-519898 | 7/2015 |
| WO | 2008/119827 | 10/2008 |
| WO | 2013/177133 | 11/2013 |
| WO | 2015014870 | 2/2015 |
| WO | 2015049342 | 4/2015 |
| WO | 2017/087763 | 5/2017 |
| WO | 2017/162265 | 9/2017 |
| WO | 2017162266 | 9/2017 |

OTHER PUBLICATIONS

Yoshioka, N., & Dowdy, S. F. (2017). Enhanced generation of iPSCs from older adult human cells by a synthetic five-factor self-replicative RNA. PLoS One, 12(7), e0182018. (Year: 2017).*
Yoshioka, N., Gros, E., Li, H. R., Kumar, S., Deacon, D. C., Maron, C., . . . & Dowdy, S. F. (2013). Efficient generation of human iPSCs by a synthetic self-replicative RNA. Cell stem cell, 13(2), 246-254. (Year: 2013).*
Yu, J., Vodyanik, M. A., Smuga-Otto, K., Antosiewicz-Bourget, J., Frane, J. L., Tian, S., . . . & Thomson, J. A. (2007). Induced pluripotent stem cell lines derived from human somatic cells. science, 318(5858), 1917-1920. (Year: 2007).*
Spuul, P., Balistreri, G., Hellström, K., Golubtsov, A. V., Jokitalo, E., & Ahola, T. (2011). Assembly of alphavirus replication complexes from RNA and protein components in a novel trans-replication system in mammalian cells. Journal of virology, 85(10), 4739-4751. (Year: 2011).*
Ou et al. The 5'-Terminal Sequences of the Genomic RNAs of Several Alphaviruses. Journal of Molecular Biology, 1983. 168:1-15.*
The International Search Report (ISR) with Written Opinion for PCT/EP2018/074486 dated Nov. 8, 2018, pp. 1-12.
Yoshioka, Naohisa et al. "Enhanced generation of iPSCs from older adult human cells by a synthetic five-factor self-replicative RNA" Plos One (2017) vol. 12(7), pp. 1-17.

(Continued)

*Primary Examiner* — Christopher M Babic
*Assistant Examiner* — Kimberly A Aron
(74) *Attorney, Agent, or Firm* — McDonnell Boehnen Hulbert & Berghoff LLP

(57) ABSTRACT

The present invention embraces a RNA replicon that can be replicated by a replicase of alphavirus origin and comprises an open reading frame encoding a reprogramming factor. Such RNA replicons are useful for expressing a reprogramming factor in a cell, in particular a somatic cell. Cells engineered to express such reprogramming factors are useful in cell transplantation therapies.

19 Claims, 7 Drawing Sheets

(56) References Cited

OTHER PUBLICATIONS

Stem Cell Technologies "ReproRNA-OKSGM Non-Integrating Reprogramming Vector" Stem Cell Technologies Dec. 1, 2016 (Dec. 1, 2016). XP002786324, Retrieved from the Internet: URL:https://cdn.stemcell.com/media/files/brochure/BRDX20456-ReproRNA_OKSGM_Non_Integrating_Reprogramming_Vector.pdf?_ga_=2.50334124.422273916.1541500364-858725074.1541500364, retrieved on Nov. 5, 2018.
EMD Millipore Corporation "SimpliconTM RNA Reprogramming Kit" EMD Millipore Corporation Mar. 1, 2016 XP002786325, Retrieved from the Internet: URL:https:jjwww.merckmillipore.com/NL/en/product/Simplicon-Reprogramming-RNA-OKSG.MM_NF-SCR549#anchor_BRO—retrieved on Nov. 5, 2018.
Yoshioka, Naohisa et al. "Efficient Generation of Human iPS Cells by a Synthetic Self-Replicative RNA" Cell Stem Cell (2013) vol. 13(2), pp. 246-254.

\* cited by examiner

RNA REPLICON FOR REPROGRAMMING SOMATIC CELLS

CROSS-REFERENCE TO RELATED APPLICATIONS

This application is a U.S. national phase of International Application No. PCT/EP2018/074486, filed Sep. 11, 2018, which claims priority from PCT/EP2017/073063, filed Sep. 13, 2017, the disclosure of each of which is hereby incorporated by reference in its entirety.

TECHNICAL FIELD OF THE INVENTION

The present invention embraces a RNA replicon that can be replicated by a replicase of alphavirus origin and comprises an open reading frame encoding a reprogramming factor. Such RNA replicons are useful for producing cells having stem cell characteristics from somatic cells and, in particular, in methods for de-differentiating somatic cells into cells having stem cell characteristics, in particular pluripotency, such as stem-like cells without generating embryos or foetuses by introducing one or more of the RNA replicons into somatic cells and culturing the somatic cells allowing the cells to de-differentiate. After being de-differentiated, the cells can be induced to re-differentiate into the same or a different somatic cell type such as neuronal, hematopoietic, muscle, epithelial, and other cell types. The stem-like cells derived by the present invention have medical applications for treatment of degenerative diseases by "cell therapy" and may be utilized in novel therapeutic strategies in the treatment of cardiac, neurological, endocrinological, vascular, retinal, dermatological, muscular-skeletal disorders, and other diseases.

BACKGROUND OF THE INVENTION

Stem cells also called progenitor cells are cells with abilities to self-renew, to remain undifferentiated, and to become differentiated into one or more specialized cell types with mature phenotypes. Stem cells are not terminally differentiated and they are not at the end of a differentiation pathway.

Totipotent cells contain all the genetic information needed to create all the cells of the body, including the cells of the placenta. Human cells have this totipotent capacity only during the first few divisions of a fertilized egg. After three to four divisions of totipotent cells, there follows a series of stages in which the cells become increasingly specialized. The next stage of division results in pluripotent cells, which are highly versatile and can give rise to any cell type except the cells of the placenta or other supporting tissues of the uterus. At the next stage, cells become multipotent, meaning they can give rise to several other cell types, but those types are limited in number. At the end of the long chain of cell divisions that make up the embryo are "terminally differentiated" cells that are considered to be permanently committed to a specific function.

There are three main groups of stem cells: (i) adult or somatic stem cells (post-natal), which exist in all post-natal organisms, (ii) embryonic stem cells, which can be derived from a pre-embryonic or embryonic developmental stage and (iii) fetal stem cells (pre-natal), which can be isolated from the developing fetus.

Stem cell technologies involving the isolation and use of human embryonic stem cells have become an important subject of medical research. Human embryonic stem cells have a potential to differentiate into any and all of the cell types in the human body, including complex tissues. It is expected that many diseases resulting from the dysfunction of cells may be amenable to treatment by the administration of human embryonic stem cells or human embryonic stem cell-derived cells. The ability of pluripotent embryonic stem cells to differentiate and give rise to a plurality of specialized mature cells reveals the potential application of these cells as a means to replace, restore, or complement damaged or diseased cells, tissues, and organs. However, scientific and ethical considerations have slowed the progress of research using embryonic stem cells recovered from aborted embryos or embryos formed using in vitro fertilization techniques.

Adult stem cells are present only at low frequencies and exhibit restricted differentiation potential and poor growth. A further problem associated with using adult stems cells is that these cells are not immunologically privileged, or can lose their immunological privilege after transplant, wherein the term "immunologically privileged" is used to denote a state where the recipient's immune system does not recognize the cells as foreign. Thus, only autologous transplants are possible in most cases when adult stem cells are used. Most presently envisioned forms of stem cell therapy are essentially customized medical procedures and therefore economic factors associated with such procedures limit their wide ranging potential.

The restoration of expression of at least some measured embryonic-specific genes has been observed in somatic cells following fusion with embryonic stem cells. However, the resulting cells are hybrids, often with a tetraploid genotype, and therefore not suited as normal or histocompatible cells for transplant purposes.

The use of somatic cell nuclear transfer has been shown to adequately reprogram somatic cell nuclear content to adopt pluripotency, however, raises a set of concerns beyond the moral status. The stresses placed on both the egg cell and the introduced nucleus are enormous, leading to a high loss in resulting cells. Furthermore, the procedure has to be performed manually under a microscope, and therefore, somatic cell nuclear transfer is very resource intensive. In addition, not all of the donor cell's genetic information is transferred, as the donor cell's mitochondria that contain their own mitochondrial DNA are left behind. The resulting hybrid cells retain those mitochondrial structures which originally belonged to the egg. As a consequence, clones are not perfect copies of the donor of the nucleus.

A major step towards patient derived pluripotent cells was achieved by Takahashi et al. in 2006. It was shown that the overexpression of defined transcription factors (TFs) which are known to regulate and maintain stem cell pluripotency (Takahasi et al., 2006, Cell 126, 663-676; Schulz & Hoffmann, 2007, Epigenetics 2, 37-42) can induce a pluripotent state of murine somatic fibroblasts, termed induced pluripotent stem (iPS) cells. In this study the authors identified OCT3/4, SOX2, KLF4 and c-MYC as being required for iPS cell generation (Takahasi et al., 2006). In a subsequent study the authors showed that the same TFs are able to reprogram adult human fibroblasts (Takahasi et al., 2007, Cell 131, 861-872), while others attributed this activity to a modified TF-cocktail composed of OCT3/4, SOX2, NANOG and LIN28 regarding human (Yu et al., 2007, Science 318, 1917) or murine fibroblasts (Wernig et al., 2007, Nature 448, 318-324). For those initial studies as well as most subsequent studies the reprogramming TFs were overexpressed using retro- or lentiviral vectors. Due to the silencing of viral promoters these studies reproducibly show that the expression of exogenous TFs is shut down during the reprogramming process (reviewed by Hotta & Ellis, 2008, J. Cell Biochem. 105, 940-948). Accordingly, the pluripotent state is maintained by activated endogenous transcription factors. Furthermore, the silencing of the virally expressed TFs is prerequisite for the subsequent re-differentiation of iPS cells to tissue specific precursors (Yu et al., 2007). A major disadvantage of viral delivery is the stochastic reactivation of integrated retroviruses encoding potent oncogenes, which in the case of c-MYC led to the induction of tumors in chimeric mice (Okita et al., 2007, Nature 448, 313-317). Meanwhile it has been demonstrated that the generation of iPS cells is possible in absence of MYC (Nakagawa et al., 2008, Nat. Biotechnol., 26(1), 101-106). Overall, only OCT4 and SOX2 have been reported being essential for the reprogramming, oncogenes like MYC and KLF4 seem to acts like enhancers (McDevitt & Palecek, 2008, Curr. Opin. Biotechnol. 19, 527-33). Accordingly it has been shown that other transforming gene products like SV40 Large-T antigen or hTERT can improve the efficiency of iPS generation (Mali et al., 2008, Stem Cells 26, 1998-2005). As the epigenetic reprogramming involves chromatin remodelling the addition of histone deacetylase (HDAC) inhibitors (like valproic acid) or DNA methyltransferase inhibitors (like 5'-azaC) greatly improve the reprogramming efficiency (Huangfu et al., 2008, Nat. Biotechnol. 26, 795-797) and reduced the need for TFs to OCT4 and SOX2 (Huangfu et al., 2008, Nat. Biotechnol. 26, 1269-1275).

Another strategy to reduce the risk associated with retroviral intergration into the host genome is the use of non-integrating adenoviral vectors, which mediate a transient transgene expression sufficient for reprogramming (Stadtfeld et al., 2008, 322, 945-949). Transgene integration is also avoided by the use of conventional eukaryotic expression plasmids leading to transient gene expression. So far, with this strategy MEFs have been successfully reprogrammed to iPS cells (Okita et al., 2008, Science 322, 949-53). Genomic integration has not been detected in this study, however, stable genomic integration in a small fraction of the cells of transfected plasmid DNA cannot be completely excluded.

Adult human fibroblasts are easily derived from healthy donors or—in future clinical applications—from patients without risky surgical intervention. However, a recent study has shown that human keratinocytes are more easily and more efficiently reprogrammed to iPS cells, and that e.g. hair follicle derived keratinocytes might be the better source of choice for patient derived iPS cells (Aasen et al., 2008, Nat. Biotechnol. 26(11), 1276-84).

There remains a need for technologies for reprogramming differentiated somatic cells to produce de-differentiated or reprogrammed cells in high number and with good quality.

Nucleic acid molecules comprising foreign genetic information encoding one or more polypeptides for prophylactic and therapeutic purposes have been studied in biomedical research for many years. Influenced by safety concerns associated with the use of deoxyribonucleic acid (DNA) molecules, ribonucleic acid (RNA) molecules have received growing attention in recent years. Various approaches have been proposed, including administration of single stranded or double-stranded RNA, in the form of naked RNA, or in complexed or packaged form, e.g. in non-viral or viral delivery vehicles. In viruses and in viral delivery vehicles, the genetic information is typically encapsulated by proteins and/or lipids (virus particle). For example, engineered RNA virus particles derived from RNA viruses have been proposed as delivery vehicle for treating plants (WO 2000/053780 A2) or for vaccination of mammals (Tubulekas et al., 1997, Gene, vol. 190, pp. 191-195). In general, RNA viruses are a diverse group of infectious particles with an RNA genome. RNA viruses can be sub-grouped into single-stranded RNA (ssRNA) and double-stranded RNA (dsRNA) viruses, and the ssRNA viruses can be further generally divided into positive-stranded [(+) stranded] and/or negative-stranded [(−) stranded] viruses. Positive-stranded RNA viruses are prima facie attractive as a delivery system in biomedicine because their RNA may serve directly as template for translation in the host cell.

Alphaviruses are typical representatives of positive-stranded RNA viruses. The hosts of alphaviruses include a wide range of organisms, comprising insects, fish and mammals, such as domesticated animals and humans. Alphaviruses replicate in the cytoplasm of infected cells (for review of the alphaviral life cycle see Jose et al., Future Microbiol., 2009, vol. 4, pp. 837-856). The total genome length of many alphaviruses typically ranges between 11,000 and 12,000 nucleotides, and the genomic RNA typically has a 5'-cap, and a 3' poly(A) tail. The genome of alphaviruses encodes non-structural proteins (involved in transcription, modification and replication of viral RNA and in protein modification) and structural proteins (forming the virus particle). There are typically two open reading frames (ORFs) in the genome. The four non-structural proteins (nsP1-nsP4) are typically encoded together by a first ORF beginning near the 5' terminus of the genome, while alphavirus structural proteins are encoded together by a second ORF which is found downstream of the first ORF and extends near the 3' terminus of the genome. Typically, the first ORF is larger than the second ORF, the ratio being roughly 2:1.

In cells infected by an alphavirus, only the nucleic acid sequence encoding non-structural proteins is translated from the genomic RNA, while the genetic information encoding structural proteins is translatable from a subgenomic transcript, which is an RNA molecule that resembles eukaryotic messenger RNA (mRNA; Gould et al., 2010, Antiviral Res., vol. 87 pp. 111-124). Following infection, i.e. at early stages of the viral life cycle, the (+) stranded genomic RNA directly acts like a messenger RNA for the translation of the open reading frame encoding the non-structural poly-protein (nsP1234). In some alphaviruses, there is an opal stop codon between the coding sequences of nsP3 and nsP4: polyprotein P123, containing nsP1, nsP2, and nsP3, is produced when translation terminates at the opal stop codon, and polyprotein P1234, containing in addition nsP4, is produced upon readthrough of this opal codon (Strauss & Strauss, Microbiol. Rev., 1994, vol. 58, pp. 491-562; Rupp et al., 2015, J. Gen. Virology, vol. 96, pp. 2483-2500). nsP1234 is auto-proteolytically cleaved into the fragments nsP123 and nsP4. The polypeptides nsP123 and nsP4 associate to form the (−) strand replicase complex that transcribes (−) stranded RNA, using the (+) stranded genomic RNA as template. Typically at later stages, the nsP123 fragment is completely cleaved into individual proteins nsP1, nsP2 and nsP3 (Shirako & Strauss, 1994, J. Virol., vol. 68, pp. 1874-1885). All four proteins form the (+) strand replicase complex that synthesizes new (+) stranded genomes, using the (−) stranded complement of genomic RNA as template (Kim et al., 2004, Virology, vol. 323, pp. 153-163, Vasiljeva et al., 2003, J. Biol. Chem. vol. 278, pp. 41636-41645).

In infected cells, subgenomic RNA as well as new genomic RNA is provided with a 5'-cap by nsP1 (Pettersson et al. 1980, Eur. J. Biochem. 105, 435-443; Rozanov et al., 1992, J. Gen. Virology, vol. 73, pp. 2129-2134), and provided with a poly-adenylate [poly(A)] tail by nsP4 (Rubach et al., Virology, 2009, vol. 384, pp. 201-208). Thus, both subgenomic RNA and genomic RNA resemble messenger RNA (mRNA).

Alphavirus structural proteins (core nucleocapsid protein C, envelope protein E2 and envelope protein E1, all constituents of the virus particle) are typically encoded by one single open reading frame under control of a subgenomic promoter (Strauss & Strauss, Microbiol. Rev., 1994, vol. 58, pp. 491-562). The subgenomic promoter is recognized by aiphaviral non-structural proteins acting in cis. In particular, alphavirus replicase synthesizes a (+) stranded subgenomic transcript using the (−) stranded complement of genomic RNA as template. The (+) stranded subgenomic transcript encodes the alphavirus structural proteins (Kim et al., 2004, Virology, vol. 323, pp. 153-163, Vasiljeva et al., 2003, J. Biol. Chem. vol. 278, pp. 41636-41645). The subgenomic RNA transcript serves as template for translation of the open reading frame encoding the structural proteins as one polyprotein, and the poly-protein is cleaved to yield the structural proteins. At a late stage of alphavirus infection in a host cell, a packaging signal which is located within the coding sequence of nsP2 ensures selective packaging of genomic RNA into budding virions, packaged by structural proteins (White et al., 1998, J. Viral., vol. 72, pp. 4320-4326).

In infected cells, (−) strand RNA synthesis is typically observed only in the first 3-4 h post infection, and is undetectable at late stages, at which time the synthesis of only (+) strand RNA (both genomic and subgenomic) is observed. According to Frolov et al., 2001, RNA, vol. 7, pp. 1638-1651, the prevailing model for regulation of RNA synthesis suggests a dependence on the processing of the non-structural poly-protein: initial cleavage of the non-structural polyprotein nsP1234 yields nsP123 and nsP4; nsP4 acts as RNA-dependent RNA polymerase (RdRp) that is active for (−) strand synthesis, but inefficient for the generation of (+) strand RNAs. Further processing of the polyprotein nsP123, including cleavage at the nsP2/nsP3 junction, changes the template specificity of the replicase to increase synthesis of (+) strand RNA and to decrease or terminate synthesis of (−) strand RNA.

The synthesis of aiphaviral RNA is also regulated by cis-acting RNA elements, including four conserved sequence elements (CSEs; Strauss & Strauss, Microbiol. Rev., 1994, vol. 58, pp. 491-562; and Frolov, 2001, RNA, vol. 7, pp. 1638-1651).

In general, the 5' replication recognition sequence of the alphavirus genome is characterized by low overall homology between different alphaviruses, but has a conserved predicted secondary structure. The 5' replication recognition sequence of the alphavirus genome is not only involved in translation initiation, but also comprises the 5' replication recognition sequence comprising two conserved sequence elements involved in synthesis of viral RNA, CSE 1 and CSE 2. For the function of CSE 1 and 2, the secondary structure is believed to be more important than the linear sequence (Strauss & Strauss, Microbiol. Rev., 1994, vol. 58, pp. 491-562).

In contrast, the 3' terminal sequence of the alphavirus genome, i.e. the sequence immediately upstream of the poly(A) sequence, is characterized by a conserved primary structure, particularly by conserved sequence element 4 (CSE 4), also termed "19-nt conserved sequence", which is important for initiation of (−) strand synthesis.

CSE 3, also termed "junction sequence" is a conserved sequence element on the (+) strand of alphaviral genomic RNA, and the complement of CSE 3 on the (−) strand acts as promoter for subgenomic RNA transcription (Strauss & Strauss, Microbiot. Rev., 1994, vol. 58, pp. 491-562; Frolov et al., 2001, RNA, vol. 7, pp. 1638-1651). CSE 3 typically overlaps with the region encoding the C-terminal fragment of nsP4.

In addition to alphavirus proteins, also host cell factors, presumably proteins, may bind to conserved sequence elements (Strauss & Strauss, supra).

Alphavirus-derived vectors have been proposed for delivery of foreign genetic information into target cells or target organisms. In simple approaches, the open reading frame encoding alphaviral structural proteins is replaced by an open reading frame encoding a protein of interest. Alphavirus-based trans-replication systems rely on alphavirus nucleotide sequence elements on two separate nucleic acid molecules: one nucleic acid molecule encodes a viral replicase (typically as poly-protein nsP1234), and the other nucleic acid molecule is capable of being replicated by said replicase in trans (hence the designation trans-replication system). trans-replication requires the presence of both these nucleic acid molecules in a given host cell. The nucleic acid molecule capable of being replicated by the replicase in trans must comprise certain alphaviral sequence elements to allow recognition and RNA synthesis by the alphaviral replicase.

As described herein, the aspects and embodiments of the present invention address the need to provide technologies for reprogramming differentiated somatic cells to produce de-differentiated or reprogrammed cells in high number and with good quality.

SUMMARY OF THE INVENTION

The present invention provides technologies of producing reprogrammed cells using RNA replicons encoding reprogramming factors. These technologies use cells that are easily and inexpensively obtained in unlimited quantities and provide reprogrammed cells useful in cell therapy. The approach according to the present invention opens the possibility of reprogramming without modification of the host genome.

The present invention exploits the fact that, when provided with appropriate factors, a terminally differentiated cell's fate can be redirected to pluripotentiality. Specifically, the present invention provides technology for reprogramming an animal differentiated somatic cell to a cell having stem cell properties. This method allows de-differentiation of one type of somatic cells into pluripotent stem-like cells using a defined system in vitro. The method of the invention in one embodiment provides autologous (isogeneic) cell types for cell transplantation in the same individual that donated the initial somatic cell sample.

According to the present invention, one or more somatic cells are provided with one or more RNA replicons capable of expressing one or more factors that induce the reprogramming of somatic cells to cells having stem cell characteristics. Expression of these factors confers characteristics of an undifferentiated cell to a somatic cell and facilitates reprogramming of the somatic cell.

Different types of RNA replicons are useful according to the invention. In one type of RNA replicon the open reading frame of an alphavirus-derived RNA vector encoding alphavirus structural proteins is replaced by an open reading frame encoding a reprogramming factor. A respective replicon is illustrated as "cis-replicon; WT-RRS" in FIG. 1. Other types of RNA replicons according to the invention relate to alphavirus-based trans-replication systems. A respective replicon is illustrated as "trans-replicon; WT- RRS" in FIG. 1. Such replicon is associated with the advantage of allowing for amplification of an open reading frame encoding a reprogramming factor under control of a subgenomic promoter.

The open reading frame encoding nsP1234 typically overlaps with the 5' replication recognition sequence of the alphavirus genome (coding sequence for nsP1) and typically also with the subgenomic promoter comprising CSE 3 (coding sequence for nsP4). Accordingly, in such "trans-replicon", the 5' replication recognition sequence required for RNA replication comprises an AUG start codon for nsP1 and thus overlaps with the coding sequence for the N-terminal fragment of the alphavirus non-structural protein and a replicon comprising the 5' replication recognition sequence will typically encode (at least) a part of alphavirus non-structural protein, typically the N-terminal fragment of nsP1. This is disadvantageous in several aspects: In the case of cis-replicons this overlap limits for instance adaptation of codon usage of the replicase ORF to different mammalian target cells (human, mouse, farm animals). It is conceivable that the secondary structure of the 5' replication recognition sequence as it is found in the viruses is not optimal in every target cell. However, the secondary structure cannot be altered freely as possibly resulting amino acid changes in the replicase ORF have to be considered and tested for the effect on replicase function. It is also not possible to exchange the complete replicase ORF for replicases from heterologous origin since this can results in disruption of the 5' replication recognition sequence structure. In the case of trans-replicons this overlap results in the synthesis of a fragment of nsP1 protein since the 5' replication recognition sequence needs to be retained in trans replicons. A fragment of nsP1 is typically not required and not desired: the undesired translation imposes an unnecessary burden on the host cell, and RNA replicons intended for therapeutic applications that encode, in addition to a pharmaceutically active protein, a fragment of nsP1, may face regulatory concerns. For instance, it will be necessary to demonstrate that the truncated nsP1 does not create unwanted side effects. In addition, the presence of an AUG start codon for nsP1 within the 5' replication recognition sequence has prevented the design of trans-replicons encoding a heterologous gene of interest in a fashion wherein the start codon for translation of the gene of interest is at the most 5' position that is accessible for ribosomal translation initiation. In turn, 5'-cap-dependent translation of transgenes from prior art trans-replicon RNA is challenging, unless cloned as fusion protein in frame to the start codon of nsP1 (such fusion constructs are described e.g. by Michel et al., 2007, Virology, vol. 362, pp. 475-487). Such fusion constructs lead to the same unnecessary translation of the nsP1 fragment mentioned above, raising the same concerns as above. Moreover, fusion proteins cause additional concerns as they might alter the function or activity of the fused transgene of interest, or when used as vaccine vector, peptides spanning the fusion region could alter immunogenicity of the fused antigen.

Accordingly, the present invention provides a further type of RNA replicon which comprises sequence elements required for replication by the replicase, but these sequence elements do not encode any protein or fragment thereof, such as an alphavirus non-structural protein or fragment thereof. Thus, the sequence elements required for replication by the replicase and protein-coding regions are uncoupled. A respective replicon is illustrated as "trans-replicon; Δ5ATG-RRSΔSGP" in FIG. 1. Uncoupling is achieved by the removal of at least one initiation codon compared to a native alphavirus genomic RNA. The replicase may be encoded by the RNA replicon or by a separate nucleic acid molecule. In one particularly preferred embodiment, such replicon does not comprise a subgenomic promotor and the start codon for translation of the open reading frame encoding a reprogramming factor is at the most 5' position that is accessible for ribosomal translation initiation.

In a first aspect, the present invention provides a RNA replicon comprising an open reading frame encoding a reprogramming factor. In one embodiment, the RNA replicon comprises one or more further open reading frames encoding the same or different reprogramming factors. In one embodiment, the RNA replicon comprises open reading frames encoding a functional set of reprogramming factors which is a set of reprogramming factors useful in reprogramming somatic cells to cells having stem cell characteristics, i.e., the set of reprogramming factors when expressed in a somatic cell is sufficient for effecting reprogramming of the somatic cell to a cell having stem cell characteristics.

In one embodiment, the reprogramming factor is selected from the group consisting of OCT4, SOX2, KLF4, c-MYC, LIN28 and NANOG.

In one embodiment, the RNA replicon is a cis-replicon or trans-replicon.

In one embodiment, the RNA replicon comprises a first open reading frame encoding functional alphavirus non-structural protein or a reprogramming factor.

In one embodiment, the RNA replicon comprises a 5' replication recognition sequence, wherein the 5' replication recognition sequence is characterized in that it comprises the removal of at least one initiation codon compared to a native alphavirus 5' replication recognition sequence.

In one embodiment, the first open reading frame does not overlap with the 5' replication recognition sequence.

In one embodiment, the initiation codon of the first open reading frame is in the 5'→3' direction of the RNA replicon the first functional initiation codon.

In one embodiment, in particular if the RNA replicon is a cis-replicon, the RNA replicon comprises an open reading frame encoding functional alphavirus non-structural protein. The RNA replicon may comprise one or more open reading frames encoding one or more reprogramming factors.

In one embodiment, in particular if the RNA replicon is a trans-replicon, the RNA replicon does not comprise an open reading frame encoding functional alphavirus non-structural protein. In this embodiment, the functional alphavirus non-structural protein for replication of the replicon may be provided in trans as described herein. The RNA replicon may comprise one or more open reading frames encoding one or more reprogramming factors. Thus, in one embodiment, the RNA replicon may only comprise one open reading frame encoding one reprogramming factor. Several of such RNA replicons may form a set of RNA replicons such as a functional set of RNA replicons as described herein.

In one embodiment, the RNA replicon comprises a first open reading frame encoding a protein of interest, e.g. functional alphavirus non-structural protein or a reprogramming factor. In one embodiment, the first open reading frame does not overlap with the 5' replication recognition sequence.

If the RNA replicon is a cis-replicon, the first open reading generally will be an open reading frame encoding functional alphavirus non-structural protein. In this embodiment, the RNA replicon generally comprises at least one further open reading frame encoding a reprogramming factor which is under control of a subgenomic promotor. If the RNA replicon is a trans-replicon, the first open reading generally will be an open reading encoding a reprogramming factor and the RNA replicon preferably comprises no open reading frame encoding functional alphavirus non-structural protein.

In one embodiment, the RNA replicon comprises a (modified) 5' replication recognition sequence and a first open reading frame encoding a protein of interest, e.g. functional alphavirus non-structural protein or a reprogramming factor, located downstream from the 5' replication recognition sequence, wherein the 5' replication recognition sequence and the first open reading frame encoding a protein of interest do not overlap and preferably the 5' replication recognition sequence does not overlap with any open reading frame of the RNA replicon, e.g. the 5' replication recognition sequence does not contain a functional initiation codon and preferably does not contain any initiation codon. Most preferably, the initiation codon of the first open reading frame is in the 5'→3' direction of the RNA replicon the first functional initiation codon, preferably the first initiation codon. In one embodiment, the first open reading frame and preferably the entire RNA replicon does not express non-functional alphavirus non-structural protein, such as a fragment of alphavirus non-structural protein, in particular a fragment of nsP1 and/or nsP4. In one embodiment, the functional alphavirus non-structural protein is heterologous to the 5' replication recognition sequence. In one embodiment, the first open reading frame is not under control of a subgenomic promotor.

In one embodiment, the first open reading frame encodes functional alphavirus non-structural protein and the RNA replicon comprises at least one further open reading frame encoding a reprogramming factor which is under control of a subgenomic promotor. In one embodiment, the subgenomic promotor and the first open reading frame do not overlap.

In another embodiment, the first open reading frame encodes a reprogramming factor and the RNA replicon preferably comprises no open reading frame encoding functional alphavirus non-structural protein. The RNA replicon may comprise at least one further open reading frame encoding one or more reprogramming factors (e.g., one or more reprogramming factors which together with the reprogramming factor encoded by the first open reading frame form a functional set of reprogramming factors) which is under control of a subgenomic promotor. In one embodiment, the subgenomic promotor and the first open reading frame do not overlap.

In one particularly preferred embodiment, the first open reading frame, located downstream from the 5' replication recognition sequence, encodes a reprogramming factor, the 5' replication recognition sequence and the first open reading frame do not overlap, the 5' replication recognition sequence does not contain a functional initiation codon and preferably does not contain any initiation codon and the RNA replicon does not comprise an open reading frame encoding functional alphavirus non-structural protein. In this embodiment, the initiation codon of the first open reading frame is in the 5'→3' direction of the RNA replicon the first functional initiation codon, preferably the first initiation codon such that the RNA replicon does not express non-functional alphavirus non-structural protein, such as a fragment of alphavirus non-structural protein, in particular a fragment of nsP1 and/or nsP4. The RNA replicon may comprise at least one further open reading frame encoding one or more reprogramming factors (e.g., one or more reprogramming factors which together with the reprogramming factor encoded by the first open reading frame form a functional set of reprogramming factors) which is under control of a subgenomic promotor. In one embodiment, the subgenomic promotor and the first open reading frame do not overlap.

In one embodiment, the 5' replication recognition sequence of the RNA replicon that is characterized by the removal of at least one initiation codon comprises a sequence homologous to about 250 nucleotides at the 5' end of an alphavirus. In a preferred embodiment, it comprises a sequence homologous to about 300 to 500 nucleotides at the 5' end of an alphavirus. In a preferred embodiment, it comprises the 5'-terminal sequence required for efficient replication of the specific alphavirus species that is parental to the vector system.

In one embodiment, the 5' replication recognition sequence of the RNA replicon comprises sequences homologous to conserved sequence element 1 (CSE 1) and conserved sequence element 2 (CSE 2) of an alphavirus.

In a preferred embodiment, the RNA replicon comprises CSE 2 and is further characterized in that it comprises a fragment of an open reading frame of a non-structural protein from an alphavirus. In a more preferred embodiment, said fragment of an open reading frame of a non-structural protein does not comprise any initiation codon.

In one embodiment, the 5' replication recognition sequence comprises a sequence homologous to an open reading frame of a non-structural protein or a fragment thereof from an alphavirus, wherein the sequence homologous to an open reading frame of a non-structural protein or a fragment thereof from an alphavirus is characterized in that it comprises the removal of at least one initiation codon compared to the native alphavirus sequence.

In a preferred embodiment, the sequence homologous to an open reading frame of a non-structural protein or a fragment thereof from an alphavirus is characterized in that it comprises the removal of at least the native start codon of the open reading frame of a non-structural protein.

In a preferred embodiment, the sequence homologous to an open reading frame of a non-structural protein or a fragment thereof from an alphavirus is characterized in that it comprises the removal of one or more initiation codons other than the native start codon of the open reading frame of a non-structural protein. In a more preferred embodiment, said nucleic acid sequence is additionally characterized by the removal of the native start codon of the open reading frame of a non-structural protein, preferably of nsP1.

In a preferred embodiment, the 5' replication recognition sequence comprises one or more stem loops providing functionality of the 5' replication recognition sequence with respect to RNA replication. In a preferred embodiment, one or more stem loops of the 5' replication recognition sequence are not deleted or disrupted. More preferably, one or more of stem loops 1, 3 and 4, preferably all stem loops 1, 3 and 4, or stem loops 3 and 4 are not deleted or disrupted. More preferably, none of the stem loops of the 5' replication recognition sequence is deleted or disrupted.

In a preferred embodiment, the RNA replicon comprises one or more nucleotide changes compensating for nucleotide pairing disruptions within one or more stem loops introduced by the removal of at least one initiation codon.

In one embodiment, the RNA replicon does not comprise an open reading frame encoding a truncated alphavirus non-structural protein.

In one embodiment, the RNA replicon comprises a 3' replication recognition sequence.

In one embodiment, the RNA replicon is characterized in that the protein of interest encoded by the first open reading frame can be expressed from the RNA replicon as a template. In one embodiment, the RNA replicon comprises a subgenomic promoter controlling production of subgenomic RNA comprising the first open reading frame.

In one embodiment, the RNA replicon is characterized in that it comprises a subgenomic promoter. Typically, the subgenomic promoter controls production of subgenomic RNA comprising an open reading frame encoding a protein of interest.

In one embodiment, the protein of interest encoded by the first open reading frame can be expressed from the RNA replicon as a template. In a more preferred embodiment, the protein of interest encoded by the first open reading frame can additionally be expressed from the subgenomic RNA.

In a preferred embodiment, the RNA replicon is further characterized in that it comprises a subgenomic promoter controlling production of subgenomic RNA comprising a second open reading frame encoding a protein of interest. The protein of interest may be a second protein that is identical to or different from the protein of interest encoded by the first open reading frame.

In a more preferred embodiment, the subgenomic promoter and the second open reading frame encoding a protein of interest are located downstream from the first open reading frame encoding a protein of interest.

In one embodiment, the RNA replicon can be replicated by functional alphavirus non-structural protein.

In a second aspect, the present invention provides a set of RNA replicons, i.e., a set comprising at least 2 such as 2, 3, 4, 5, 6 or even more RNA replicons, wherein each of the RNA replicons comprises at least one open reading frame encoding a reprogramming factor and the set of RNA replicons encodes a set of reprogramming factors.

In one embodiment, each of the RNA replicons comprises one open reading frame encoding a reprogramming factor.

In one embodiment, the set of reprogramming factors is a functional set of reprogramming factors, i.e., it is useful and/or sufficient in reprogramming somatic cells to cells having stem cell characteristics.

In one embodiment, the set of reprogramming factors comprises OCT4 and SOX2. In one embodiment, the set of reprogramming factors further comprises KLF4 and/or c-MYC. In one embodiment, the set of reprogramming factors further comprises NANOG and/or LIN28.

In one embodiment, the set of reprogramming factors comprises OCT4, SOX2, KLF4 and c-MYC. In one embodiment, the set of reprogramming factors further comprises LIN28 and optionally NANOG.

In one embodiment, the set of reprogramming factors comprises OCT4, SOX2, NANOG and LIN28.

In one embodiment, at least one RNA replicon of the set is a RNA replicon according to the invention. In one embodiment, each RNA replicon of the set is a RNA replicon according to the invention.

In a third aspect, the present invention provides a system comprising:
 a RNA construct for expressing functional alphavirus non-structural protein,
 the RNA replicon according to the first aspect of the invention or the set of RNA replicons according to the second aspect of the invention, which can be replicated by the functional alphavirus non-structural protein in trans. Preferably, the RNA replicon or the set of RNA replicons is further characterized in that it does not encode a functional alphavirus non-structural protein.

In one embodiment, the RNA replicon according to the first aspect, the set of RNA replicons according to the second aspect or the system according to the third aspect is characterized in that the alphavirus is Venezuelan equine encephalitis virus.

In a fourth aspect, the present invention provides DNA (i.e., one or more DNA molecules) comprising nucleic acid sequence encoding the RNA replicon according to the first aspect, the set of RNA replicons according to the second aspect or the system according to the third aspect.

In a further aspect, the present invention provides a method of producing cells having stem cell characteristics comprising the step of introducing into somatic cells one or more RNA replicons according to the invention.

In a further aspect, the present invention provides a method for providing cells having stem cell characteristics comprising the steps of:
 (i) providing a cell population comprising somatic cells,
 (ii) providing one or more RNA replicons, wherein each of the one or more RNA replicons comprises an open reading frame encoding functional alphavirus non-structural protein, can be replicated by the functional alphavirus non-structural protein and comprises at least one open reading frame encoding a reprogramming factor,
 (iii) introducing the one or more RNA replicons into the somatic cells, such that the cells express a set of reprogramming factors useful in reprogramming somatic cells to cells having stem cell characteristics, and
 (iv) allowing the development of cells having stem cell characteristics.

In a further aspect, the present invention provides a method for providing cells having stem cell characteristics comprising the steps of:
 (i) providing a cell population comprising somatic cells,
 (ii) providing a RNA construct for expressing functional alphavirus non-structural protein,
 (iii) providing one or more RNA replicons, wherein each of the one or more RNA replicons can be replicated by the functional alphavirus non-structural protein in trans and comprises at least one open reading frame encoding a reprogramming factor,
 (iv) introducing the RNA construct and the one or more RNA replicons into the somatic cells, such that the cells express a set of reprogramming factors useful in reprogramming somatic cells to cells having stem cell characteristics, and
 (v) allowing the development of cells having stem cell characteristics.

According to the present invention, the one or more RNA replicons and optionally the RNA construct for expressing functional alphavirus non-structural protein preferably are introduced into the somatic cells by electroporation or lipofection.

In one embodiment, a RNA replicon comprises open reading frames encoding a functional set of reprogramming factors. In one embodiment, different RNA replicons comprise open reading frames encoding different reprogramming factors. In the latter embodiment, these different RNA replicons may be co-introduced either at the same time point or at different time points (optionally together with a RNA construct for expressing functional alphavirus non-structural protein) into cells to provide a functional set of reprogramming factors.

In one embodiment, the cells express the reprogramming factor(s).

In one embodiment, the one or more RNA replicons encode a set of reprogramming factors.

In one embodiment, each of the one or more RNA replicons comprises one open reading frame encoding a reprogramming factor.

In one embodiment, the set of reprogramming factors encoded by the one or more RNA replicons is a functional set of reprogramming factors, i.e., a set of reprogramming factors useful and/or sufficient in reprogramming somatic cells to cells having stem cell characteristics.

In one embodiment, the set of reprogramming factors comprises OCT4 and SOX2. In one embodiment, the set of reprogramming factors further comprises KLF4 and/or c-MYC. In one embodiment, the set of reprogramming factors further comprises NANOG and/or LIN28.

In one embodiment, the set of reprogramming factors comprises OCT4, SOX2, KLF4 and c-MYC. In one embodiment, the set of reprogramming factors further comprises LIN28 and optionally NANOG.

In one embodiment, the set of reprogramming factors comprises OCT4, SOX2, NANOG and LIN28.

In one embodiment, the method of the invention further comprises introducing into the somatic cells miRNA enhancing reprogramming of the somatic cells to cells having stem cell characteristics.

In one embodiment, the method of the invention further comprises culturing the somatic cells in the presence of at least one histone deacetylase inhibitor. In one embodiment, the at least one histone deacetylase inhibitor comprises valproic acid.

In one embodiment, the step of allowing the development of cells having stem cell characteristics comprises culturing the somatic cells under embryonic stem cell culture conditions, preferably conditions suitable for maintaining pluripotent stem cells in an undifferentiated state.

In one embodiment, the stem cell characteristics comprise an embryonic stem cell morphology, wherein said embryonic stem cell morphology preferably comprises morphological criteria selected from the group consisting of compact colonies, high nucleus to cytoplasm ratio and prominent nucleoli. In certain embodiments, the cells having stem cell characteristics have normal karyotypes, express telomerase activity, express cell surface markers that are characteristic for embryonic stem cells and/or express genes that are characteristic for embryonic stem cells. The cell surface markers that are characteristic for embryonic stem cells may be selected from the group consisting of stage-specific embryonic antigen-3 (SSEA-3), SSEA-4, tumor-related antigen-1-60 (TRA-1-60), TRA-1-81, and TRA-2-49/6E and the genes that are characteristic for embryonic stem cells may be selected from the group consisting of endogenous OCT4, endogenous NANOG, growth and differentiation factor 3 (GDF3), reduced expression 1 (REX1), fibroblast growth factor 4 (FGF4), embryonic cell-specific gene 1 (ESG1), developmental pluripotency-associated 2 (DPPA2), DPPA4, and telomerase reverse transcriptase (TERT).

In one embodiment, the cells having stem cell characteristics are de-differentiated and/or reprogrammed somatic cells. Preferably, the cells having stem cell characteristics exhibit the essential characteristics of embryonic stem cells such as a pluripotent state. Preferably, the cells having stem cell characteristics have the developmental potential to differentiate into advanced derivatives of all three primary germ layers. In one embodiment, the primary germ layer is endoderm and the advanced derivative is gut-like epithelial tissue. In a further embodiment, the primary germ layer is mesoderm and the advanced derivative is striated muscle and/or cartilage. In an even further embodiment, the primary germ layer is ectoderm and the advanced derivative is neural tissue and/or epidermal tissue. In one preferred embodiment, the cells having stem cell characteristics have the developmental potential to differentiate into neuronal cells and/or cardiac cells.

In one embodiment, the somatic cells are embryonic stem cell derived somatic cells with a mesenchymal phenotype. In a preferred embodiment, the somatic cells are fibroblasts such as fetal fibroblasts or postnatal fibroblasts or keratinocytes, preferably hair follicle derived keratinocytes. In further embodiments, the fibroblasts are lung fibroblasts, foreskin fibroblasts or dermal fibroblasts. In particular embodiments, the fibroblasts are fibroblasts as deposited at the American Type Culture Collection (ATCC) under Catalog No. CCL-186 or as deposited at the American Type Culture Collection (ATCC) under Catalog No. CRL-2097. In one embodiment, the fibroblasts are adult human dermal fibroblast. Preferably, the somatic cells are human cells. According to the present invention, the somatic cells may be genetically modified.

In one embodiment, at least one RNA replicon of the one or more RNA replicons is a RNA replicon according to the invention. In one embodiment, each RNA replicon of the one or more RNA replicons is a RNA replicon according to the invention. In one embodiment, the one or more RNA replicons comprise a set of RNA replicons according to the invention.

Particular embodiments of the methods of the present invention further comprise one or more of the steps of cultivating, propagating and cryopreserving the cells having stem cell characteristics.

In a further aspect, the present invention provides cells having stem cell characteristics produced by the method of the invention. In one embodiment, the cell is a recombinant cell.

In a further aspect, the present invention provides a cell expressing one or more reprogramming factors, preferably a functional set of reprogramming factors, comprising one or more RNA replicon(s) of the invention, which RNA replicon(s) comprise(s) (an) open reading frame(s) encoding the one or more reprogramming factors. The present invention also provides a population of such cells.

In a further aspect, the present invention provides a method for providing differentiated cell types comprising the steps of (i) providing cells having stem cell characteristics using the method of the invention, and (ii) culturing the cells having stem cell characteristics under conditions that induce or direct partial or complete differentiation to a differentiated cell type.

In a further aspect, the present invention relates to a method of providing differentiated cell types comprising the step of culturing the cells having stem cell characteristics of the present invention under conditions that induce or direct partial or complete differentiation to a differentiated cell type.

In one embodiment, the conditions that induce or direct partial or complete differentiation to a differentiated cell type comprise the presence of at least one differentiation factor. Preferably, the somatic cell type of the differentiated cells obtained according to the present invention is different from the somatic cell type of the somatic cells used for de-differentiation. Preferably, the de-differentiated cells are derived from fibroblastic cells and said re-differentiated cell types are different from fibroblastic cells. In another embodiment, the de-differentiated cells are derived from keratinocytes and said re-differentiated cell types are different from keratinocytes.

In a further aspect, the present invention relates to a kit for producing cells having stem cell characteristics comprising the RNA replicon according to the first aspect, the set of RNA replicons according to the second aspect or the system according to the third aspect. The kit may further comprise an embryonic stem cell culture medium.

In a further aspect, the present invention provides a pharmaceutical composition comprising the cells having stem cell characteristics of the invention, e.g., comprising a set of RNA replicons of the invention each RNA replicon encoding one of reprogramming factors of a functional set of reprogramming factors.

In even a further aspect, the present invention relates to a pharmaceutical composition comprising the RNA replicon according to the first aspect, the set of RNA replicons according to the second aspect or the system according to the third aspect.

In a further aspect, the present invention provides the pharmaceutical composition of the invention for use as a medicament.

In further aspects, the present invention relates to the use of the cells or the pharmaceutical composition of the present invention in medicine, in particular in transplantation medicine.

In a further aspect, the present invention provides a method for the treatment of a disease comprising administering to a subject a therapeutically effective amount of the pharmaceutical composition of the invention.

In a further aspect, the present invention provides a method of treating a subject having a disease, the method comprising administering to the subject cells having stem cell characteristics produced by the method of the invention.

In one embodiment, the cells may be autologous, allogeneic or syngeneic to the subject.

In one embodiment of all aspects of the invention, the method of treating further comprises obtaining a sample of somatic cells from a subject, and treating the cells by the methods of the invention to provide cells having stem cell characteristics. In one embodiment of all aspects of the invention, the cells having stem cell characteristics are transiently transfected with nucleic acid encoding one or more reprogramming factors. Thus, the nucleic acid encoding one or more reprogramming factors is not integrated into the genome of the cells. In one embodiment of all aspects of the invention, the somatic cells are from the subject to which the cells having stem cell characteristics are administered. In one embodiment of all aspects of the invention, the somatic cells are from a mammal which is different to the mammal to which the cells having stem cell characteristics are administered.

In one embodiment of the invention, a treatment comprises cell therapy such as cell transplantation therapy.

In a further aspect, the invention provides the agents and compositions described herein for use in the methods described herein.

Other features and advantages of the instant invention will be apparent from the following detailed description and claims.

Figure 1:
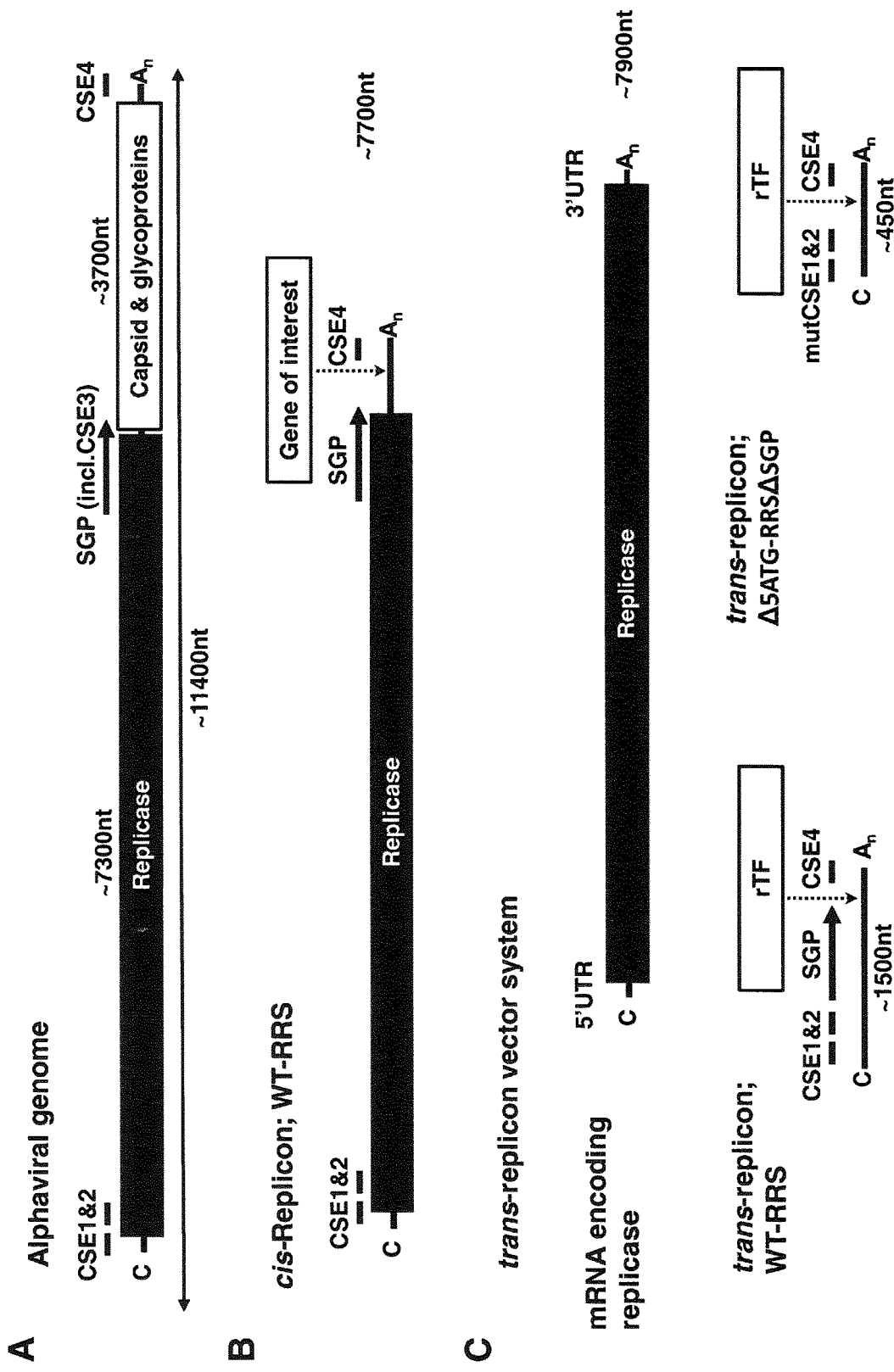
FIG. 1: Parental viral genome and vectors cis- and trans-replicating RNA (A) General organization of alphaviral genomes. Two large open reading frames (ORF) are separated by a subgenomic promoter (SGP). The 5' ORF encodes an enzyme complex for RNA amplification (replicase), the 3' ORF encodes the viral structural genes (Capsid and envelope glycoproteins). At the 5'-end two conserved sequence elements (CSE) build up the 5'-replication recognition sequence (RRS) overlapping partially with the replicase coding region. The 3' RRS is build by a CSE 4 (3'-terminal 19 nucleotides) and approximately 15 nucleotides of the poly-A tail ($A_n$). (B) cis-replicon vectors keep the WT sequence of RRS and SGP, they lack the ORF of the structural genes which is replaced by genes of interest. (C) trans-replicon (TR) vector systems. The cis-replicon is split into an mRNA encoding the replicase but being unable to replicate, and short RNAs amplified in trans by the replicase. These so called trans-replicons have two different designs, one contains all viral RRSs in the WT sequence identical to the cis-replicon. The other version contains a shortened 5'CSE mutated to remove any AUG codon that could serve as translation start codon. The removal of 5'AUG ensures that translation starts exclusively with the start codon of the ORF of interest, which is inserted downstream of the mutated 5'CSE. Genes of interest in this invention are six reprogramming transcription factors (rTF) promoting pluripotency (OCT4, SOX2, MYC, KLF4, NANOG, LIN28) and three interferon escape proteins of Vaccinia virus (E3, K3, B18).

cisReplicon WT-RRS: RNA replicon essentially corresponding to the genome of an alphavirus, except that the nucleic acid sequence encoding alphavirus structural proteins has been replaced by an open reading frame encoding a gene of interest ("Transgene"). When "Replicon WT-RRS" is introduced into a cell, the translation product of the open reading frame encoding replicase (nsP1234 or fragment(s) thereof) can drive replication of the RNA replicon in cis and drive synthesis of a nucleic acid sequence (the subgenomic transcript) downstream of the subgenomic promoter (SGP).

Trans-replicon or template RNA WT-RRS: RNA replicon essentially corresponding to "Replicon WT-RRS", except that most of the nucleic acid sequence encoding alphavirus non-structural proteins nsP1-4 has been removed. More specifically, the nucleic acid sequence encoding nsP2 and nsP3 has been removed completely; the nucleic acid sequence encoding nsP1 has been truncated so that the "Template RNA WT-RRS" encodes a fragment of nsP1, which fragment does not comprise the C-terminal fragment of nsP1 (but it comprises the N-terminal fragment of nsP1; nsP1*); the nucleic acid sequence encoding nsP4 has been truncated so that the "Template RNA WT-RRS" encodes a fragment of nsP4, which fragment does not comprise the N-terminal fragment of nsP4 (but it comprises the C-terminal fragment of nsP4; *nsP4). This truncated nsP4 sequence overlaps partially with the fully active subgenomic promoter. The nucleic acid sequence encoding nsP1* comprises all initiation codons of the nucleic acid sequence that encodes nsP1* in alphavirus found in nature (in the case of nsP1* from Semliki Forest virus, five specific initiation codons).

Δ5ATG-RRS: RNA replicon essentially corresponding to "Template RNA WT-RRS", except that it does not comprise any initiation codons of the nucleic acid sequence that encodes nsP1* in alphavirus found in nature (in the case of Semliki Forest virus, "Δ5ATG-RRS" corresponds to the removal of five specific initiation codons compared to Semliki Forest virus found in nature). All nucleotide changes introduced to remove start codons were compensated by additional nucleotide changes to conserve the predicted secondary structure of the RNA.

Δ5ATG-RRSΔSGP: RNA replicon essentially corresponding to "Δ5ATG-RRS", except that it does not comprise the subgenomic promoter (SGP) and does not comprise the nucleic acid sequence that encodes *nsP4. "Transgene 1"=a gene of interest.

Δ5ATG-RRS-bicistronic: RNA replicon essentially corresponding to "Δ5ATG-RRS", except that it comprises a first open reading frame encoding a first gene of interest ("Transgene 1") upstream of the subgenomic promoter, and a second open reading frame encoding a second gene of interest ("Transgene 2") downstream of the subgenomic promoter. The localization of the second open reading frame corresponds to the localization of the gene of interest ("Transgene") in the RNA replicon "Δ5ATG-RRS".

cisReplicon Δ5ATG-RRS: RNA replicon essentially corresponding to "Δ5ATG-RRS-bicistronic", except that the open reading frame encoding a first gene of interest encodes functional alphavirus non-structural protein (typically one open reading frame encoding the poly-protein nsP1-nsP2-nsP3-nsP4, i.e. nsP1234). "Transgene" in "cisReplicon Δ5ATG-RRS" corresponds to "Transgene 2" in "Δ5ATG-RRS-bicistronic". The functional alphavirus non-structural protein is capable of recognizing the subgenomic promoter and of synthesizing subgenomic transcripts comprising the nucleic acid sequence encoding the gene of interest ("Transgene"). "cisReplicon Δ5ATG-RRS" encodes a functional alphavirus non-structural protein in cis as does "cisReplicon WT-RRS"; however, it is not required that the coding sequence for nsP1 encoded by "cisReplicon Δ5ATG-RRS" comprises the exact nucleic acid sequence of "cisReplicon WT-RRS" including all stem loops.

Figure 6:
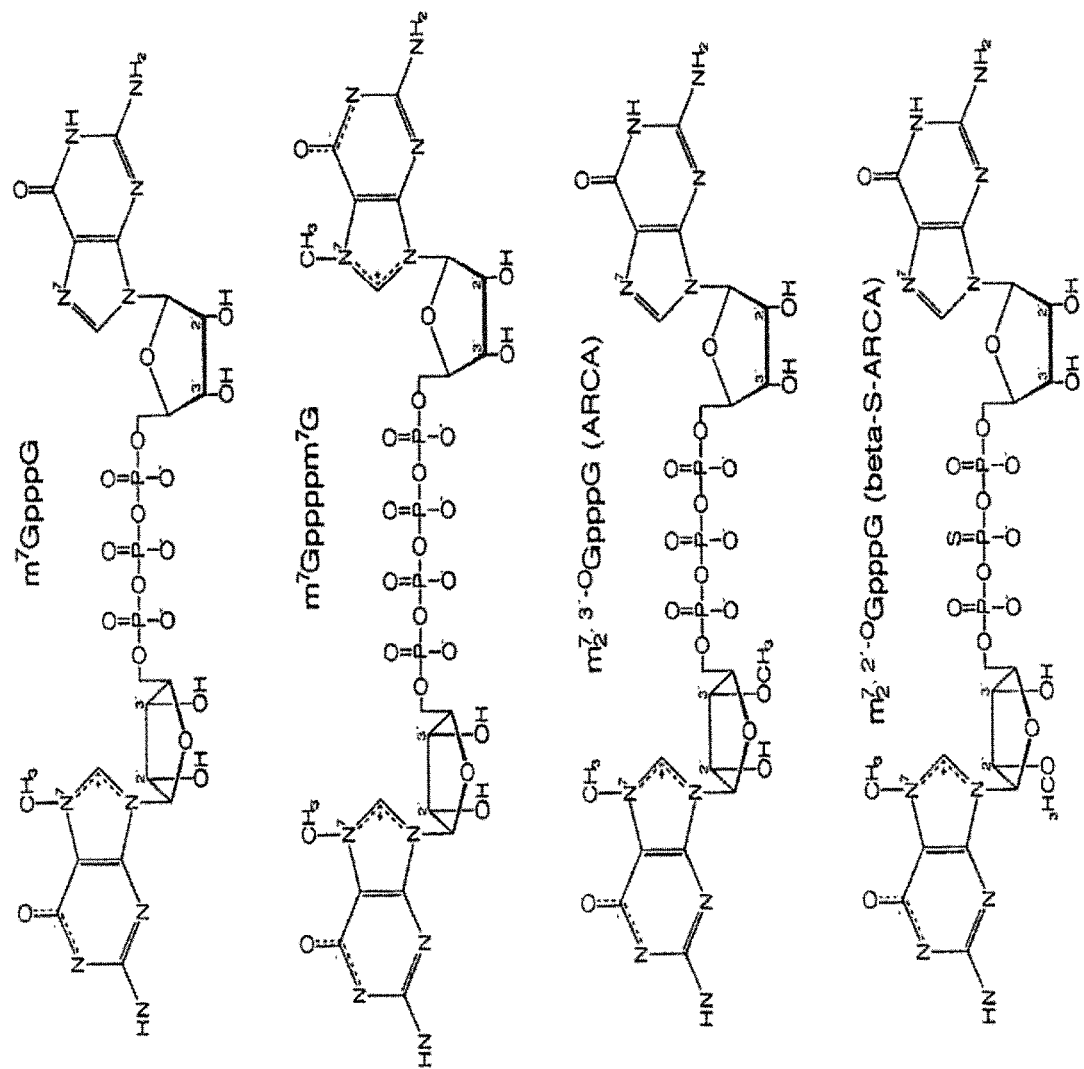

FIG. 6. Structures of cap dinucleotides. Top: a natural cap dinucleotide, m$^7$GpppG. Bottom: Phosphorothioate cap analog beta-S-ARCA dinucleotide: There are two diastereomers of beta-S-ARCA due to the stereogenic P center, which are designated D1 and D2 according to their elution characteristics in reverse phase HPLC.

DETAILED DESCRIPTION OF THE INVENTION

Although the present invention is described in detail below, it is to be understood that this invention is not limited to the particular methodologies, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

Preferably, the terms used herein are defined as described in "A multilingual glossary of biotechnological terms: (IUPAC Recommendations)", H. G. W. Leuenberger, B. Nagel, and H. Kölbl, Eds., Helvetica Chimica Acta, CH-4010 Basel, Switzerland, (1995).

The practice of the present invention will employ, unless otherwise indicated, conventional methods of chemistry, biochemistry, cell biology, immunology, and recombinant DNA techniques which are explained in the literature in the field (cf., e.g., Molecular Cloning: A Laboratory Manual, 2nd Edition, J. Sambrook et al. eds., Cold Spring Harbor Laboratory Press, Cold Spring Harbor 1989).

In the following, the elements of the present invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to disclose and encompass embodiments which combine the explicitly described embodiments with any number of the disclosed and/or preferred elements. Furthermore, any permutations and combinations of all described elements in this application should be considered disclosed by this description unless the context indicates otherwise.

The term "about" means approximately or nearly, and in the context of a numerical value or range set forth herein preferably means+/−10% of the numerical value or range recited or claimed.

The terms "a" and "an" and "the" and similar reference used in the context of describing the invention (especially in the context of the claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it was individually recited herein. All methods described herein can be performed in any suitable order unless otherwise indicated herein or otherwise clearly contradicted by context. The use of any and all examples, or exemplary language (e.g., "such as"), provided herein is intended merely to better illustrate the invention and does not pose a limitation on the scope of the invention otherwise claimed. No language in the specification should be construed as indicating any non-claimed element essential to the practice of the invention.

Unless expressly specified otherwise, the term "comprising" is used in the context of the present document to indicate that further members may optionally be present in addition to the members of the list introduced by "comprising". It is, however, contemplated as a specific embodiment of the present invention that the term "comprising" encompasses the possibility of no further members being present, i.e. for the purpose of this embodiment "comprising" is to be understood as having the meaning of "consisting of".

Indications of relative amounts of a component characterized by a generic term are meant to refer to the total amount of all specific variants or members covered by said generic term. If a certain component defined by a generic term is specified to be present in a certain relative amount, and if this component is further characterized to be a specific variant or member covered by the generic term, it is meant that no other variants or members covered by the generic term are additionally present such that the total relative amount of components covered by the generic term exceeds the specified relative amount; more preferably no other variants or members covered by the generic term are present at all.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the present invention was not entitled to antedate such disclosure.

Terms such as "reduce" or "inhibit" as used herein means the ability to cause an overall decrease, preferably of 5% or greater, 10% or greater, 20% or greater, more preferably of 50% or greater, and most preferably 75% or greater, in the level. The term "inhibit" or similar phrases includes a complete or essentially complete inhibition, i.e. a reduction to zero or essentially to zero.

Terms such as "increase" or "enhance" preferably relate to an increase or enhancement by about at least 10%, preferably at least 20%, preferably at least 30%, more preferably at least 40%, more preferably at least 50%, even more preferably at least 80%, and most preferably at least 100%.

The term "net charge" refers to the charge on a whole object, such as a compound or particle.

An ion having an overall net positive charge is a cation, while an ion having an overall net negative charge is an anion. Thus, according to the invention, an anion is an ion with more electrons than protons, giving it a net negative charge; and a cation is an ion with fewer electrons than protons, giving it a net positive charge.

Terms as "charged", "net charge", "negatively charged" or "positively charged", with reference to a given compound or particle, refer to the electric net charge of the given compound or particle when dissolved or suspended in water at pH 7.0.

According to the invention, a nucleic acid is a deoxyribonucleic acid (DNA) or a ribonucleic acid (RNA). In general, a nucleic acid molecule or a nucleic acid sequence refers to a nucleic acid which is preferably deoxyribonucleic acid (DNA) or ribonucleic acid (RNA). According to the invention, nucleic acids comprise genomic DNA, cDNA, mRNA, viral RNA, recombinantly prepared and chemically synthesized molecules. According to the invention, a nucleic acid may be in the form of a single-stranded or double-stranded and linear or covalently closed circular molecule. The term "nucleic acid" according to the invention also comprises a chemical derivatization of a nucleic acid on a nucleotide base, on the sugar or on the phosphate, and nucleic acids containing non-natural nucleotides and nucleotide analogs.

According to the invention "nucleic acid sequence" refers to the sequence of nucleotides in a nucleic acid, e.g. a ribonucleic acid (RNA) or a deoxyribonucleic acid (DNA). The term may refer to an entire nucleic acid molecule (such as to the single strand of an entire nucleic acid molecule) or to a part (e.g. a fragment) thereof.

According to the present invention, the term "RNA" or "RNA molecule" relates to a molecule which comprises ribonucleotide residues and which is preferably entirely or substantially composed of ribonucleotide residues. The term "ribonucleotide" relates to a nucleotide with a hydroxyl group at the 2'-position of a β-D-ribofuranosyl group. The term "RNA" comprises double-stranded RNA, single stranded RNA, isolated RNA such as partially or completely purified RNA, essentially pure RNA, synthetic RNA, and recombinantly generated RNA such as modified RNA which differs from naturally occurring RNA by addition, deletion, substitution and/or alteration of one or more nucleotides. Such alterations can include addition of non-nucleotide material, such as to the end(s) of a RNA or internally, for example at one or more nucleotides of the RNA. Nucleotides in RNA molecules can also comprise non-standard nucleotides, such as non-naturally occurring nucleotides or chemically synthesized nucleotides or deoxynucleotides. These altered RNAs can be referred to as analogs, particularly analogs of naturally occurring RNAs.

According to the invention, RNA may be single-stranded or double-stranded. In some embodiments of the present invention, single-stranded RNA is preferred. The term "single-stranded RNA" generally refers to an RNA molecule to which no complementary nucleic acid molecule (typically no complementary RNA molecule) is associated. Single-stranded RNA may contain self-complementary sequences that allow parts of the RNA to fold back and to form secondary structure motifs including without limitation base pairs, stems, stem loops and bulges. Single-stranded RNA can exist as minus strand [(−) strand] or as plus strand [(+) strand]. The (+) strand is the strand that comprises or encodes genetic information. The genetic information may be for example a polynucleotide sequence encoding a protein. When the (+) strand RNA encodes a protein, the (+) strand may serve directly as template for translation (protein synthesis). The (−) strand is the complement of the (+) strand. In the case of double-stranded RNA, (+) strand and (−) strand are two separate RNA molecules, and both these RNA molecules associate with each other to form a double-stranded RNA ("duplex RNA").

The term "stability" of RNA relates to the "half-life" of RNA. "Half-life" relates to the period of time which is needed to eliminate half of the activity, amount, or number of molecules. In the context of the present invention, the half-life of an RNA is indicative for the stability of said RNA. The half-life of RNA may influence the "duration of expression" of the RNA. It can be expected that RNA having a long half-life will be expressed for an extended time period.

The term "translation efficiency" relates to the amount of translation product provided by an RNA molecule within a particular period of time.

"Fragment", with reference to a nucleic acid sequence, relates to a part of a nucleic acid sequence, i.e. a sequence which represents the nucleic acid sequence shortened at the 5'- and/or 3'-end(s). Preferably, a fragment of a nucleic acid sequence comprises at least 80%, preferably at least 90%, 95%, 96%, 97%, 98%, or 99% of the nucleotide residues from said nucleic acid sequence. In the present invention those fragments of RNA molecules are preferred which retain RNA stability and/or translational efficiency.

"Fragment", with reference to an amino acid sequence (peptide or protein), relates to a part of an amino acid sequence, i.e. a sequence which represents the amino acid sequence shortened at the N-terminus and/or C-terminus. A fragment shortened at the C-terminus (N-terminal fragment) is obtainable e.g. by translation of a truncated open reading frame that lacks the 3'-end of the open reading frame. A fragment shortened at the N-terminus (C-terminal fragment) is obtainable e.g. by translation of a truncated open reading frame that lacks the 5'-end of the open reading frame, as long as the truncated open reading frame comprises a start codon that serves to initiate translation. A fragment of an amino acid sequence comprises e.g. at least 1%, at least 2%, at least 3%, at least 4%, at least 5%, at least 10%, at least 20%, at least 30%, at least 40%, at least 50%, at least 60%, at least 70%, at least 80%, at least 90% of the amino acid residues from an amino acid sequence.

The term "variant" with respect to, for example, nucleic acid and amino acid sequences, according to the invention includes any variants, in particular mutants, viral strain variants, splice variants, conformations, isoforms, allelic variants, species variants and species homologs, in particular those which are naturally present. An allelic variant relates to an alteration in the normal sequence of a gene, the significance of which is often unclear. Complete gene sequencing often identifies numerous allelic variants for a given gene. With respect to nucleic acid molecules, the term "variant" includes degenerate nucleic acid sequences, wherein a degenerate nucleic acid according to the invention is a nucleic acid that differs from a reference nucleic acid in codon sequence due to the degeneracy of the genetic code. A species homolog is a nucleic acid or amino acid sequence with a different species of origin from that of a given nucleic acid or amino acid sequence. A virus homolog is a nucleic acid or amino acid sequence with a different virus of origin from that of a given nucleic acid or amino acid sequence.

According to the invention, nucleic acid variants include single or multiple nucleotide deletions, additions, mutations, substitutions and/or insertions in comparison with the reference nucleic acid. Deletions include removal of one or more nucleotides from the reference nucleic acid. Addition variants comprise 5'- and/or 3'-terminal fusions of one or more nucleotides, such as 1, 2, 3, 5, 10, 20, 30, 50, or more nucleotides. In the case of substitutions, at least one nucleotide in the sequence is removed and at least one other nucleotide is inserted in its place (such as transversions and transitions). Mutations include abasic sites, crosslinked sites, and chemically altered or modified bases. Insertions include the addition of at least one nucleotide into the reference nucleic acid.

According to the invention, "nucleotide change" can refer to single or multiple nucleotide deletions, additions, mutations, substitutions and/or insertions in comparison with the reference nucleic acid. In some embodiments, a "nucleotide change" is selected from the group consisting of a deletion of a single nucleotide, the addition of a single nucleotide, the mutation of a single nucleotide, the substitution of a single nucleotide and/or the insertion of a single nucleotide, in comparison with the reference nucleic acid. According to the invention, a nucleic acid variant can comprise one or more nucleotide changes in comparison with the reference nucleic acid.

Variants of specific nucleic acid sequences preferably have at least one functional property of said specific sequences and preferably are functionally equivalent to said specific sequences, e.g. nucleic acid sequences exhibiting properties identical or similar to those of the specific nucleic acid sequences.

As described below, some embodiments of the present invention are characterized inter alia by nucleic acid sequences that are homologous to nucleic acid sequences of an alphavirus, such as an alphavirus found in nature. These homologous sequences are variants of nucleic acid sequences of an alphavirus, such as an alphavirus found in nature.

Preferably the degree of identity between a given nucleic acid sequence and a nucleic acid sequence which is a variant of said given nucleic acid sequence will be at least 70%, preferably at least 75%, preferably at least 80%, more preferably at least 85%, even more preferably at least 90% or most preferably at least 95%, 96%, 97%, 98% or 99%. The degree of identity is preferably given for a region of at least about 30, at least about 50, at least about 70, at least about 90, at least about 100, at least about 150, at least about 200, at least about 250, at least about 300, or at least about 400 nucleotides. In preferred embodiments, the degree of identity is given for the entire length of the reference nucleic acid sequence.

"Sequence similarity" indicates the percentage of amino acids that either are identical or that represent conservative amino acid substitutions. "Sequence identity" between two polypeptide or nucleic acid sequences indicates the percentage of amino acids or nucleotides that are identical between the sequences.

The term "% identical" is intended to refer, in particular, to a percentage of nucleotides which are identical in an optimal alignment between two sequences to be compared, with said percentage being purely statistical, and the differences between the two sequences may be randomly distributed over the entire length of the sequence and the sequence to be compared may comprise additions or deletions in comparison with the reference sequence, in order to obtain optimal alignment between two sequences. Comparisons of two sequences are usually carried out by comparing said sequences, after optimal alignment, with respect to a segment or "window of comparison", in order to identify local regions of corresponding sequences. The optimal alignment for a comparison may be carried out manually or with the aid of the local homology algorithm by Smith and Waterman, 1981, Ads App. Math. 2, 482, with the aid of the local homology algorithm by Needleman and Wunsch, 1970, J. Mol. Biol. 48, 443, and with the aid of the similarity search algorithm by Pearson and Lipman, 1988, Proc. Natl Acad. Sci. USA 85, 2444 or with the aid of computer programs using said algorithms (GAP, BESTFIT, FASTA, BLAST P, BLAST N and TFASTA in Wisconsin Genetics Software Package, Genetics Computer Group, 575 Science Drive, Madison, Wis.).

Percentage identity is obtained by determining the number of identical positions in which the sequences to be compared correspond, dividing this number by the number of positions compared and multiplying this result by 100.

For example, the BLAST program "BLAST 2 sequences" which is available on the website http://www.ncbi.nlm.nih.gov/blast/bl2seq/wblast2.cgi may be used.

A nucleic acid is "capable of hybridizing" or "hybridizes" to another nucleic acid if the two sequences are complementary with one another. A nucleic acid is "complementary" to another nucleic acid if the two sequences are capable of forming a stable duplex with one another. According to the invention, hybridization is preferably carried out under conditions which allow specific hybridization between polynucleotides (stringent conditions). Stringent conditions are described, for example, in Molecular Cloning: A Laboratory Manual, J. Sambrook et al., Editors, 2$^{nd}$ Edition, Cold Spring Harbor Laboratory press, Cold Spring Harbor, New York, 1989 or Current Protocols in Molecular Biology, F. M. Ausubel et al., Editors, John Wiley & Sons, Inc., New York and refer, for example, to hybridization at 65° C. in hybridization buffer (3.5×SSC, 0.02% Ficoll, 0.02% polyvinylpyrrolidone, 0.02% bovine serum albumin, 2.5 mM NaH$_2$PO$_4$ (pH 7), 0.5% SDS, 2 mM EDTA). SSC is 0.15 M sodium chloride/0.15 M sodium citrate, pH 7. After hybridization, the membrane to which the DNA has been transferred is washed, for example, in 2×SSC at room temperature and then in 0.1-0.5×SSC/0.1×SDS at temperatures of up to 68° C.

A percent complementarity indicates the percentage of contiguous residues in a nucleic acid molecule that can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" or "fully complementary" means that all the contiguous residues of a nucleic acid sequence will hydrogen bond with the same number of contiguous residues in a second nucleic acid sequence. Preferably, the degree of complementarity according to the invention is at least 70%, preferably at least 75%, preferably at least 80%, more preferably at least 85%, even more preferably at least 90% or most preferably at least 95%, 96%, 97%, 98% or 99%. Most preferably, the degree of complementarity according to the invention is 100%.

The term "derivative" comprises any chemical derivatization of a nucleic acid on a nucleotide base, on the sugar or on the phosphate. The term "derivative" also comprises nucleic acids which contain nucleotides and nucleotide analogs not occurring naturally. Preferably, a derivatization of a nucleic acid increases its stability.

According to the invention, a "nucleic acid sequence which is derived from a nucleic acid sequence" refers to a nucleic acid which is a variant of the nucleic acid from which it is derived. Preferably, a sequence which is a variant with respect to a specific sequence, when it replaces the specific sequence in an RNA molecule retains RNA stability and/or translational efficiency.

"nt" is an abbreviation for nucleotide; or for nucleotides, preferably consecutive nucleotides in a nucleic acid molecule.

According to the invention, the term "codon" refers to a base triplet in a coding nucleic acid that specifies which amino acid will be added next during protein synthesis at the ribosome.

The terms "transcription" and "transcribing" relate to a process during which a nucleic acid molecule with a particular nucleic acid sequence (the "nucleic acid template") is read by an RNA polymerase so that the RNA polymerase produces a single-stranded RNA molecule. During transcription, the genetic information in a nucleic acid template is transcribed. The nucleic acid template may be DNA; however, e.g. in the case of transcription from an alphaviral nucleic acid template, the template is typically RNA. Subsequently, the transcribed RNA may be translated into protein. According to the present invention, the term "transcription" comprises "in vitro transcription", wherein the term "in vitro transcription" relates to a process wherein RNA, in particular mRNA, is in vitro synthesized in a cell-free system. Preferably, cloning vectors are applied for the generation of transcripts. These cloning vectors are generally designated as transcription vectors and are according to the present invention encompassed by the term "vector". The cloning vectors are preferably plasmids. According to the present invention, RNA preferably is in vitro transcribed RNA (IVT-RNA) and may be obtained by in vitro transcription of an appropriate DNA template. The promoter for controlling transcription can be any promoter for any RNA polymerase. A DNA template for in vitro transcription may be obtained by cloning of a nucleic acid, in particular cDNA, and introducing it into an appropriate vector for in vitro transcription. The cDNA may be obtained by reverse transcription of RNA.

The single-stranded nucleic acid molecule produced during transcription typically has a nucleic acid sequence that is the complementary sequence of the template.

According to the invention, the terms "template" or "nucleic acid template" or "template nucleic acid" generally refer to a nucleic acid sequence that may be replicated or transcribed.

"Nucleic acid sequence transcribed from a nucleic acid sequence" and similar terms refer to a nucleic acid sequence, where appropriate as part of a complete RNA molecule, which is a transcription product of a template nucleic acid sequence. Typically, the transcribed nucleic acid sequence is a single-stranded RNA molecule.

"3' end of a nucleic acid" refers according to the invention to that end which has a free hydroxy group. In a diagrammatic representation of double-stranded nucleic acids, in particular DNA, the 3' end is always on the right-hand side. "5' end of a nucleic acid" refers according to the invention to that end which has a free phosphate group. In a diagrammatic representation of double-strand nucleic acids, in particular DNA, the 5' end is always on the left-hand side.

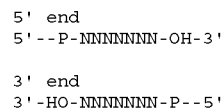

```
5' end
5'--P-NNNNNNNN-OH-3'

3' end
3'-HO-NNNNNNNN-P--5'
```

"Upstream" describes the relative positioning of a first element of a nucleic acid molecule with respect to a second element of that nucleic acid molecule, wherein both elements are comprised in the same nucleic acid molecule, and wherein the first element is located nearer to the 5' end of the nucleic acid molecule than the second element of that nucleic acid molecule. The second element is then said to be "downstream" of the first element of that nucleic acid molecule. An element that is located "upstream" of a second element can be synonymously referred to as being located "5'" of that second element. For a double-stranded nucleic acid molecule, indications like "upstream" and "downstream" are given with respect to the (+) strand.

According to the invention, "functional linkage" or "functionally linked" relates to a connection within a functional relationship. A nucleic acid is "functionally linked" if it is functionally related to another nucleic acid sequence. For example, a promoter is functionally linked to a coding sequence if it influences transcription of said coding sequence. Functionally linked nucleic acids are typically adjacent to one another, where appropriate separated by further nucleic acid sequences, and, in particular embodiments, are transcribed by RNA polymerase to give a single RNA molecule (common transcript).

In particular embodiments, a nucleic acid is functionally linked according to the invention to expression control sequences which may be homologous or heterologous with respect to the nucleic acid.

The term "expression control sequence" comprises according to the invention promoters, ribosome-binding sequences and other control elements which control transcription of a gene or translation of the derived RNA. In particular embodiments of the invention, the expression control sequences can be regulated. The precise structure of expression control sequences may vary depending on the species or cell type but usually includes 5'-untranscribed and 5'- and 3'-untranslated sequences involved in initiating transcription and translation, respectively. More specifically, 5'-untranscribed expression control sequences include a promoter region which encompasses a promoter sequence for transcription control of the functionally linked gene. Expression control sequences may also include enhancer sequences or upstream activator sequences. An expression control sequence of a DNA molecule usually includes 5'-untranscribed and 5'- and 3'-untranslated sequences such as TATA box, capping sequence, CAAT sequence and the like. An expression control sequence of alphaviral RNA may include a subgenomic promoter and/or one or more conserved sequence element(s). A specific expression control sequence according to the present invention is a subgenomic promoter of an alphavirus, as described herein.

The nucleic acid sequences specified herein, in particular transcribable and coding nucleic acid sequences, may be combined with any expression control sequences, in particular promoters, which may be homologous or heterologous to said nucleic acid sequences, with the term "homologous" referring to the fact that a nucleic acid sequence is also functionally linked naturally to the expression control sequence, and the term "heterologous" referring to the fact that a nucleic acid sequence is not naturally functionally linked to the expression control sequence.

A transcribable nucleic acid sequence, in particular a nucleic acid sequence coding for a peptide or protein, and an expression control sequence are "functionally" linked to one another, if they are covalently linked to one another in such a way that transcription or expression of the transcribable and in particular coding nucleic acid sequence is under the control or under the influence of the expression control sequence. If the nucleic acid sequence is to be translated into a functional peptide or protein, induction of an expression control sequence functionally linked to the coding sequence results in transcription of said coding sequence, without causing a frame shift in the coding sequence or the coding sequence being unable to be translated into the desired peptide or protein.

The term "promoter" or "promoter region" refers to a nucleic acid sequence which controls synthesis of a transcript, e.g. a transcript comprising a coding sequence, by providing a recognition and binding site for RNA polymerase. The promoter region may include further recognition or binding sites for further factors involved in regulating transcription of said gene. A promoter may control transcription of a prokaryotic or eukaryotic gene. A promoter may be "inducible" and initiate transcription in response to an inducer, or may be "constitutive" if transcription is not controlled by an inducer. An inducible promoter is expressed only to a very small extent or not at all, if an inducer is absent. In the presence of the inducer, the gene is "switched on" or the level of transcription is increased. This is usually mediated by binding of a specific transcription factor. A specific promoter according to the present invention is a subgenomic promoter of an alphavirus, as described herein. Other specific promoters are genomic plus-strand or negative-strand promoters of an alphavirus.

The term "core promoter" refers to a nucleic acid sequence that is comprised by the promoter. The core promoter is typically the minimal portion of the promoter required to properly initiate transcription. The core promoter typically includes the transcription start site and a binding site for RNA polymerase.

A "polymerase" generally refers to a molecular entity capable of catalyzing the synthesis of a polymeric molecule from monomeric building blocks. A "RNA polymerase" is a molecular entity capable of catalyzing the synthesis of a RNA molecule from ribonucleotide building blocks. A "DNA polymerase" is a molecular entity capable of catalyzing the synthesis of a DNA molecule from deoxy ribonucleotide building blocks. For the case of DNA polymerases and RNA polymerases, the molecular entity is typically a protein or an assembly or complex of multiple proteins. Typically, a DNA polymerase synthesizes a DNA molecule based on a template nucleic acid, which is typically a DNA molecule. Typically, a RNA polymerase synthesizes a RNA molecule based on a template nucleic acid, which is either a DNA molecule (in that case the RNA polymerase is a DNA-dependent RNA polymerase, DdRP), or is a RNA molecule (in that case the RNA polymerase is a RNA-dependent RNA polymerase, RdRP).

A "RNA-dependent RNA polymerase" or "RdRP", is an enzyme that catalyzes the transcription of RNA from an RNA template. In the case of alphaviral RNA-dependent RNA polymerase, sequential synthesis of (−) strand complement of genomic RNA and of (+) strand genomic RNA leads to RNA replication. Alphaviral RNA-dependent RNA polymerase is thus synonymously referred to as "RNA replicase". In nature, RNA-dependent RNA polymerases are typically encoded by all RNA viruses except retroviruses. Typical representatives of viruses encoding a RNA-dependent RNA polymerase are alphaviruses.

According to the present invention, "RNA replication" generally refers to an RNA molecule synthesized based on the nucleotide sequence of a given RNA molecule (template RNA molecule). The RNA molecule that is synthesized may be e.g. identical or complementary to the template RNA molecule. In general, RNA replication may occur via synthesis of a DNA intermediate, or may occur directly by RNA-dependent RNA replication mediated by a RNA-dependent RNA polymerase (RdRP). In the case of alphaviruses, RNA replication does not occur via a DNA intermediate, but is mediated by a RNA-dependent RNA polymerase (RdRP): a template RNA strand (first RNA strand)—or a part thereof—serves as template for the synthesis of a second RNA strand that is complementary to the first RNA strand or to a part thereof. The second RNA strand—or a part thereof—may in turn optionally serve as a template for synthesis of a third RNA strand that is complementary to the second RNA strand or to a part thereof. Thereby, the third RNA strand is identical to the first RNA strand or to a part thereof. Thus, RNA-dependent RNA polymerase is capable of directly synthesizing a complementary RNA strand of a template, and of indirectly synthesizing an identical RNA strand (via a complementary intermediate strand).

According to the invention, the term "template RNA" refers to RNA that can be transcribed or replicated by an RNA-dependent RNA polymerase.

According to the invention, the term "gene" refers to a particular nucleic acid sequence which is responsible for producing one or more cellular products and/or for achieving one or more intercellular or intracellular functions. More specifically, said term relates to a nucleic acid section (typically DNA; but RNA in the case of RNA viruses) which comprises a nucleic acid coding for a specific protein or a functional or structural RNA molecule.

An "isolated molecule" as used herein, is intended to refer to a molecule which is substantially free of other molecules such as other cellular material. The term "isolated nucleic acid" means according to the invention that the nucleic acid has been (i) amplified in vitro, for example by polymerase chain reaction (PCR), (ii) recombinantly produced by cloning, (iii) purified, for example by cleavage and gel-electrophoretic fractionation, or (iv) synthesized, for example by chemical synthesis. An isolated nucleic acid is a nucleic acid available to manipulation by recombinant techniques.

The term "vector" is used here in its most general meaning and comprises any intermediate vehicles for a nucleic acid which, for example, enable said nucleic acid to be introduced into prokaryotic and/or eukaryotic host cells and, where appropriate, to be integrated into a genome. Such vectors are preferably replicated and/or expressed in the cell. Vectors comprise plasmids, phagemids, virus genomes, and fractions thereof.

The term "recombinant" in the context of the present invention means "made through genetic engineering". Preferably, a "recombinant object" such as a recombinant cell in the context of the present invention is not occurring naturally.

The term "naturally occurring" as used herein refers to the fact that an object can be found in nature. For example, a peptide or nucleic acid that is present in an organism (including viruses) and can be isolated from a source in nature and which has not been intentionally modified by man in the laboratory is naturally occurring. The term "found in nature" means "present in nature" and includes known objects as well as objects that have not yet been discovered and/or isolated from nature, but that may be discovered and/or isolated in the future from a natural source.

According to the invention, the term "expression" is used in its most general meaning and comprises production of RNA, or of RNA and protein. It also comprises partial expression of nucleic acids. Furthermore, expression may be transient or stable. With respect to RNA, the term "expression" or "translation" relates to the process in the ribosomes of a cell by which a strand of coding RNA (e.g. messenger RNA) directs the assembly of a sequence of amino acids to make a peptide or protein.

According to the invention, the term "mRNA" means "messenger-RNA" and relates to a transcript which is typically generated by using a DNA template and encodes a peptide or protein. Typically, mRNA comprises a 5'-UTR, a protein coding region, a 3'-UTR, and a poly(A) sequence. mRNA may be generated by in vitro transcription from a DNA template. The in vitro transcription methodology is known to the skilled person. For example, there is a variety of in vitro transcription kits commercially available. According to the invention, mRNA may be modified by stabilizing modifications and capping.

According to the invention, the terms "poly(A) sequence" or "poly(A) tail" refer to an uninterrupted or interrupted sequence of adenylate residues which is typically located at the 3' end of an RNA molecule. An uninterrupted sequence is characterized by consecutive adenylate residues. In nature, an uninterrupted poly(A) sequence is typical. While a poly(A) sequence is normally not encoded in eukaryotic DNA, but is attached during eukaryotic transcription in the cell nucleus to the free 3' end of the RNA by a template-independent RNA polymerase after transcription, the present invention encompasses poly(A) sequences encoded by DNA.

According to the invention, the term "primary structure", with reference to a nucleic acid molecule, refers to the linear sequence of nucleotide monomers.

According to the invention, the term "secondary structure", with reference to a nucleic acid molecule, refers to a two-dimensional representation of a nucleic acid molecule that reflects base pairings; e.g. in the case of a single-stranded RNA molecule particularly intramolecular base pairings. Although each RNA molecule has only a single polynucleotide chain, the molecule is typically characterized by regions of (intramolecular) base pairs. According to the invention, the term "secondary structure" comprises structural motifs including without limitation base pairs, stems, stem loops, bulges, loops such as interior loops and multi-branch loops. The secondary structure of a nucleic acid molecule can be represented by a two-dimensional drawing (planar graph), showing base pairings (for further details on secondary structure of RNA molecules, see Auber et al., J. Graph Algorithms Appl., 2006, vol. 10, pp. 329-351). As described herein, the secondary structure of certain RNA molecules is relevant in the context of the present invention.

According to the invention, secondary structure of a nucleic acid molecule, particularly of a single-stranded RNA molecule, is determined by prediction using the web server for RNA secondary structure prediction (http://rna.urmc.rochester.edu/RNAstructureWeb/Servers/Predict1/Predict1.html). Preferably, according to the invention, "secondary structure", with reference to a nucleic acid molecule, specifically refers to the secondary structure determined by said prediction. The prediction may also be performed or confirmed using MFOLD structure prediction (http://unafold.rna.albany.edu/?q=mfold).

According to the invention, a "base pair" is a structural motif of a secondary structure wherein two nucleotide bases associate with each other through hydrogen bonds between donor and acceptor sites on the bases. The complementary bases, A:U and G:C, form stable base pairs through hydrogen bonds between donor and acceptor sites on the bases; the A:U and G:C base pairs are called Watson-Crick base pairs. A weaker base pair (called Wobble base pair) is formed by the bases G and U (G:U). The base pairs A:U and G:C are called canonical base pairs. Other base pairs like G:U (which occurs fairly often in RNA) and other rare base-pairs (e.g. A:C; U:U) are called non-canonical base pairs.

According to the invention, "nucleotide pairing" refers to two nucleotides that associate with each other so that their bases form a base pair (canonical or non-canonical base pair, preferably canonical base pair, most preferably Watson-Crick base pair).

According to the invention, the terms "stem loop" or "hairpin" or "hairpin loop", with reference to a nucleic acid molecule, all interchangeably refer to a particular secondary structure of a nucleic acid molecule, typically a single-stranded nucleic acid molecule, such as single-stranded RNA. The particular secondary structure represented by the stem loop consists of a consecutive nucleic acid sequence comprising a stem and a (terminal) loop, also called hairpin loop, wherein the stem is formed by two neighbored entirely or partially complementary sequence elements which are separated by a short sequence (e.g. 3-10 nucleotides), which forms the loop of the stem-loop structure. The two neighbored entirely or partially complementary sequences may be defined as e.g. stem loop elements stem 1 and stem 2. The stem loop is formed when these two neighbored entirely or partially reverse complementary sequences, e.g. stem loop elements stem 1 and stem 2, form base-pairs with each other, leading to a double stranded nucleic acid sequence comprising an unpaired loop at its terminal ending formed by the short sequence located between stem loop elements stem 1 and stem 2. Thus, a stem loop comprises two stems (stem 1 and stem 2), which—at the level of secondary structure of the nucleic acid molecule—form base pairs with each other, and which—at the level of the primary structure of the nucleic acid molecule—are separated by a short sequence that is not part of stem 1 or stem 2. For illustration, a two-dimensional representation of the stem loop resembles a lollipop-shaped structure. The formation of a stem-loop structure requires the presence of a sequence that can fold back on itself to form a paired double strand; the paired double strand is formed by stem 1 and stem 2. The stability of paired stem loop elements is typically determined by the length, the number of nucleotides of stem 1 that are capable of forming base pairs (preferably canonical base pairs, more preferably Watson-Crick base pairs) with nucleotides of stem 2, versus the number of nucleotides of stem 1 that are not capable of forming such base pairs with nucleotides of stem 2 (mismatches or bulges). According to the present invention, the optimal loop length is 3-10 nucleotides, more preferably 4 to 7 nucleotides, such as 4 nucleotides, 5 nucleotides, 6 nucleotides or 7 nucleotides. If a given nucleic acid sequence is characterized by a stem loop, the respective complementary nucleic acid sequence is typically also characterized by a stem loop. A stem loop is typically formed by single-stranded RNA molecules. For example, several stem loops are present in the 5' replication recognition sequence of alphaviral genomic RNA (illustrated in FIG. 5).

According to the invention, "disruption" or "disrupt", with reference to a specific secondary structure of a nucleic acid molecule (e.g. a stem loop) means that the specific secondary structure is absent or altered. Typically, a secondary structure may be disrupted as a consequence of a change of at least one nucleotide that is part of the secondary structure. For example, a stem loop may be disrupted by change of one or more nucleotides that form the stem, so that nucleotide pairing is not possible.

According to the invention, "compensates for secondary structure disruption" or "compensating for secondary structure disruption" refers to one or more nucleotide changes in a nucleic acid sequence; more typically it refers to one or more second nucleotide changes in a nucleic acid sequence, which nucleic acid sequence also comprises one or more first nucleotide changes, characterized as follows: while the one or more first nucleotide changes, in the absence of the one or more second nucleotide changes, cause a disruption of the secondary structure of the nucleic acid sequence, the co-occurrence of the one or more first nucleotide changes and the one or more second nucleotide changes does not cause the secondary structure of the nucleic acid to be disrupted. Co-occurrence means presence of both the one or more first nucleotide changes and of the one or more second nucleotide changes. Typically, the one or more first nucleotide changes and the one or more second nucleotide changes are present together in the same nucleic acid molecule. In a specific embodiment, one or more nucleotide changes that compensate for secondary structure disruption is/are one or more nucleotide changes that compensate for one or more nucleotide pairing disruptions. Thus, in one embodiment, "compensating for secondary structure disruption" means "compensating for nucleotide pairing disruptions", i.e. one or more nucleotide pairing disruptions, for example one or more nucleotide pairing disruptions within one or more stem loops. The one or more one or more nucleotide pairing disruptions may have been introduced by the removal of at least one initiation codon. Each of the one or more nucleotide changes that compensates for secondary structure disruption is a nucleotide change, which can each be independently selected from a deletion, an addition, a substitution and/or an insertion of one or more nucleotides. In an illustrative example, when the nucleotide pairing A:U has been disrupted by substitution of A to C (C and U are not typically suitable to form a nucleotide pair); then a nucleotide change that compensates for nucleotide pairing disruption may be substitution of U by G, thereby enabling formation of the C:G nucleotide pairing. The substitution of U by G thus compensates for the nucleotide pairing disruption. In an alternative example, when the nucleotide pairing A:U has been disrupted by substitution of A to C; then a nucleotide change that compensates for nucleotide pairing disruption may be substitution of C by A, thereby restoring formation of the original A:U nucleotide pairing. In general, in the present invention, those nucleotide changes compensating for secondary structure disruption are preferred which do neither restore the original nucleic acid sequence nor create novel AUG triplets. In the above set of examples, the U to G substitution is preferred over the C to A substitution.

According to the invention, the term "tertiary structure", with reference to a nucleic acid molecule, refers to the three dimensional structure of a nucleic acid molecule, as defined by the atomic coordinates.

According to the invention, a nucleic acid such as RNA, e.g. mRNA, may encode a peptide or protein. Accordingly, a transcribable nucleic acid sequence or a transcript thereof may contain an open reading frame (ORF) encoding a peptide or protein.

According to the invention, the term "nucleic acid encoding a peptide or protein" means that the nucleic acid, if present in the appropriate environment, preferably within a cell, can direct the assembly of amino acids to produce the peptide or protein during the process of translation. Preferably, coding RNA according to the invention is able to interact with the cellular translation machinery allowing translation of the coding RNA to yield a peptide or protein.

According to the invention, the term "peptide" comprises oligo- and polypeptides and refers to substances which comprise two or more, preferably 3 or more, preferably 4 or more, preferably 6 or more, preferably 8 or more, preferably 10 or more, preferably 13 or more, preferably 16 or more, preferably 20 or more, and up to preferably 50, preferably 100 or preferably 150, consecutive amino acids linked to one another via peptide bonds. The term "protein" refers to large peptides, preferably peptides having at least 151 amino acids, but the terms "peptide" and "protein" are used herein usually as synonyms.

The terms "peptide" and "protein" comprise, according to the invention, substances which contain not only amino acid components but also non-amino acid components such as sugars and phosphate structures, and also comprise substances containing bonds such as ester, thioether or disulfide bonds.

According to the invention, the terms "initiation codon" and "start codon" synonymously refer to a codon (base triplet) of a RNA molecule that is potentially the first codon that is translated by a ribosome. Such codon typically encodes the amino acid methionine in eukaryotes and a modified methionine in prokaryotes. The most common initiation codon in eukaryotes and prokaryotes is AUG. Unless specifically stated herein that an initiation codon other than AUG is meant, the terms "initiation codon" and "start codon", with reference to an RNA molecule, refer to the codon AUG. According to the invention, the terms "initiation codon" and "start codon" are also used to refer to a corresponding base triplet of a deoxyribonucleic acid, namely the base triplet encoding the initiation codon of a RNA. If the initiation codon of messenger RNA is AUG, the base triplet encoding the AUG is ATG. According to the invention, the terms "initiation codon" and "start codon" preferably refer to a functional initiation codon or start codon, i.e. to an initiation codon or start codon that is used or would be used as a codon by a ribosome to start translation. There may be AUG codons in an RNA molecule that are not used as codons by a ribosome to start translation, e.g. due to a short distance of the codons to the cap. These codons are not encompassed by the term functional initiation codon or start codon.

According to the invention, the terms "start codon of the open reading frame" or "initiation codon of the open reading frame" refer to the base triplet that serves as initiation codon for protein synthesis in a coding sequence, e.g. in the coding sequence of a nucleic acid molecule found in nature. In an RNA molecule, the start codon of the open reading frame is often preceded by a 5' untranslated region (5'-UTR), although this is not strictly required.

According to the invention, the terms "native start codon of the open reading frame" or "native initiation codon of the open reading frame" refer to the base triplet that serves as initiation codon for protein synthesis in a native coding sequence. A native coding sequence may be e.g. the coding sequence of a nucleic acid molecule found in nature. In some embodiments, the present invention provides variants of nucleic acid molecules found in nature, which are characterized in that the native start codon (which is present in the native coding sequence) has been removed (so that it is not present in the variant nucleic acid molecule).

According to the invention, "first AUG" means the most upstream AUG base triplet of a messenger RNA molecule, preferably the most upstream AUG base triplet of a messenger RNA molecule that is used or would be used as a codon by a ribosome to start translation. Accordingly, "first ATG" refers to the ATG base triplet of a coding DNA sequence that encodes the first AUG. In some instances, the first AUG of a mRNA molecule is the start codon of an open reading frame, i.e. the codon that is used as start codon during ribosomal protein synthesis.

According to the invention, the terms "comprises the removal" or "characterized by the removal" and similar terms, with reference to a certain element of a nucleic acid variant, mean that said certain element is not functional or not present in the nucleic acid variant, compared to a reference nucleic acid molecule. Without limitation, a removal can consist of deletion of all or part of the certain element, of substitution of all or part of the certain element, or of alteration of the functional or structural properties of the certain element. The removal of a functional element of a nucleic acid sequence requires that the function is not exhibited at the position of the nucleic acid variant comprising the removal. For example, a RNA variant characterized by the removal of a certain initiation codon requires that ribosomal protein synthesis is not initiated at the position of the RNA variant characterized by the removal. The removal of a structural element of a nucleic acid sequence requires that the structural element is not present at the position of the nucleic acid variant comprising the removal. For example, a RNA variant characterized by the removal of a certain AUG base triplet, i.e. of a AUG base triplet at a certain position, may be characterized, e.g. by deletion of part or all of the certain AUG base triplet (e.g. ΔAUG), or by substitution of one or more nucleotides (A, U, G) of the certain AUG base triplet by any one or more different nucleotides, so that the resulting nucleotide sequence of the variant does not comprise said AUG base triplet. Suitable substitutions of one nucleotide are those that convert the AUG base triplet into a GUG, CUG or UUG base triplet, or into a AAG, ACG or AGG base triplet, or into a AUA, AUC or AUU base triplet. Suitable substitutions of more nucleotides can be selected accordingly.

According to the invention, the term "alphavirus" is to be understood broadly and includes any virus particle that has characteristics of alphaviruses. Characteristics of alphavirus include the presence of a (+) stranded RNA which encodes genetic information suitable for replication in a host cell, including RNA polymerase activity. Further characteristics of many alphaviruses are described e.g. in Strauss & Strauss, Microbiol. Rev., 1994, vol. 58, pp. 491-562. The term "alphavirus" includes alphavirus found in nature, as well as any variant or derivative thereof. In some embodiments, a variant or derivative is not found in nature.

In one embodiment, the alphavirus is an alphavirus found in nature. Typically, an alphavirus found in nature is infectious to any one or more eukaryotic organisms, such as an animal (including a vertebrate such as a human, and an arthropod such as an insect).

An alphavirus found in nature is preferably selected from the group consisting of the following: Barmah Forest virus complex (comprising Barmah Forest virus); Eastern equine encephalitis complex (comprising seven antigenic types of Eastern equine encephalitis virus); Middelburg virus complex (comprising Middelburg virus); Ndumu virus complex (comprising Ndumu virus); Semliki Forest virus complex (comprising Bebaru virus, Chikungunya virus, Mayaro virus and its subtype Una virus, O'Nyong Nyong virus, and its subtype lgbo-Ora virus, Ross River virus and its subtypes Bebaru virus, Getah virus, Sagiyama virus, Semliki Forest virus and its subtype Me Tri virus); Venezuelan equine encephalitis complex (comprising Cabassou virus, Everglades virus, Mosso das Pedras virus, Mucambo virus, Paramana virus, Pixuna virus, Rio Negro virus, Trocara virus and its subtype Bijou Bridge virus, Venezuelan equine encephalitis virus); Western equine encephalitis complex (comprising Aura virus, Babanki virus, Kyzylagach virus, Sindbis virus, Ockelbo virus, Whataroa virus, Buggy Creek virus, Fort Morgan virus, Highlands J virus, Western equine encephalitis virus); and some unclassified viruses including Salmon pancreatic disease virus; Sleeping Disease virus; Southern elephant seal virus; Tonate virus. More preferably, the alphavirus is selected from the group consisting of Semliki Forest virus complex (comprising the virus types as indicated above, including Semliki Forest virus), Western equine encephalitis complex (comprising the virus types as indicated above, including Sindbis virus), Eastern equine encephalitis virus (comprising the virus types as indicated above), Venezuelan equine encephalitis complex (comprising the virus types as indicated above, including Venezuelan equine encephalitis virus).

In a further preferred embodiment, the alphavirus is Semliki Forest virus. In an alternative further preferred embodiment, the alphavirus is Sindbis virus. In an alternative further preferred embodiment, the alphavirus is Venezuelan equine encephalitis virus.

In some embodiments of the present invention, the alphavirus is not an alphavirus found in nature. Typically, an alphavirus not found in nature is a variant or derivative of an alphavirus found in nature, that is distinguished from an alphavirus found in nature by at least one mutation in the nucleotide sequence, i.e. the genomic RNA. The mutation in the nucleotide sequence may be selected from an insertion, a substitution or a deletion of one or more nucleotides, compared to an alphavirus found in nature. A mutation in the nucleotide sequence may or may not be associated with a mutation in a polypeptide or protein encoded by the nucleotide sequence. For example, an alphavirus not found in nature may be an attenuated alphavirus. An attenuated alphavirus not found in nature is an alphavirus that typically has at least one mutation in its nucleotide sequence by which it is distinguished from an alphavirus found in nature, and that is either not infectious at all, or that is infectious but has a lower disease-producing ability or no disease-producing ability at all. As an illustrative example, TC83 is an attenuated alphavirus that is distinguished from the Venezuelan equine encephalitis virus (VEEV) found in nature (McKinney et al., 1963, Am. J. Trop. Med. Hyg., 1963, vol. 12; pp. 597-603).

Members of the alphavirus genus may also be classified based on their relative clinical features in humans: alphaviruses associated primarily with encephalitis, and alphaviruses associated primarily with fever, rash, and polyarthritis.

The term "alphaviral" means found in an alphavirus, or originating from an alphavirus or derived from an alphavirus, e.g. by genetic engineering.

According to the invention, "SFV" stands for Semliki Forest virus. According to the invention, "SIN" or "SINV" stands for Sindbis virus. According to the invention, "VEE" or "VEEV" stands for Venezuelan equine encephalitis virus.

According to the invention, the term "of an aiphavirus" refers to an entity of origin from an aiphavirus. For illustration, a protein of an aiphavirus may refer to a protein that is found in alphavirus and/or to a protein that is encoded by aiphavirus; and a nucleic acid sequence of an alphavirus may refer to a nucleic acid sequence that is found in alphavirus and/or to a nucleic acid sequence that is encoded by alphavirus. Preferably, a nucleic acid sequence "of an alphavirus" refers to a nucleic acid sequence "of the genome of an aiphavirus" and/or "of genomic RNA of an alphavirus".

According to the invention, the term "alphaviral RNA" refers to any one or more of alphaviral genomic RNA (i.e. (+) strand), complement of alphaviral genomic RNA (i.e. (−) strand), and the subgenomic transcript (i.e. (+) strand), or a fragment of any thereof.

According to the invention, "alphavirus genome" refers to genomic (+) strand RNA of an alphavirus.

According to the invention, the term "native alphavirus sequence" and similar terms typically refer to a (e.g. nucleic acid) sequence of a naturally occurring alphavirus (alphavirus found in nature). In some embodiments, the term "native alphavirus sequence" also includes a sequence of an attenuated aiphavirus.

According to the invention, the term "5' replication recognition sequence" preferably refers to a continuous nucleic acid sequence, preferably a ribonucleic acid sequence, that is identical or homologous to a 5' fragment of the alphavirus genome. The "5' replication recognition sequence" is a nucleic acid sequence that can be recognized by an alphaviral replicase. The term 5' replication recognition sequence includes native 5' replication recognition sequences as well as functional equivalents thereof, such as, e.g., functional variants of a 5' replication recognition sequence of alphavirus found in nature. According to the invention, functional equivalents include derivatives of 5' replication recognition sequences characterized by the removal of at least one initiation codon as described herein. The 5' replication recognition sequence is required for synthesis of the (−) strand complement of alphavirus genomic RNA, and is required for synthesis of (+) strand viral genomic RNA based on a (−) strand template. A native 5' replication recognition sequence typically encodes at least the N-terminal fragment of nsP1; but does not comprise the entire open reading frame encoding nsP1234. In view of the fact that a native 5' replication recognition sequence typically encodes at least the N-terminal fragment of nsP1, a native 5' replication recognition sequence typically comprises at least one initiation codon, typically AUG. In one embodiment, the 5' replication recognition sequence comprises conserved sequence element 1 of an alphavirus genome (CSE 1) or a variant thereof and conserved sequence element 2 of an alphavirus genome (CSE 2) or a variant thereof. The 5' replication recognition sequence is typically capable of forming four stem loops (SL), i.e. SL1, SL2, SL3, SL4. The numbering of these stem loops begins at the 5' end of the 5' replication recognition sequence.

According to the invention, the term "at the 5' end of an alphavirus" refers to the 5' end of the genome of an alphavirus. A nucleic acid sequence at the 5' end of an alphavirus encompasses the nucleotide located at the 5' terminus of alphavirus genomic RNA, plus optionally a consecutive sequence of further nucleotides. In one embodiment, a nucleic acid sequence at the 5' end of an alphavirus is identical to the 5' replication recognition sequence of the alphavirus genome.

The term "conserved sequence element" or "CSE" refers to a nucleotide sequence found in alphavirus RNA. These sequence elements are termed "conserved" because orthologs are present in the genome of different alphaviruses, and orthologous CSEs of different alphaviruses preferably share a high percentage of sequence identity and/or a similar secondary or tertiary structure. The term CSE includes CSE 1, CSE 2, CSE 3 and CSE 4.

According to the invention, the terms "CSE 1" or "44-nt CSE" synonymously refer to a nucleotide sequence that is required for (+) strand synthesis from a (−) strand template. The term "CSE 1" refers to a sequence on the (+) strand; and the complementary sequence of CSE 1 (on the (−) strand) functions as a promoter for (+) strand synthesis. Preferably, the term CSE 1 includes the most 5' nucleotide of the alphavirus genome. CSE 1 typically forms a conserved stem-loop structure. Without wishing to be bound to a particular theory, it is believed that, for CSE 1, the secondary structure is more important than the primary structure, i.e. the linear sequence. In genomic RNA of the model alphavirus Sindbis virus, CSE 1 consists of a consecutive sequence of 44 nucleotides, which is formed by the most 5' 44 nucleotides of the genomic RNA (Strauss & Strauss, Microbiol. Rev., 1994, vol. 58, pp. 491-562).

According to the invention, the terms "CSE 2" or "51-nt CSE" synonymously refer to a nucleotide sequence that is required for (−) strand synthesis from a (+) strand template. The (+) strand template is typically alphavirus genomic RNA or an RNA replicon (note that the subgenomic RNA transcript, which does not comprise CSE 2, does not function as a template for (−) strand synthesis). In alphavirus genomic RNA, CSE 2 is typically localized within the coding sequence for nsP1. In genomic RNA of the model alphavirus Sindbis virus, the 51-nt CSE is located at nucleotide positions 155-205 of genomic RNA (Frolov et al., 2001, RNA, vol. 7, pp. 1638-1651). CSE 2 forms typically two conserved stem loop structures. These stem loop structures are designated as stem loop 3 (SL3) and stem loop 4 (SL4) because they are the third and fourth conserved stem loop, respectively, of alphavirus genomic RNA, counted from the 5' end of alphavirus genomic RNA. Without wishing to be bound to a particular theory, it is believed that, for CSE 2, the secondary structure is more important than the primary structure, i.e. the linear sequence.

According to the invention, the terms "CSE 3" or "junction sequence" synonymously refer to a nucleotide sequence that is derived from alphaviral genomic RNA and that comprises the start site of the subgenomic RNA. The complement of this sequence in the (−) strand acts to promote subgenomic RNA transcription. In alphavirus genomic RNA, CSE 3 typically overlaps with the region encoding the C-terminal fragment of nsP4 and extends to a short non-coding region located upstream of the open reading frame encoding the structural proteins.

According to the invention, the terms "CSE 4" or "19-nt conserved sequence" or "19-nt CSE" synonymously refer to a nucleotide sequence from alphaviral genomic RNA, immediately upstream of the poly(A) sequence in the 3' untranslated region of the alphavirus genome. CSE 4 typically consists of 19 consecutive nucleotides. Without wishing to be bound to a particular theory, CSE 4 is understood to function as a core promoter for initiation of (−) strand synthesis (Jose et al., Future Microbiol., 2009, vol. 4, pp. 837-856); and/or CSE 4 and the poly(A) tail of the alphavirus genomic RNA are understood to function together for efficient (−) strand synthesis (Hardy & Rice, J. Virol., 2005, vol. 79, pp. 4630-4639).

According to the invention, the term "subgenomic promoter" or "SGP" refers to a nucleic acid sequence upstream (5') of a nucleic acid sequence (e.g. coding sequence), which controls transcription of said nucleic acid sequence by providing a recognition and binding site for RNA polymerase, typically RNA-dependent RNA polymerase, in particular functional alphavirus non-structural protein. The SGP may include further recognition or binding sites for further factors. A subgenomic promoter is typically a genetic element of a positive strand RNA virus, such as an alphavirus. A subgenomic promoter of alphavirus is a nucleic acid sequence comprised in the viral genomic RNA. The subgenomic promoter is generally characterized in that it allows initiation of the transcription (RNA synthesis) in the presence of an RNA-dependent RNA polymerase, e.g. functional alphavirus non-structural protein. A RNA (−) strand, i.e. the complement of alphaviral genomic RNA, serves as a template for synthesis of a (+) strand subgenomic transcript, and synthesis of the (+) strand subgenomic transcript is typically initiated at or near the subgenomic promoter. The term "subgenomic promoter" as used herein, is not confined to any particular localization in a nucleic acid comprising such subgenomic promoter. In some embodiments, the SGP is identical to CSE 3 or overlaps with CSE 3 or comprises CSE 3.

The terms "subgenomic transcript" or "subgenomic RNA" synonymously refer to a RNA molecule that is obtainable as a result of transcription using a RNA molecule as template ("template RNA"), wherein the template RNA comprises a subgenomic promoter that controls transcription of the subgenomic transcript. The subgenomic transcript is obtainable in the presence of an RNA-dependent RNA polymerase, in particular functional alphavirus non-structural protein. For instance, the term "subgenomic transcript" may refer to the RNA transcript that is prepared in a cell infected by an alphavirus, using the (−) strand complement of alphavirus genomic RNA as template. However, the term "subgenomic transcript", as used herein, is not limited thereto and also includes transcripts obtainable by using heterologous RNA as template. For example, subgenomic transcripts are also obtainable by using the (−) strand complement of SGP-containing replicons according to the present invention as template. Thus, the term "subgenomic transcript" may refer to a RNA molecule that is obtainable by transcribing a fragment of alphavirus genomic RNA, as well as to a RNA molecule that is obtainable by transcribing a fragment of a replicon according to the present invention.

The term "autologous" is used to describe anything that is derived from the same subject. For example, "autologous cell" refers to a cell derived from the same subject. Introduction of autologous cells into a subject is advantageous because these cells overcome the immunological barrier which otherwise results in rejection.

The term "allogeneic" is used to describe anything that is derived from different individuals of the same species. Two or more individuals are said to be allogeneic to one another when the genes at one or more loci are not identical.

The term "syngeneic" is used to describe anything that is derived from individuals or tissues having identical genotypes, i.e., identical twins or animals of the same inbred strain, or their tissues or cells.

The term "heterologous" is used to describe something consisting of multiple different elements. As an example, the introduction of one individual's cell into a different individual constitutes a heterologous transplant. A heterologous gene is a gene derived from a source other than the subject.

The following provides specific and/or preferred variants of the individual features of the invention. The present invention also contemplates as particularly preferred embodiments those embodiments, which are generated by combining two or more of the specific and/or preferred variants described for two or more of the features of the present invention.

RNA Replicon

A nucleic acid construct that is capable of being replicated by a replicase, preferably an alphaviral replicase, is termed replicon. According to the invention, the term "replicon" defines a RNA molecule that can be replicated by RNA-dependent RNA polymerase, yielding—without DNA intermediate—one or multiple identical or essentially identical copies of the RNA replicon. "Without DNA intermediate" means that no deoxyribonucleic acid (DNA) copy or complement of the replicon is formed in the process of forming the copies of the RNA replicon, and/or that no deoxyribonucleic acid (DNA) molecule is used as a template in the process of forming the copies of the RNA replicon, or complement thereof. The replicase function is typically provided by functional alphavirus non-structural protein.

According to the invention, the terms "can be replicated" and "capable of being replicated" generally describe that one or more identical or essentially identical copies of a nucleic acid can be prepared. When used together with the term "replicase", such as in "capable of being replicated by a replicase", the terms "can be replicated" and "capable of being replicated" describe functional characteristics of a nucleic acid molecule, e.g. a RNA replicon, with respect to a replicase. These functional characteristics comprise at least one of (i) the replicase is capable of recognizing the replicon and (ii) the replicase is capable of acting as RNA-dependent RNA polymerase (RdRP). Preferably, the replicase is capable of both (i) recognizing the replicon and (ii) acting as RNA-dependent RNA polymerase.

The expression "capable of recognizing" describes that the replicase is capable of physically associating with the replicon, and preferably, that the replicase is capable of binding to the replicon, typically non-covalently. The term "binding" can mean that the replicase has the capacity of binding to any one or more of a conserved sequence element 1 (CSE 1) or complementary sequence thereof (if comprised by the replicon), conserved sequence element 2 (CSE 2) or complementary sequence thereof (if comprised by the replicon), conserved sequence element 3 (CSE 3) or complementary sequence thereof (if comprised by the replicon), conserved sequence element 4 (CSE 4) or complementary sequence thereof (if comprised by the replicon). Preferably, the replicase is capable of binding to CSE 2 [i.e. to the (+) strand] and/or to CSE 4 [i.e. to the (+) strand], or of binding to the complement of CSE 1 [i.e. to the (−) strand] and/or to the complement of CSE 3 [i.e. to the (−) strand].

The expression "capable of acting as RdRP" means that the replicase is capable to catalyze the synthesis of the (−) strand complement of alphaviral genomic (+) strand RNA, wherein the (+) strand RNA has template function, and/or that the replicase is capable to catalyze the synthesis of (+) strand alphaviral genomic RNA, wherein the (−) strand RNA has template function. In general, the expression "capable of acting as RdRP" can also include that the replicase is capable to catalyze the synthesis of a (+) strand subgenomic transcript wherein a (−) strand RNA has template function, and wherein synthesis of the (+) strand subgenomic transcript is typically initiated at an alphavirus subgenomic promoter.

The expressions "capable of binding" and "capable of acting as RdRP" refer to the capability at normal physiological conditions. In particular, they refer to the conditions inside a cell, which expresses functional alphavirus non-structural protein or which has been transfected with a nucleic acid that codes for functional alphavirus non-structural protein. The cell is preferably a eukaryotic cell. The capability of binding and/or the capability of acting as RdRP can be experimentally tested, e.g. in a cell-free in vitro system or in a eukaryotic cell. Optionally, said eukaryotic cell is a cell from a species to which the particular alphavirus that represents the origin of the replicase is infectious. For example, when the alphavirus replicase from a particular alphavirus is used that is infectious to humans, the normal physiological conditions are conditions in a human cell. More preferably, the eukaryotic cell (in one example human cell) is from the same tissue or organ to which the particular alphavirus that represents the origin of the replicase is infectious.

According to the invention, "compared to a native alphavirus sequence" and similar terms refer to a sequence that is a variant of a native alphavirus sequence. The variant is typically not itself a native alphavirus sequence.

The RNA replicon of the invention comprises a 5' replication recognition sequence. A 5' replication recognition sequence is a nucleic acid sequence that can be recognized by functional alphavirus non-structural protein. In other words, functional alphavirus non-structural protein is capable of recognizing the 5' replication recognition sequence.

In one embodiment, the RNA replicon of the invention comprises a 5' replication recognition sequence, wherein the 5' replication recognition sequence is characterized in that it comprises the removal of at least one initiation codon compared to a native alphavirus 5' replication recognition sequence.

The 5' replication recognition sequence that is characterized in that it comprises the removal of at least one initiation codon compared to a native alphavirus 5' replication recognition sequence, according to the present invention, can be referred to herein as "modified 5' replication recognition sequence" or "5' replication recognition sequence according to the invention". As described herein below, the 5' replication recognition sequence according to the invention may optionally be characterized by the presence of one or more additional nucleotide changes.

In one embodiment, the RNA replicon comprises a 3' replication recognition sequence. A 3' replication recognition sequence is a nucleic acid sequence that can be recognized by functional alphavirus non-structural protein. In other words, functional alphavirus non-structural protein is capable of recognizing the 3' replication recognition sequence. Preferably, the 3' replication recognition sequence is located at the 3' end of the replicon (if the replicon does not comprise a poly(A) tail), or immediately upstream of the poly(A) tail (if the replicon comprises a poly(A) tail). In one embodiment, the 3' replication recognition sequence consists of or comprises CSE 4.

In one embodiment, the 5' replication recognition sequence and the 3' replication recognition sequence are capable of directing replication of the RNA replicon according to the present invention in the presence of functional alphavirus non-structural protein. Thus, when present alone or preferably together, these recognition sequences direct replication of the RNA replicon in the presence of functional alphavirus non-structural protein.

It is preferable that a functional alphavirus non-structural protein is provided in cis (encoded as protein of interest by an open reading frame on the replicon) or in trans (encoded as protein of interest by an open reading frame on a separate replicase construct as described in the second aspect), that is capable of recognizing both the optionally modified 5' replication recognition sequence and the 3' replication recognition sequence of the replicon. In one embodiment, this is achieved when the 5' replication recognition sequence and the 3' replication recognition sequence are native to the alphavirus from which the functional alphavirus non-structural protein is derived, or when the 3' replication recognition sequence is native to the alphavirus from which the functional alphavirus non-structural protein is derived and the modified 5' replication recognition sequence is a variant of the 5' replication recognition sequence that is native to the alphavirus from which the functional alphavirus non-structural protein is derived. Native means that the natural origin of these sequences is the same alphavirus. In an alternative embodiment, the (modified) 5' replication recognition sequence and/or the 3' replication recognition sequence are not native to the alphavirus from which the functional alphavirus non-structural protein is derived, provided that the functional alphavirus non-structural protein is capable of recognizing both the (modified) 5' replication recognition sequence and the 3' replication recognition sequence of the replicon. In other words, the functional alphavirus non-structural protein is compatible to the (modified) 5' replication recognition sequence and the 3' replication recognition sequence. When a non-native functional alphavirus non-structural protein is capable of recognizing a respective sequence or sequence element, the functional alphavirus non-structural protein is said to be compatible (cross-virus compatibility). Any combination of (3'/5') replication recognition sequences and CSEs, respectively, with functional alphavirus non-structural protein is possible as long as cross-virus compatibility exists. Cross-virus compatibility can readily be tested by the skilled person working the present invention by incubating a functional alphavirus non-structural protein to be tested together with an RNA, wherein the RNA has 3'- and (optionally modified) 5' replication recognition sequences to be tested, at conditions suitable for RNA replication, e.g. in a suitable host cell. If replication occurs, the (3'/5') replication recognition sequences and the functional alphavirus non-structural protein are determined to be compatible.

The removal of at least one initiation codon provides several advantages. Absence of an initiation codon in the nucleic acid sequence encoding nsP1* will typically cause that nsP1* (N-terminal fragment of nsP1) is not translated. Further, since nsP1* is not translated, the open reading frame encoding the protein of interest ("Transgene") is the most upstream open reading frame accessible to the ribosome; thus when the replicon is present in a cell, translation is initiated at the first AUG of the open reading frame (RNA) encoding the gene of interest. This represents an advantage over prior art trans-replicons, such as those described by Spuul et al. (J. Virol., 2011, vol. 85, pp. 4739-4751): replicons according to Spuul et al. direct the expression of the N-terminal portion of nsP1, a peptide of 74 amino acids. It is also known from the prior art that construction of RNA replicons from full-length virus genomes is not a trivial matter, as certain mutations can render RNA incapable of being replicated (WO 2000/053780 A2), and removal of some parts of the 5' structure that is important for replication of alphavirus affects efficiency of replication (Kamrud et al., 2010, J. Gen. Virol., vol. 91, pp. 1723-1727).

The advantage over conventional cis-replicons is that removal of at least one initiation codon uncouples the coding region for the alphaviral non-structural protein from the 5' replication recognition sequence. This enables a further engineering of cis-replicons e.g. by exchanging the native 5' replication recognition sequence to an artificial sequence, a mutated sequence, or a heterologous sequence taken from another RNA virus. Such sequence manipulations in conventional cis-replicons are restricted by the amino acid sequence of nsP1. Any point mutation, or clusters of point mutations, would require experimental assessment whether replication is affected and small insertions or deletion leading to frame shift mutations are impossible due to their detrimental effect on the protein.

The removal of at least one initiation codon according to the present invention can be achieved by any suitable method known in the art. For example, a suitable DNA molecule encoding the replicon according to the invention, i.e. characterized by the removal of an initiation codon, can be designed in silico, and subsequently synthesized in vitro (gene synthesis); alternatively, a suitable DNA molecule may be obtained by site-directed mutagenesis of a DNA sequence encoding a replicon. In any case, the respective DNA molecule may serve as template for in vitro transcription, thereby providing the replicon according to the invention.

The removal of at least one initiation codon compared to a native alphavirus 5' replication recognition sequence is not particularly limited and may be selected from any nucleotide modification, including substitution of one or more nucleotides (including, on DNA level, a substitution of A and/or T and/or G of the initiation codon); deletion of one or more nucleotides (including, on DNA level, a deletion of A and/or T and/or G of the initiation codon), and insertion of one or more nucleotides (including, on DNA level, an insertion of one or more nucleotides between A and T and/or between T and G of the initiation codon). Irrespective of whether the nucleotide modification is a substitution, an insertion or a deletion, the nucleotide modification must not result in the formation of a new initiation codon (as an illustrative example: an insertion, at DNA level, must not be an insertion of an ATG).

The 5' replication recognition sequence of the RNA replicon that is characterized by the removal of at least one initiation codon (i.e. the modified 5' replication recognition sequence according to the present invention) is preferably a variant of a 5' replication recognition sequence of the genome of an alphavirus found in nature. In one embodiment, the modified 5' replication recognition sequence according to the present invention is preferably characterized by a degree of sequence identity of 80% or more, preferably 85% or more, more preferably 90% or more, even more preferably 95% or more, to the 5' replication recognition sequence of the genome of at least one alphavirus found in nature.

In one embodiment, the 5' replication recognition sequence of the RNA replicon that is characterized by the removal of at least one initiation codon comprises a sequence homologous to about 250 nucleotides at the 5' end of an alphavirus, i.e. at the 5' end of the alphaviral genome. In a preferred embodiment, it comprises a sequence homologous to about 250 to 500, preferably about 300 to 500 nucleotides at the 5' end of an alphavirus, i.e. at the 5' end of the alphaviral genome. "At the 5' end of the alphaviral genome" means a nucleic acid sequence beginning at, and including, the most upstream nucleotide of the alphaviral genome. In other words, the most upstream nucleotide of the alphaviral genome is designated nucleotide no. 1, and e.g. "250 nucleotides at the 5' end of the alphaviral genome" means nucleotides 1 to 250 of the alphaviral genome. In one embodiment, the 5' replication recognition sequence of the RNA replicon that is characterized by the removal of at least one initiation codon is characterized by a degree of sequence identity of 80% or more, preferably 85% or more, more preferably 90% or more, even more preferably 95 (3/0 or more, to at least 250 nucleotides at the 5' end of the genome of at least one alphavirus found in nature. At least 250 nucleotides includes e.g. 250 nucleotides, 300 nucleotides, 400 nucleotides, 500 nucleotides.

The 5' replication recognition sequence of an alphavirus found in nature is typically characterized by at least one initiation codon and/or by conserved secondary structural motifs. For example, the native 5' replication recognition sequence of Semliki Forest virus (SFV) comprises five specific AUG base triplets. According to Frolov et al. (2001, RNA, vol. 7, pp. 1638-1651) analysis by MFOLD revealed that the native 5' replication recognition sequence of Semliki Forest virus is predicted to form four stem loops (SL), termed stem loops 1 to 4 (SL1, SL2, SL3, SL4). According to Frolov et al., analysis by MFOLD revealed that also the native 5' replication recognition sequence of a different alphavirus, Sindbis virus, is predicted to form four stem loops: SL1, SL2, SL3, SL4.

It is known that the 5' end of the alphaviral genome comprises sequence elements that enable replication of the alphaviral genome by functional alphavirus non-structural protein. In one embodiment of the present invention, the 5' replication recognition sequence of the RNA replicon comprises a sequence homologous to conserved sequence element 1 (CSE 1) and/or a sequence homologous to conserved sequence element 2 (CSE 2) of an alphavirus.

Conserved sequence element 2 (CSE 2) of alphavirus genomic RNA typically is represented by SL3 and SL4 which is preceded by SL2 comprising at least the native initiation codon that encodes the first amino acid residue of alphavirus non-structural protein nsP1. In this description, however, in some embodiments, the conserved sequence element 2 (CSE 2) of alphavirus genomic RNA refers to a region spanning from SL2 to SL4 and comprising the native initiation codon that encodes the first amino acid residue of alphavirus non-structural protein nsP1. In a preferred embodiment, the RNA replicon comprises CSE 2 or a sequence homologous to CSE 2. In one embodiment, the RNA replicon comprises a sequence homologous to CSE 2 that is preferably characterized by a degree of sequence identity of 80% or more, preferably 85% or more, more preferably 90% or more, even more preferably 95% or more, to the sequence of CSE 2 of at least one alphavirus found in nature.

In a preferred embodiment, the 5' replication recognition sequence comprises a sequence that is homologous to CSE 2 of an alphavirus. The CSE 2 of an alphavirus may comprise a fragment of an open reading frame of a non-structural protein from an alphavirus.

Thus, in a preferred embodiment, the RNA replicon is characterized in that it comprises a sequence homologous to an open reading frame of a non-structural protein or a fragment thereof from an alphavirus. The sequence homologous to an open reading frame of a non-structural protein or a fragment thereof is typically a variant of an open reading frame of a non-structural protein or a fragment thereof of an alphavirus found in nature. In one embodiment, the sequence homologous to an open reading frame of a non-structural protein or a fragment thereof is preferably characterized by a degree of sequence identity of 80% or more, preferably 85% or more, more preferably 90% or more, even more preferably 95% or more, to an open reading frame of a non-structural protein or a fragment thereof of at least one alphavirus found in nature.

In a more preferred embodiment, the sequence homologous to an open reading frame of a non-structural protein that is comprised by the replicon of the present invention does not comprise the native initiation codon of a non-structural protein, and more preferably does not comprise any initiation codon of a non-structural protein. In a preferred embodiment, the sequence homologous to CSE 2 is characterized by the removal of all initiation codons compared to a native alphavirus CSE 2 sequence. Thus, the sequence homologous to CSE 2 does preferably not comprise any initiation codon.

When the sequence homologous to an open reading frame does not comprise any initiation codon, the sequence homologous to an open reading frame is not itself an open reading frame since it does not serve as a template for translation.

In one embodiment, the 5' replication recognition sequence comprises a sequence homologous to an open reading frame of a non-structural protein or a fragment thereof from an alphavirus, wherein the sequence homologous to an open reading frame of a non-structural protein or a fragment thereof from an alphavirus is characterized in that it comprises the removal of at least one initiation codon compared to the native alphavirus sequence.

In a preferred embodiment, the sequence homologous to an open reading frame of a non-structural protein or a fragment thereof from an alphavirus is characterized in that it comprises the removal of at least the native start codon of the open reading frame of a non-structural protein. Preferably, it is characterized in that it comprises the removal of at least the native start codon of the open reading frame encoding nsP1.

The native start codon is the AUG base triplet at which translation on ribosomes in a host cell begins when an RNA is present in a host cell. In other words, the native start codon is the first base triplet that is translated during ribosomal protein synthesis, e.g. in a host cell that has been inoculated with RNA comprising the native start codon. In one embodiment, the host cell is a cell from a eukaryotic species that is a natural host of the specific alphavirus that comprises the native alphavirus 5' replication recognition sequence. In a preferred embodiment, the host cell is a BHK21 cell from the cell line "BHK21 [C13] (ATCC® CCL10™)", available from American Type Culture Collection, Manassas, Virginia, USA.

The genomes of many alphaviruses have been fully sequenced and are publically accessible, and the sequences of non-structural proteins encoded by these genomes are publically accessible as well. Such sequence information allows to determine the native start codon in silica In one embodiment, the native start codon is comprised by a Kozak sequence or a functionally equivalent sequence. The Kozak sequence is a sequence initially described by Kozak (1987, Nucleic Acids Res., vol. 15, pp. 8125-8148). The Kozak sequence on an mRNA molecule is recognized by the ribosome as the translational start site. According to this reference, the Kozak sequence comprises an AUG start codon, immediately followed by a highly conserved G nucleotide: AUGG. In one embodiment of the present invention, the sequence homologous to an open reading frame of a non-structural protein or a fragment thereof from an alphavirus is characterized in that it comprises the removal of an initiation codon that is part of a Kozak sequence.

In one embodiment of the present invention, the 5' replication recognition sequence of the replicon is characterized by the removal of at least all those initiation codons, which, at RNA level, are part of an AUGG sequence.

In a preferred embodiment, the sequence homologous to an open reading frame of a non-structural protein or a fragment thereof from an alphavirus is characterized in that it comprises the removal of one or more initiation codons other than the native start codon of the open reading frame of a non-structural protein. In a more preferred embodiment, said nucleic acid sequence is additionally characterized by the removal of the native start codon. For example, in addition to the removal of the native start codon, any one or two or three or four or more than four (e.g. five) initiation codons may be removed.

If the replicon is characterized by the removal of the native start codon, and optionally by the removal of one or more initiation codons other than the native start codon, of the open reading frame of a non-structural protein, the sequence homologous to an open reading frame is not itself an open reading frame since it does not serve as a template for translation.

The one or more initiation codon other than the native start codon that is removed, preferably in addition to removal of the native start codon, is preferably selected from an AUG base triplet that has the potential to initiate translation. An AUG base triplet that has the potential to initiate translation may be referred to as "potential initiation codon". Whether a given AUG base triplet has the potential to initiate translation can be determined in silico or in a cell-based in vitro assay.

In one embodiment, it is determined in silico whether a given AUG base triplet has the potential to initiate translation: in that embodiment, the nucleotide sequence is examined, and an AUG base triplet is determined to have the potential to initiate translation if it is part of an <u>AUGG</u> sequence, preferably part of a Kozak sequence.

In one embodiment, it is determined in a cell-based in vitro assay whether a given AUG base triplet has the potential to initiate translation: a RNA replicon characterized by the removal of the native start codon and comprising the given AUG base triplet downstream of the position of the removal of the native start codon is introduced into a host cell. In one embodiment, the host cell is a cell from a eukaryotic species that is a natural host of the specific alphavirus that comprises the native alphavirus 5' replication recognition sequence. In a preferred embodiment, the host cell is a BHK21 cell from the cell line "BHK21 [C13] (ATCC® CCL10™)", available from American Type Culture Collection, Manassas, Virginia, USA. It is preferable that no further AUG base triplet is present between the position of the removal of the native start codon and the given AUG base triplet. If, following transfer of the RNA replicon-characterized by the removal of the native start codon and comprising the given AUG base triplet—into the host cell, translation is initiated at the given AUG base triplet, the given AUG base triplet is determined to have the potential to initiate translation. Whether translation is initiated can be determined by any suitable method known in the art. For example, the replicon may encode, downstream of the given AUG base triplet and in-frame with the given AUG base triplet, a tag that facilitates detection of the translation product (if any), e.g. a myc-tag or a HA-tag; whether or not an expression product having the encoded tag is present may be determined e.g. by Western Blot. In this embodiment, it is preferable that no further AUG base triplet is present between the given AUG base triplet and the nucleic acid sequence encoding the tag. The cell-based in vitro assay can be performed individually for more than one given AUG base triplet: in each case, it is preferable that no further AUG base triplet is present between the position of the removal of the native start codon and the given AUG base triplet. This can be achieved by removing all AUG base triplets (if any) between the position of the removal of the native start codon and the given AUG base triplet. Thereby, the given AUG base triplet is the first AUG base triplet downstream of the position of the removal of the native start codon.

Preferably, the replicon according to the present invention is characterized by the removal of all potential initiation codons that are downstream of the position of the removal of the native start codon and that are located within the open reading frame of alphavirus non-structural protein or of a fragment thereof. Thus, according to the invention, the 5' replication recognition sequence preferably does not comprise an open reading frame that can be translated to protein.

In a preferred embodiment, the 5' replication recognition sequence of the RNA replicon according to the invention is characterized by a secondary structure that is equivalent to the secondary structure of the 5' replication recognition sequence of alphaviral genomic RNA. In a preferred embodiment, the 5' replication recognition sequence of the RNA replicon according to the invention is characterized by a predicted secondary structure that is equivalent to the predicted secondary structure of the 5' replication recognition sequence of alphaviral genomic RNA. According to the present invention, the secondary structure of an RNA molecule is preferably predicted by the web server for RNA secondary structure prediction http://rna.urmc.rochester.edu/RNAstructureWeb/Servers/Predict1/Predict1.html.

By comparing the secondary structure or predicted secondary structure of a 5' replication recognition sequence of an RNA replicon characterized by the removal of at least one initiation codon compared to the native alphavirus 5' replication recognition sequence, the presence or absence of a nucleotide pairing disruption can be identified. For example, at least one base pair may be absent at a given position, compared to a native alphavirus 5' replication recognition sequence, e.g. a base pair within a stem loop, in particular the stem of the stem loop.

In a preferred embodiment, one or more stem loops of the 5' replication recognition sequence are not deleted or disrupted. More preferably, stem loops 3 and 4 are not deleted or disrupted. More preferably, none of the stem loops of the 5' replication recognition sequence is deleted or disrupted.

In one embodiment, the removal of at least one initiation codon does not disrupt the secondary structure of the 5' replication recognition sequence. In an alternative embodiment, the removal of at least one initiation codon does disrupt the secondary structure of the 5' replication recognition sequence. In this embodiment, the removal of at least one initiation codon may be causative for the absence of at least one base pair at a given position, e.g. a base pair within a stem loop, compared to a native alphavirus 5' replication recognition sequence. If a base pair is absent within a stem loop, compared to a native alphavirus 5' replication recognition sequence, the removal of at least one initiation codon is determined to introduce a nucleotide pairing disruption within the stem loop. A base pair within a stem loop is typically a base pair in the stem of the stem loop.

In a preferred embodiment, the RNA replicon comprises one or more nucleotide changes compensating for nucleotide pairing disruptions within one or more stem loops introduced by the removal of at least one initiation codon.

If the removal of at least one initiation codon introduces a nucleotide pairing disruption within a stem loop, compared to a native alphavirus 5' replication recognition sequence, one or more nucleotide changes may be introduced which are expected to compensate for the nucleotide pairing disruption, and the secondary structure or predicted secondary structure obtained thereby may be compared to a native alphavirus 5' replication recognition sequence.

Based on the common general knowledge and on the disclosure herein, certain nucleotide changes can be expected by the skilled person to compensate for nucleotide pairing disruptions. For example, if a base pair is disrupted at a given position of the secondary structure or predicted secondary structure of a given 5' replication recognition sequence of an RNA replicon characterized by the removal of at least one initiation codon, compared to the native alphavirus 5' replication recognition sequence, a nucleotide change that restores a base pair at that position, preferably without re-introducing an initiation codon, is expected to compensate for the nucleotide pairing disruption.

In a preferred embodiment, the 5' replication recognition sequence of the replicon does not overlap with, or does not comprise, a translatable nucleic acid sequence, i.e. translatable into a peptide or protein, in particular a nsP, in particular nsP1, or a fragment of any thereof. For a nucleotide sequence to be "translatable", it requires the presence of an initiation codon; the initiation codon encodes the most N-terminal amino acid residue of the peptide or protein. In one embodiment, the 5' replication recognition sequence of the replicon does not overlap with, or does not comprise, a translatable nucleic acid sequence encoding an N-terminal fragment of nsP1.

In some scenarios, which are described in detail below, the RNA replicon comprises at least one subgenomic promoter. In a preferred embodiment, the subgenomic promoter of the replicon does not overlap with, or does not comprise, a translatable nucleic acid sequence, i.e. translatable into a peptide or protein, in particular a nsP, in particular nsP4, or a fragment of any thereof. In one embodiment, the subgenomic promoter of the replicon does not overlap with, or does not comprise, a translatable nucleic acid sequence that encodes a C-terminal fragment of nsP4. A RNA replicon having a subgenomic promoter that does not overlap with, or does not comprise, a translatable nucleic acid sequence, e.g. translatable into the C-terminal fragment of nsP4, may be generated by deleting part of the coding sequence for nsP4 (typically the part encoding the N-terminal part of nsP4), and/or by removing AUG base triplets in the part of the coding sequence for nsP4 that has not been deleted. If AUG base triplets in the coding sequence for nsP4 or a part thereof are removed, the AUG base triplets that are removed are preferably potential initiation codons. Alternatively, if the subgenomic promoter does not overlap with a nucleic acid sequence that encodes nsP4, the entire nucleic acid sequence encoding nsP4 may be deleted.

In one embodiment, the RNA replicon does not comprise an open reading frame encoding a truncated alphavirus non-structural protein. In the context of this embodiment, it is particularly preferable that the RNA replicon does not comprise an open reading frame encoding the N-terminal fragment of nsP1, and optionally does not comprise an open reading frame encoding the C-terminal fragment of nsP4. The N-terminal fragment of nsP1 is a truncated alphavirus protein; the C-terminal fragment of nsP4 is also a truncated alphavirus protein.

In some embodiments the replicon according to the present invention does not comprise stem loop 2 (SL2) of the 5' terminus of the genome of an alphavirus. According to Frolov et al., supra, stem loop 2 is a conserved secondary structure found at the 5' terminus of the genome of an alphavirus, upstream of CSE 2, but is dispensable for replication.

In one embodiment, the 5' replication recognition sequence of the replicon does not overlap with a nucleic acid sequence that encodes alphavirus non-structural protein or a fragment thereof. Thus, the present invention encompasses replicons that are characterized, compared to genomic alphaviral RNA, by the removal of at least one initiation codon, as described herein, optionally combined with the deletion of the coding region for one or more alphavirus non-structural proteins, or a part thereof. For example, the coding region for nsP2 and nsP3 may be deleted, or the coding region for nsP2 and nsP3 may be deleted together with the deletion of the coding region for the C-terminal fragment of nsP1 and/or of the coding region for the N-terminal fragment of nsP4, and one or more remaining initiation codons, i.e. remaining after said removal, may be removed as described herein.

Deletion of the coding region for one or more alphavirus non-structural proteins may be achieved by standard methods, e.g., at DNA level, excision by the help of restriction enzymes, preferably restriction enzymes that recognize unique restriction sites in the open reading frame. Optionally, unique restriction sites may be introduced into an open reading frame by mutagenesis, e.g. site-directed mutagenesis. The respective DNA may be used as template for in vitro transcription.

A restriction site is a nucleic acid sequence, e.g. DNA sequence, which is necessary and sufficient to direct restriction (cleavage) of the nucleic acid molecule, e.g. DNA molecule, in which the restriction site is contained, by a specific restriction enzyme. A restriction site is unique for a given nucleic acid molecule if one copy of the restriction site is present in the nucleic acid molecule.

A restriction enzyme is an endonuclease that cuts a nucleic acid molecule, e.g. DNA molecule, at or near the restriction site.

Alternatively, a nucleic acid sequence characterized by the deletion of part or all of the open reading frame may be obtained by synthetic methods.

The RNA replicon according to the present invention is preferably a single stranded RNA molecule. The RNA replicon according to the present invention is typically a (+) stranded RNA molecule. In one embodiment, the RNA replicon of the present invention is an isolated nucleic acid molecule.

Reprogramming Factors and Reprogramming of Cells

The present invention provides technology to change one type of highly specialized somatic cells, e.g. fibroblasts or keratinocytes, into another type, e.g., neuronal cells, via a pluripotent cell intermediate.

Specifically, by providing a differentiated somatic cell with reprogramming factors which are preferably present in pluripotent cell types, preferably stem cells, more preferably embryonic stem cells, the invention restores the cell's epigenetic memory to a state similar to that of pluripotent stem cells. With the present invention, embryos do not have to be used, created, or destroyed to generate cells having stem cell characteristics, in particular pluripotency, thus eliminating ethical concerns. Furthermore, the present invention does not require the use of vectors that integrate into the genome such as viral vectors potentially introducing mutations at the insertion site.

The somatic cells used according to the present invention have an important advantage over oocytes as a means of inducing reprogramming in that they can be easily expanded in number in vitro. In addition, the present invention allows the use of patient-specific somatic cells and thus, largely eliminates the concerns of immune rejection and problems associated with patient immunosuppression. Using cells generated according to the present invention for autologous cell transplantation is unlikely to induce adverse side effects and/or resistance. If required, repeated cell transplantation is feasible. However, since the present invention will significantly reduce the need for immunosuppression of the patient to reduce acute and hyperacute rejection the need for repeated transplantation procedures will also be alleviated, reducing the cost of disease treatment.

The term "cells having stem cell characteristics" is used herein to designate cells which, although they are derived from differentiated somatic non-stem cells, exhibit one or more features typical for stem cells, in particular embryonic stem cells. Such features include an embryonic stem cell morphology such as compact colonies, high nucleus to cytoplasm ratio and prominent nucleoli, normal karyotypes, expression of telomerase activity, expression of cell surface markers that are characteristic for embryonic stem cells, and/or expression of genes that are characteristic for embryonic stem cells. The cell surface markers that are characteristic for embryonic stem cells are, for example, selected from the group consisting of stage-specific embryonic antigen-3 (SSEA-3), SSEA-4, tumor-related antigen-1-60 (TRA-1-60), TRA-1-81, and TRA-2-49/6E. The genes that are characteristic for embryonic stem cells are selected, for example, from the group consisting of endogenous OCT4, endogenous NANOG, growth and differentiation factor 3

(GDF3), reduced expression 1 (REX1), fibroblast growth factor 4 (FGF4), embryonic cell-specific gene 1 (ESG1), developmental pluripotency-associated 2 (DPPA2), DPPA4, and telomerase reverse transcriptase (TERT). In one embodiment, the one or more features typical for stem cells include pluripotency. In one embodiment, the cells having stem cell characteristics exhibit a pluripotent state. In one embodiment, the cells having stem cell characteristics have the developmental potential to differentiate into advanced derivatives of all three primary germ layers. In one embodiment, the primary germ layer is endoderm and the advanced derivative is gut-like epithelial tissue. In a further embodiment, the primary germ layer is mesoderm and the advanced derivative is striated muscle and/or cartilage. In an even further embodiment, the primary germ layer is ectoderm and the advanced derivative is neural tissue and/or epidermal tissue. In one preferred embodiment, the cells having stem cell characteristics have the developmental potential to differentiate into neuronal cells and/or cardiac cells. According to the invention, generally the terms "cells having stem cell characteristics", "cells having stem cell properties", "stem like cells", "reprogrammed cells" and "de-differentiated cells" or similar terms have similar meanings and are used interchangeably herein.

A "stem cell" is a cell with the ability to self-renew, to remain undifferentiated, and to become differentiated. A stem cell can divide without limit, for at least the lifetime of the animal in which it naturally resides. A stem cell is not terminally differentiated; it is not at the end stage of a differentiation pathway. When a stem cell divides, each daughter cell can either remain a stem cell or embark on a course that leads toward terminal differentiation.

Totipotent stem cells are cells having totipotential differentiation properties and being capable of developing into a complete organism. This property is possessed by cells up to the 8-cell stage after fertilization of the oocyte by the sperm. When these cells are isolated and transplanted into the uterus, they can develop into a complete organism.

Pluripotent stem cells are cells capable of developing into various cells and tissues derived from the ectodermal, mesodermal and endodermal layers. Pluripotent stem cells which are derived from the inner cell mass located inside of blastocysts, generated 4-5 days after fertilization are called "embryonic stem cells" and can differentiate into various other tissue cells but cannot form new living organisms.

Multipotent stem cells are stem cells differentiating normally into only cell types specific to their tissue and organ of origin. Multipotent stem cells are involved not only in the growth and development of various tissues and organs during the fetal, neonatal and adult periods but also in the maintenance of adult tissue homeostasis and the function of inducing regeneration upon tissue damage. Tissue-specific multipotent cells are collectively called "adult stem cells".

An "embryonic stem cell" is a stem cell that is present in or isolated from an embryo. It can be pluripotent, having the capacity to differentiate into each and every cell present in the organism, or multipotent, with the ability to differentiate into more than one cell type.

As used herein, "embryo" refers to an animal in the early stages of it development. These stages are characterized by implantation and gastrulation, where the three germ layers are defined and established and by differentiation of the germs layers into the respective organs and organ systems. The three germ layers are the endoderm, ectoderm and mesoderm.

A "blastocyst" is an embryo at an early stage of development in which the fertilized ovum has undergone cleavage, and a spherical layer of cells surrounding a fluid-filled cavity is forming, or has formed. This spherical layer of cells is the trophectoderm. Inside the trophectoderm is a cluster of cells termed the inner cell mass (ICM). The trophectoderm is the precursor of the placenta, and the ICM is the precursor of the embryo.

An adult stem cell, also called a somatic stem cell, is a stem cell found in an adult. An adult stem cell is found in a differentiated tissue, can renew itself, and can differentiate, with some limitations, to yield specialized cell types of its tissue of origin. Examples include mesenchymal stem cells, hematopoietic stem cells, and neural stem cells.

A "differentiated cell" is a mature cell that has undergone progressive developmental changes to a more specialized form or function. Cell differentiation is the process a cell undergoes as it matures to an overtly specialized cell type. Differentiated cells have distinct characteristics, perform specific functions, and are less likely to divide than their less differentiated counterparts.

An "undifferentiated" cell, for example, an immature, embryonic, or primitive cell, typically has a nonspecific appearance, may perform multiple, non-specific activities, and may perform poorly, if at all, in functions typically performed by differentiated cells.

"Somatic cell" refers to any and all differentiated cells and does not include stem cells, germ cells, or gametes. Preferably, "somatic cell" as used herein refers to a terminally differentiated cell. In one embodiment, the somatic cells are fibroblasts such as lung fibroblasts, foreskin fibroblasts or dermal fibroblasts, or keratinocytes.

In one embodiment, the somatic cells are embryonic stem cell derived somatic cells with a mesenchymal phenotype. In a preferred embodiment, the somatic cells are fibroblasts such as fetal fibroblasts or postnatal fibroblasts or keratinocytes, preferably hair follicle derived keratinocytes. In further embodiments, the fibroblasts are lung fibroblasts, foreskin fibroblasts or dermal fibroblasts. In particular embodiments, the fibroblasts are fibroblasts as deposited at the American Type Culture Collection (ATCC) under Catalog No. CCL-186, as deposited at the American Type Culture Collection (ATCC) under Catalog No. CRL-2097 or as deposited at the American Type Culture Collection (ATCC) under Catalog No. CRL-2522, as distributed by SBI System Biosciences under the catalog no. PC501A-HFF, or as distributed by Innoprot under the catalog no. P10857. In one embodiment, the fibroblasts are adult human dermal fibroblasts. Preferably, the somatic cells are human cells. According to the present invention, the somatic cells may be genetically modified.

As used herein, "committed" refers to cells which are considered to be permanently committed to a specific function. Committed cells are also referred to as "terminally differentiated cells".

As used herein, "differentiation" refers to the adaptation of cells for a particular form or function. In cells, differentiation leads to a more committed cell.

As used herein, "de-differentiation" refers to loss of specialization in form or function. In cells, de-differentiation leads to a less committed cell.

As used herein "reprogramming" refers to the resetting of the genetic program of a cell. A reprogrammed cell preferably exhibits pluripotency.

The terms "de-differentiated" and "reprogrammed" or similar terms are used interchangeably herein to denote somatic cell-derived cells having stem cell characteristics.

However, said terms are not intended to limit the subject-matter disclosed herein by mechanistic or functional considerations.

As used herein, "germ cell" refers to a reproductive cell such as a spermatocyte or an oocyte, or a cell that will develop into a reproductive cell.

As used herein, "pluripotent" refers to cells that can give rise to any cell type except the cells of the placenta or other supporting cells of the uterus.

According to the invention it is preferred that introduction of RNA replicons capable of expressing reprogramming factors as disclosed herein into somatic cells results in expression of said factors for a time period to complete the reprogramming process and in the development of cells having stem cell characteristics. Preferably, introduction of RNA capable of expression certain factors as disclosed herein into somatic cells results in expression of said factors for an extended period of time, preferably for at least 10 days, preferably for at least 11 days and more preferably for at least 12 days. To achieve such long term expression, RNA is preferably periodically introduced into the cells more than one time, preferably using electroporation or lipofection. Preferably, RNA is introduced into the cells at least twice, more preferably at least 3 times, more preferably at least 4 times, even more preferably at least 5 times up to preferably 6 times, more preferably up to 7 times or even up to 8, 9 or 10 times, preferably over a time period of at least 10 days, preferably for at least 11 days and more preferably for at least 12 days to ensure expression of one or more factors for an extended period of time. Preferably, the time periods elapsing between the repeated introductions of the RNA are from 24 hours to 120 hours, preferably 48 hours to 96 hours. In one embodiment, time periods elapsing between the repeated introductions of the RNA are not longer than 72 hours, preferably not longer than 48 hours or 36 hours. In one embodiment, prior to the next electroporation, cells are allowed to recover from the previous electroporation. In this embodiment, the time periods elapsing between the repeated introductions of the RNA are at least 72 hours, preferably at least 96 hours, more preferably at least 120 hours. In any case, the conditions should be selected so that the factors are expressed in the cells in amounts and for periods of time which support the reprogramming process. In one embodiment, however, a single introduction of RNA replicons may be sufficient for the reprogramming process and for the development of cells having stem cell characteristics Preferably at least 0.01 µg, preferably at least 0.05 µg, preferably at least 0.1 µg, preferably at least 0.2 µg, more preferably at least 0.3 µg and preferably up to 5 µg, more preferably up to 2 µg, more preferably up to 1 µg, more preferably up to 0.5 µg, preferably 0.05 to 1 µg, even more preferably 0.05 to 0.7 µg, or 0.05 to 0.5 µg of RNA replicon for each factor is used per transfection.

Preferably, the step of allowing the development of cells having stem cell characteristics comprises culturing the somatic cells under embryonic stem cell culture conditions, preferbly conditions suitable for maintaining pluripotent stem cells in an undifferentiated state.

Preferably, to allow the development of cells having stem cell characteristics, cells are cultivated in the presence of one or more DNA methyltransferase inhibitors and/or one or more histone deacetylase inhibitors. Preferred compounds are selected from the group consisting of 5'-azacytidine (5'-azaC), suberoylanilide hydroxamic acid (SAHA), dexamethasone, trichostatin A (TSA), sodium butyrate (NaBu), Scriptaid and valproic acid (VPA). Preferably, cells are cultivated in the presence of valproic acid (VPA), preferably in a concentration of between 0.5 and 10 mM, more preferably between 1 and 5 mM, most preferably in a concentration of about 2 mM.

In a preferred embodiment of the present invention, RNA is introduced into the somatic cells by repeated electroporations. Preferably, if a loss of viability of the cells occurs, previously not electroporated cells are added as carrier cells. Preferably, previously not electroporated cells are added prior to, during or after one or more of the 4th and subsequent, preferably, the 5th and subsequent electroporations such as prior to, during or after the 4th and 6th electroporation. Preferably, previously not electroporated cells are added prior to, during or after the 4th or 5th and each subsequent electroporation. Preferably, the previously not electroporated cells are the same cells as those into which RNA is introduced.

Preferably, introduction of RNA replicons capable of expressing one or more reprogramming factors into a cell causes expression of the one or more reprogramming factors in the cell.

The term "reprogramming factor" according to the invention includes proteins and peptides as well as derivatives and variants thereof inducing optionally together with further agents such as further reprogramming factors the reprogramming of somatic cells to cells having stem cell characteristics. For example, the term "reprogramming factor" comprises OCT4, SOX2, NANOG, LIN28, KLF4 and c-MYC.

The reprogramming factors can be of any animal species; e.g., mammals and rodents. Examples of mammals include but are not limited to human and non-human primates. Primates include but are not limited to humans, chimpanzees, baboons, cynomolgus monkeys, and any other New or Old World monkeys. Rodents include but are not limited to mouse, rat, guinea pig, hamster and gerbil.

In one embodiment of the present invention, reprogramming factors capable of allowing the reprogramming of somatic cells to cells having stem cell characteristics comprise an assembly of factors selected from the group consisting of (i) OCT4 and SOX2, (ii) OCT4, SOX2, and one or both of NANOG and LIN28, (iii) OCT4, SOX2 and one or both of KLF4 and c-MYC. In one embodiment, said reprogramming factors comprise OCT4, SOX2, NANOG and LIN28, OCT4, SOX2, KLF4 and c-MYC, or OCT4, SOX2, KLF4, c-MYC, NANOG and LIN28.

OCT4 is a transcription factor of the eukaryotic POU transcription factors and an indicator of pluripotency of embryonic stem cells. It is a maternally expressed Octomer binding protein. It has been observed to be present in oocytes, the inner cell mass of blastocytes and also in the primordial germ cell. The gene POU5F1 encodes the OCT4 protein. Synonyms to the gene name include OCT3, OCT4, OTF3 and MGC22487. The presence of OCT4 at specific concentrations is necessary for embryonic stem cells to remain undifferentiated. Preferably, "OCT4 protein" or simply "OCT4" relates to human OCT4.

Sox2 is a member of the Sox (SRY-related HMG box) gene family that encode transcription factors with a single HMG DNA-binding domain. SOX2 has been found to control neural progenitor cells by inhibiting their ability to differentiate. The repression of the factor results in delamination from the ventricular zone, which is followed by an exit from the cell cycle. These cells also begin to lose their progenitor character through the loss of progenitor and early neuronal differentiation markers. Preferably, "SOX2 protein" or simply "SOX2" relates to human SOX2.

NANOG is a NK-2 type homeodomain gene, and has been proposed to play a key role in maintaining stem cell pluripotency presumably by regulating the expression of genes critical to embryonic stem cell renewal and differentiation. NANOG behaves as a transcription activator with two unusually strong activation domains embedded in its C terminus. Reduction of NANOG expression induces differentiation of embryonic stem cells. Preferably, "NANOG protein" or simply "NANOG" relates to human NANOG.

LIN28 is a conserved cytoplasmic protein with an unusual pairing of RNA-binding motifs: a cold shock domain and a pair of retroviral-type CCHC zinc fingers. In mammals, it is abundant in diverse types of undifferentiated cells. In pluripotent mammalian cells, LIN28 is observed in RNase-sensitive complexes with Poly(A)-Binding Protein, and in polysomal fractions of sucrose gradients, suggesting it is associated with translating mRNAs. Preferably, "LIN28 protein" or simply "LIN28" relates to human LIN28.

Krueppel-like factor (KLF4) is a zinc-finger transcription factor, which is strongly expressed in postmitotic epithelial cells of different tissues, e.g. the colon, the stomach and the skin. KLF4 is essential for the terminal differentiation of these cells and involved in the cell cycle regulation. Preferably, "KLF4 protein" or simply "KLF4" relates to human KLF4.

MYC (cMYC) is a protooncogene, which is overexpressed in a wide range of human cancers. When it is specifically-mutated, or overexpressed, it increases cell proliferation and functions as an oncogene. MYC gene encodes for a transcription factor that regulates expression of 15% of all genes through binding on Enhancer Box sequences (E-boxes) and recruiting histone acetyltransferases (HATs). MYC belongs to MYC family of transcription factors, which also includes N-MYC and L-MYC genes. MYC-family transcription factors contain the bHLH/LZ (basic Helix-Loop-Helix Leucine Zipper) domain. Preferably, "cMYC protein" or simply "cMYC" relates to human cMYC.

The term "miRNA" (microRNA) relates to 21-23-nucleotide-long noncoding RNAs found in eukaryotic cells that, by inducing degradation and/or preventing translation of target mRNAs, modulate a plethora of cell functions, including those related to ESC self-renewal/differentiation and cell cycle progression. miRNAs are post-transcriptional regulators that bind to complementary sequences on target messenger RNA transcripts (mRNAs), usually resulting in translational repression or target degradation and gene silencing. It has been found that miRNAs in the right combination are capable of inducing direct cellular reprogramming of somatic cells to cells having stem cell characteristics in vitro. For example, it has been observed that miRNA cluster 302-367 (e.g., cluster 302a-d/367) enhances somatic cell reprogramming.

A reference herein to specific factors such as OCT4, SOX2, NANOG, LIN28, KLF4 or c-MYC is to be understood so as to also include all variants of these factors. In particular, it is to be understood so as to also include all splice variants, posttranslationally modified variants, conformations, isoforms and species homologs of these factors which are naturally expressed by cells.

For the purposes of the present invention, "variants" of a protein or peptide or of an amino acid sequence comprise amino acid insertion variants, amino acid deletion variants and/or amino acid substitution variants.

Amino acid insertion variants comprise amino- and/or carboxy-terminal fusions and also insertions of single or two or more amino acids in a particular amino acid sequence. In the case of amino acid sequence variants having an insertion, one or more amino acid residues are inserted into a particular site in an amino acid sequence, although random insertion with appropriate screening of the resulting product is also possible.

Amino acid deletion variants are characterized by the removal of one or more amino acids from the sequence.

Amino acid substitution variants are characterized by at least one residue in the sequence being removed and another residue being inserted in its place. Preference is given to the modifications being in positions in the amino acid sequence which are not conserved between homologous proteins or peptides and/or to replacing amino acids with other ones having similar properties.

"Conservative substitutions" may be made, for instance, on the basis of similarity in polarity, charge, solubility, hydrophobicity, hydrophilicity, and/or the amphipathic nature of the residues involved. For example: (a) nonpolar (hydrophobic) amino acids include alanine, leucine, isoleucine, valine, proline, phenylalanine, tryptophan, and methionine; (b) polar neutral amino acids include glycine, serine, threonine, cysteine, tyrosine, asparagine, and glutamine; (c) positively charged (basic) amino acids include arginine, lysine, and histidine; and (d) negatively charged (acidic) amino acids include aspartic acid and glutamic acid. Substitutions typically may be made within groups (a)-(d). In addition, glycine and proline may be substituted for one another based on their ability to disrupt α-helices. Some preferred substitutions may be made among the following groups: (i) S and T; (ii) P and G; and (iii) A, V, L and I. Given the known genetic code, and recombinant and synthetic DNA techniques, the skilled scientist readily can construct DNAs encoding the conservative amino acid variants.

Preferably the degree of similarity, preferably identity between a specific amino acid sequence described herein and an amino acid sequence which is a variant of said specific amino acid sequence will be at least 70%, preferably at least 80%, preferably at least 85%, even more preferably at least 90% or most preferably at least 95%, 96%, 97%, 98% or 99%. The degree of similarity or identity is given preferably for a region of at least about 20, at least about 40, at least about 60, at least about 80, at least about 100, at least about 120, at least about 140, at least about 160, at least about 200 or 250 amino acids. In preferred embodiments, the degree of similarity or identity is given for the entire length of the reference amino acid sequence.

According to the invention, a variant of a protein or peptide preferably has a functional property of the protein or peptide from which it has been derived. Such functional properties are described above for OCT4, SOX2, NANOG, LIN28, KLF4 and c-MYC, respectively. Preferably, a variant of a protein or peptide has the same property in reprogramming an animal differentiated cell as the protein or peptide from which it has been derived. Preferably, the variant induces or enhances reprogramming of an animal differentiated cell.

The methods of the present invention can be used to effect de-differentiation of any type of somatic cell. Cells that may be used include cells that can be de-differentiated or reprogrammed by the methods of the present invention, in particular cells that are fully or partially differentiated, more preferably terminally differentiated. Preferably, the somatic cell is a diploid cell derived from pre-embryonic, embryonic, fetal, and post-natal multi-cellular organisms. Examples of cells that may be used include but are not limited to fibroblasts, such as fetal and neonatal fibroblasts or adult fibroblasts, keratinocytes, in particular primary keratinocytes, more preferably keratinocytes derived from hair, B cells, T cells, dendritic cells, adipose cells, epithelial cells, epidermal cells, chondrocytes, cumulus cells, neural cells, glial cells, astrocytes, cardiac cells, esophageal cells, muscle cells, melanocytes, hematopoietic cells, osteocytes, macrophages, monocytes, and mononuclear cells. Examples of cells that may be used include blood-derived endothelial cells and endothelial progenitor cells, and urine derived epithelial cells.

The cells with which the methods of the invention can be used can be of any animal species; e.g., mammals and rodents. Examples of mammalian cells that can be de-differentiated and re-differentiated by the present invention include but are not limited to human and non-human primate cells. Primate cells with which the invention may be performed include but are not limited to cells of humans, chimpanzees, baboons, cynomolgus monkeys, and any other New or Old World monkeys. Rodent cells with which the invention may be performed include but are not limited to mouse, rat, guinea pig, hamster and gerbil cells.

The term "organism" according to the invention relates to any biological unit that is capable of multiplying or transmitting genetic material and comprises plants and animals, and microorganisms such as bacteria, yeasts, fungi and viruses. The term "organism" includes but is not limited to a human being, a nonhuman primate or another animal, in particular a mammal such as a cow, horse, pig, sheep, goat, dog, cat or a rodent such as a mouse and rat. In a particularly preferred embodiment, the organism is a human being.

De-differentiated cells prepared according to the present invention are expected to display many of the same requirements as pluripotent stem cells and can be expanded and maintained under conditions used for embryonic stem cells, e.g. ES cell medium or any medium that supports growth of the embryonic cells. Embryonic stem cells retain their pluripotency in vitro when maintained on inactivated fetal fibroblasts such as irradiated mouse embryonic fibroblasts or human fibroblasts (e.g., human foreskin fibroblasts, human skin fibroblasts, human endometrial fibroblasts, human oviductal fibroblasts) in culture. In one embodiment, the human feeder cells may be autologous feeder cells derived from the same culture of reprogrammed cells by direct differentiation.

Furthermore, human embryonic stem cells can successfully be propagated on Matrigel in a medium conditioned by mouse fetal fibroblasts. Human stem cells can be grown in culture for extended period of time and remain undifferentiated under specific culture conditions.

In certain embodiments, the cell culture conditions may include contacting the cells with factors that can inhibit differentiation or otherwise potentiate de-differentiation of cells, e.g., prevent the differentiation of cells into non-ES cells, trophectoderm or other cell types.

De-differentiated cells prepared according to the present invention can be evaluated by methods including monitoring changes in the cells' phenotype and characterizing their gene and protein expression. Gene expression can be determined by RT-PCR, and translation products can be determined by immunocytochemistry and Western blotting. In particular, de-differentiated cells can be characterized to determine the pattern of gene expression and whether the reprogrammed cells display a pattern of gene expression similar to the expression pattern expected of undifferentiated, pluripotent control cells such as embryonic stem cells using techniques well known in the art including transcriptomics.

The expression of the following genes of de-differentiated cells can be assessed in this respect: OCT4, NANOG, LIN28, growth and differentiation factor 3 (GDF3), reduced expression 1 (REX1), fibroblast growth factor 4 (FGF4), embryonic cell-specific gene 1 (ESG1), developmental pluripotency-associated 2 (DPPA2), DPPA4, telomerase reverse transcriptase (TERT), embryonic antigen-3 (SSEA-3), SSEA-4, tumor-related antigen-1-60 (TRA-1-60), TRA-1-81, and TRA-2-49/6E.

The undifferentiated or embryonic stem cells to which the reprogrammed cells may be compared may be from the same species as the differentiated somatic cells. Alternatively, the undifferentiated or embryonic stem cells to which the reprogrammed cells may be compared may be from a different species as the differentiated somatic cells.

In some embodiments, a similarity in gene expression pattern exists between a reprogrammed cell and an undifferentiated cell, e.g., embryonic stem cell, if certain genes specifically expressed in an undifferentiated cell are also expressed in the reprogrammed cell. For example, certain genes, e.g., telomerase, that are typically undetectable in differentiated somatic cells may be used to monitor the extent of reprogramming. Likewise, for certain genes, the absence of expression may be used to assess the extent of reprogramming.

Self-renewing capacity, marked by induction of telomerase activity, is another characteristic of stem cells that can be monitored in de-differentiated cells.

Karyotypic analysis may be performed by means of chromosome spreads from mitotic cells, spectral karyotyping, assays of telomere length, total genomic hybridization, or other techniques well known in the art.

At Least One Open Reading Frame Comprised by the Replicon

The RNA replicon according to the present invention comprises as an open reading frame encoding a peptide of interest or a protein of interest an open reading frame encoding a reprogramming factor and may comprise one or more further open reading frames encoding a peptide of interest or a protein of interest such as one or more further reprogramming factors forming together with the first reprogramming factor a functional set of reprogramming factors. Preferably, the protein of interest is encoded by a heterologous nucleic acid sequence. The gene encoding the peptide or protein of interest is synonymously termed "gene of interest" or "transgene". In various embodiments, the peptide or protein of interest is encoded by a heterologous nucleic acid sequence. According to the present invention, the term "heterologous" refers to the fact that a nucleic acid sequence is not naturally functionally or structurally linked to an alphavirus nucleic acid sequence. The replicon according to the present invention may encode a single polypeptide, i.e., a reprogramming factor, or multiple polypeptides such as multiple reprogramming factors or a reprogramming factor and another polypeptide. Multiple polypeptides can be encoded as a single polypeptide (fusion polypeptide) or as separate polypeptides. In some embodiments, the replicon according to the present invention may comprise more than one open reading frames, each of which may independently be selected to be under the control of a subgenomic promoter or not. Alternatively, a poly-protein or fusion polypeptide comprises individual polypeptides separated by an optionally autocatalytic protease cleavage site (e.g. foot-and-mouth disease virus 2A protein), or an intein.

Proteins of interest may e.g. be selected from the group consisting of reporter proteins, pharmaceutically active peptides or proteins, inhibitors of the engagement of IFN receptor by extracellular IFN, inhibitors of intracellular interferon (IFN) signaling, and functional alphavirus non-structural protein.

Inhibitor of Interferon (IFN) Signaling

A further suitable protein of interest encoded by an open reading frame is an inhibitor of interferon (IFN) signaling. While it has been reported that viability of cells in which RNA has been introduced for expression can be reduced, in particular, if cells are transfected multiple times with RNA, IFN inhibiting agents were found to enhance the viability of cells in which RNA is to be expressed (WO 2014/071963 A1). Preferably, the inhibitor is an inhibitor of IFN type I signaling. Preventing engagement of IFN receptor by extracellular IFN and/or inhibiting intracellular IFN signaling in the cells allows stable expression of RNA in the cells. Alternatively or additionally, preventing engagement of IFN receptor by extracellular IFN and/or inhibiting intracellular IFN signaling enhances survival of the cells, in particular, if cells are transfected repetitively with RNA.

In one embodiment, preventing engagement of IFN receptor by extracellular IFN comprises providing a binding agent for extracellular IFN such as a viral binding agent for extracellular IFN. In one embodiment, the viral binding agent for extracellular IFN is a viral interferon receptor. In one embodiment, the viral binding agent for extracellular IFN is vaccinia virus B18R. The B18R protein is a vaccinia virus-encoded type I interferon receptor with specificity for mouse, human, rabbit, pig, rat, and cow type I interferons which has potent neutralizing activity. The B18R protein encoded by the B18R gene of the Western Reserve vaccinia virus strain. The 60-65 kD glycoprotein is related to the interleukin-1 receptors and is a member of the immunoglobulin superfamily, unlike other type I IFN-receptors, which belong to the class II cytokine receptor family. The B18R protein has a high affinity (KD, 174 pM) for human IFN alpha. Among viral host response modifiers, the B18R protein is unique in that it exists as a soluble extracellular, as well as a cell surface protein, enabling blockage of both autocrine and paracrine IFN functions.

Without wishing to be bound by theory, it is envisaged that intracellular IFN signalling can result in inhibition of translation and/or RNA degradation. This can be addressed by inhibiting one or more IFN-inducible antivirally active effector proteins. The IFN-inducible antivirally active effector protein can be selected from the group consisting of RNA-dependent protein kinase (PKR), 2',5'-oligoadenylate synthetase (OAS) and RNaseL. Inhibiting intracellular IFN signalling may comprise inhibiting the PKR-dependent pathway and/or the OAS-dependent pathway. A suitable protein of interest is a protein that is capable of inhibiting the PKR-dependent pathway and/or the OAS-dependent pathway. Inhibiting the PKR-dependent pathway may comprise inhibiting eIF2-alpha phosphorylation. Inhibiting PKR may comprise treating the cell with at least one PKR inhibitor. The PKR inhibitor may be a viral inhibitor of PKR. The preferred viral inhibitor of PKR is vaccinia virus E3. If a peptide or protein (e.g. E3, K3) is to inhibit intracellular IFN signaling, intracellular expression of the peptide or protein is preferred. Vaccinia virus E3 is a 25 kDa dsRNA-binding protein (encoded by gene E3L) that binds and sequesters dsRNA to prevent the activation of PKR and OAS. E3 can bind directly to PKR and inhibits its activity, resulting in reduced phosphorylation of eIF2-alpha. Vaccinia virus gene K3L encodes a 10.5 kDa homolog of the eIF2-alpha subunit that acts as a non-phosphorylable pseudosubstrate of PKR and competitively inhibits phosphorylation of eIF2-alpha.

Other suitable inhibitors of IFN signaling are Herpes simplex virus ICP34.5, Toscana virus NSs, *Bombyx mori* nucleopolyhedrovirus PK2, and HCV NS34A.

In one embodiment, the present invention may comprise providing a cells with vaccinia virus B18R or a functional variant thereof and vaccinia virus E3 or a functional variant thereof or vaccinia virus K3 or a functional variant thereof, or both. The viral escape protein NSs (N) from Toscana virus is a potent inhibitor of IFN-response and can be used to substitute EKB (E3, K3, B18R) for successful RNA-based reprogramming The inhibitor of IFN signaling may be provided to the cell in the form of a nucleic acid sequence (e.g. RNA) encoding the inhibitor of IFN signaling.

In one embodiment, the inhibitor of intracellular or extracellular IFN signaling is encoded by an mRNA molecule. That mRNA molecule may comprise a non-polypeptide-sequence modifying modification as described herein, e.g. cap, 5'-UTR, 3'-UTR, poly(A) sequence, adaptation of the codon usage.

In an alternative embodiment, the inhibitor of intracellular or extracellular IFN signaling is encoded by a replicon, preferably a trans-replicon or a trans-replicon as described herein. The replicon comprises nucleic acid sequehce elements that allow replication by alphavirus replicase, typically CSE 1, CSE 2 and CSE 4; and preferably also nucleic acid sequence elements that allow production of a subgenomic transcript, i.e. a subgenomic promoter, typically comprising CSE 3. The replicon may additionally comprise one or more non-polypeptide-sequence modifying modifications as described herein, e.g. cap, poly(A) sequence, adaptation of the codon usage. If multiple open reading frames are present on the replicon, then an inhibitor of IFN signaling may be encoded by any one of them, optionally under control of a subgenomic promoter or not. In a preferred embodiment, the inhibitor of IFN signaling is encoded by the most upstream open reading frame of the RNA replicon. When an inhibitor of IFN signaling is encoded by the most upstream open reading frame of the RNA replicon, the genetic information encoding the inhibitor of IFN signaling will be translated early after introduction of the RNA replicon into a host cell, and the resulting protein may subsequently inhibit IFN signaling.

Functional Alphavirus Non-Structural Protein

A further suitable protein of interest encoded by an open reading frame is functional alphavirus non-structural protein. The term "alphavirus non-structural protein" includes each and every co- or post-translationally modified form, including carbohydrate-modified (such as glycosylated) and lipid-modified forms of alphavirus non-structural protein.

In some embodiments, the term "aiphavirus non-structural protein" refers to any one or more of individual non-structural proteins of alphavirus origin (nsP1, nsP2, nsP3, nsP4), or to a poly-protein comprising the polypeptide sequence of more than one non-structural protein of alphavirus origin. In some embodiments, "aiphavirus non-structural protein" refers to nsP123 and/or to nsP4. In other embodiments, "alphavirus non-structural protein" refers to nsP1234. In one embodiment, the protein of interest encoded by an open reading frame consists of all of nsP1, nsP2, nsP3 and nsP4 as one single, optionally cleavable poly-protein: nsP1234. In one embodiment, the protein of interest encoded by an open reading frame consists of nsP1, nsP2 and nsP3 as one single, optionally cleavable polyprotein: nsP123. In that embodiment, nsP4 may be a further protein of interest and may be encoded by a further open reading frame.

In some embodiments, aiphavirus non-structural protein is capable of forming a complex or association, e.g. in a host cell. In some embodiments, "alphavirus non-structural protein" refers to a complex or association of nsP123 (synonymously P123) and nsP4. In some embodiments, "alphavirus non-structural protein" refers to a complex or association of nsP1, nsP2, and nsP3. In some embodiments, "alphavirus non-structural protein" refers to a complex or association of nsP1, nsP2, nsP3 and nsP4. In some embodiments, "alphavirus non-structural protein" refers to a complex or association of any one or more selected from the group consisting of nsP1, nsP2, nsP3 and nsP4. In some embodiments, the alphavirus non-structural protein comprises at least nsP4.

The terms "complex" or "association" refer to two or more same or different protein molecules that are in spatial proximity. Proteins of a complex are preferably in direct or indirect physical or physicochemical contact with each other. A complex or association can consist of multiple different proteins (heteromultimer) and/or of multiple copies of one particular protein (homomultimer). In the context of alphavirus non-structural protein, the term "complex or association" describes a multitude of at least two protein molecules, of which at least one is an aiphavirus non-structural protein. The complex or association can consist of multiple copies of one particular protein (homomultimer) and/or of multiple different proteins (heteromultimer). In the context of a multimer, "multi" means more than one, such as two, three, four, five, six, seven, eight, nine, ten, or more than ten.

The term "functional aiphavirus non-structural protein" includes alphavirus non-structural protein that has replicase function. Thus, "functional alphavirus non-structural protein" includes alphavirus replicase. "Replicase function" comprises the function of an RNA-dependent RNA polymerase (RdRP), i.e. an enzyme which is capable to catalyze the synthesis of (−) strand RNA based on a (+) strand RNA template, and/or which is capable to catalyze the synthesis of (+) strand RNA based on a (−) strand RNA template. Thus, the term "functional alphavirus non-structural protein" can refer to a protein or complex that synthesizes (−) stranded RNA, using the (+) stranded (e.g. genomic) RNA as template, to a protein or complex that synthesizes new (+) stranded RNA, using the (−) stranded complement of genomic RNA as template, and/or to a protein or complex that synthesizes a subgenomic transcript, using a fragment of the (−) stranded complement of genomic RNA as template. The functional alphavirus non-structural protein may additionally have one or more additional functions, such as e.g. a protease (for auto-cleavage), helicase, terminal adenylyltransferase (for poly(A) tail addition), methyltransferase and guanylyltransferase (for providing a nucleic acid with a 5′-cap), nuclear localization sites, triphosphatase (Gould et al., 2010, Antiviral Res., vol. 87 pp. 111-124; Rupp et al., 2015, J. Gen. Virol., vol. 96, pp. 2483-500).

According to the invention, the term "alphavirus replicase" refers to alphaviral RNA-dependent RNA polymerase, including a RNA-dependent RNA polymerase from a naturally occurring alphavirus (alphavirus found in nature) and a RNA-dependent RNA polymerase from a variant or derivative of an alphavirus, such as from an attenuated alphavirus. In the context of the present invention, the terms "replicase" and "alphavirus replicase" are used interchangeably, unless the context dictates that any particular replicase is not an alphavirus replicase.

The term "replicase" comprises all variants, in particular post-translationally modified variants, conformations, isoforms and homologs of alphavirus replicase, which are expressed by alphavirus-infected cells or which are expressed by cells that have been transfected with a nucleic acid that codes for alphavirus replicase. Moreover, the term "replicase" comprises all forms of replicase that have been produced and can be produced by recombinant methods. For example, a replicase comprising a tag that facilitates detection and/or purification of the replicase in the laboratory, e.g. a myc-tag, a HA-tag or an oligohistidine tag (His-tag) may be produced by recombinant methods.

Optionally, the alphavirus replicase is additionally functionally defined by the capacity of binding to any one or more of alphavirus conserved sequence element 1 (CSE 1) or complementary sequence thereof, conserved sequence element 2 (CSE 2) or complementary sequence thereof, conserved sequence element 3 (CSE 3) or complementary sequence thereof, conserved sequence element 4 (CSE 4) or complementary sequence thereof. Preferably, the replicase is capable of binding to CSE 2 [i.e. to the (+) strand] and/or to CSE 4 [i.e. to the (+) strand], or of binding to the complement of CSE 1 [i.e. to the (−) strand] and/or to the complement of CSE 3 [i.e. to the (−) strand].

The origin of the replicase is not limited to any particular alphavirus. In a preferred embodiment, the alphavirus replicase comprises non-structural protein from Semliki Forest virus, including a naturally occurring Semliki Forest virus and a variant or derivative of Semliki Forest virus, such as an attenuated Semliki Forest virus. In an alternative preferred embodiment, the alphavirus replicase comprises non-structural protein from Sindbis virus, including a naturally occurring Sindbis virus and a variant or derivative of Sindbis virus, such as an attenuated Sindbis virus. In an alternative preferred embodiment, the alphavirus replicase comprises non-structural protein from Venezuelan equine encephalitis virus (VEEV), including a naturally occurring VEEV and a variant or derivative of VEEV, such as an attenuated VEEV. In an alternative preferred embodiment, the alphavirus replicase comprises non-structural protein from chikungunya virus (CHIKV), including a naturally occurring CHIKV and a variant or derivative of CHIKV, such as an attenuated CHIKV.

A replicase can also comprise non-structural proteins from more than one alphavirus. Thus, heterologous complexes or associations comprising alphavirus non-structural protein and having replicase function are equally comprised by the present invention. Merely for illustrative purposes, replicase may comprise one or more non-structural proteins (e.g. nsP1, nsP2) from a first alphavirus, and one or more non-structural proteins (nsP3, nsP4) from a second alphavirus. Non-structural proteins from more than one different alphavirus may be encoded by separate open reading frames, or may be encoded by a single open reading frame as poly-protein, e.g. nsP1234.

In some embodiments, functional alphavirus non-structural protein is capable of forming membranous replication complexes and/or vacuoles in cells in which the functional alphavirus non-structural protein is expressed.

If functional alphavirus non-structural protein, i.e. alphavirus non-structural protein with replicase function, is encoded by a nucleic acid molecule according to the present invention, it is preferable that the subgenomic promoter of the replicon, if present, is compatible with said replicase. Compatible in this context means that the alphavirus replicase is capable of recognizing the subgenomic promoter, if present. In one embodiment, this is achieved when the subgenomic promoter is native to the alphavirus from which the replicase is derived, i.e. the natural origin of these sequences is the same alphavirus. In an alternative embodiment, the subgenomic promoter is not native to the alphavirus from which the alphavirus replicase is derived, provided that the alphavirus replicase is capable of recognizing the subgenomic promoter. In other words, the replicase is compatible with the subgenomic promoter (cross-virus compatibility). Examples of cross-virus compatibility concerning subgenomic promoter and replicase originating from different alphaviruses are known in the art. Any combination of subgenomic promoter and replicase is possible as long as cross-virus compatibility exists. Cross-virus compatibility can readily be tested by the skilled person working the present invention by incubating a replicase to be tested together with an RNA, wherein the RNA has a subgenomic promoter to be tested, at conditions suitable for RNA synthesis from the a subgenomic promoter. If a subgenomic transcript is prepared, the subgenomic promoter and the replicase are determined to be compatible. Various examples of cross-virus compatibility are known (reviewed by Strauss & Strauss, Microbiol. Rev., 1994, vol. 58, pp. 491-562).

In one embodiment, alphavirus non-structural protein is not encoded as fusion protein with a heterologous protein, e.g. ubiquitin.

In the present invention, an open reading frame encoding functional alphavirus non-structural protein can be provided on the RNA replicon, or alternatively, can be provided as separate nucleic acid molecule, e.g. mRNA molecule. A separate mRNA molecule may optionally comprise e.g. cap, 5'-UTR, 3'-UTR, poly(A) sequence, and/or adaptation of the codon usage. The separate mRNA molecule may be provided in trans, as described herein for the system of the present invention.

Figure 5:
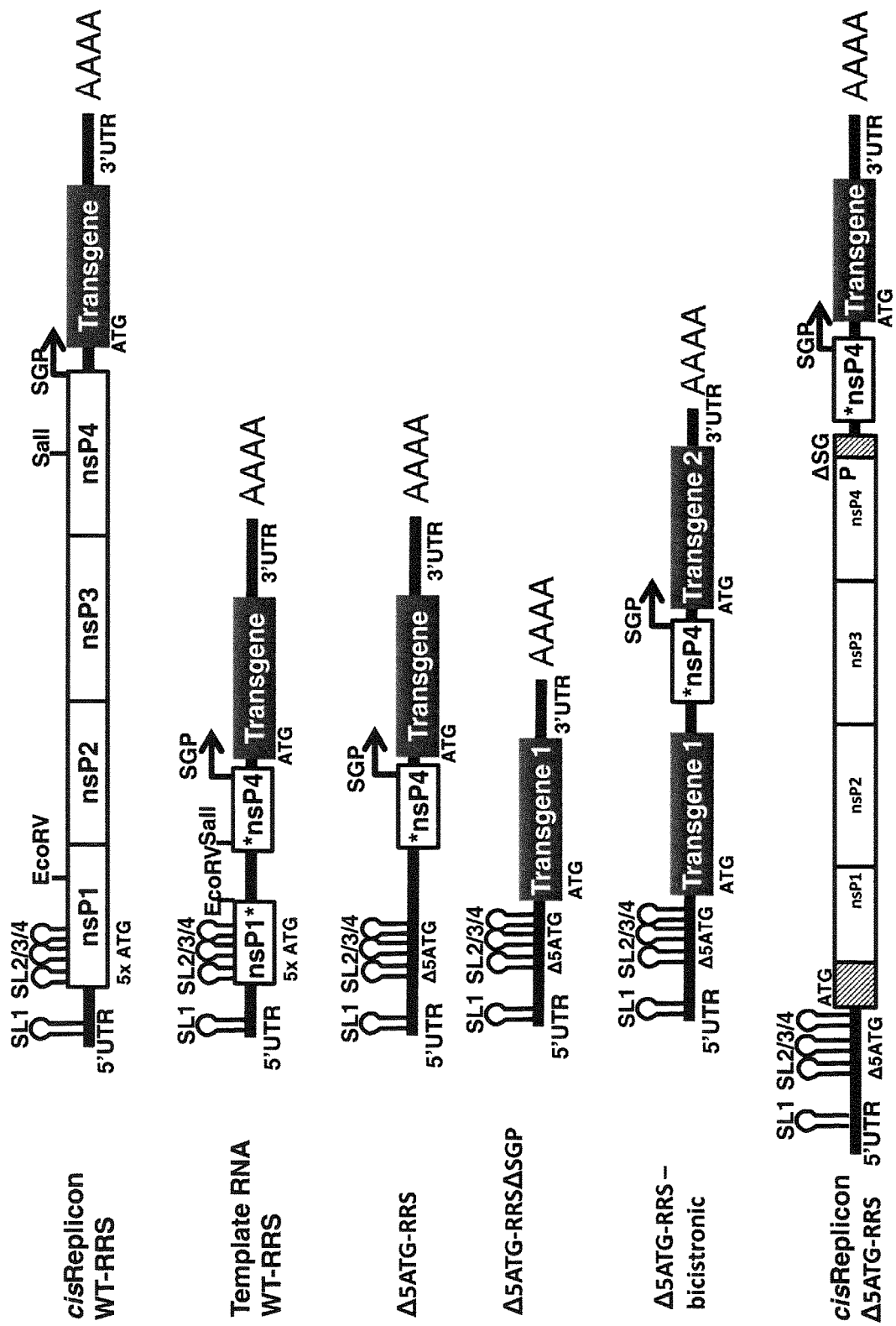
FIG. 5: Schematic representation of RNA replicons comprising an unmodified or a modified 5' replication recognition sequence useful according to the invention Abbreviations: AAAA=Poly(A) tail; ATG=start codon/initiation codon (ATG on DNA level; AUG on RNA level); 5×ATG=nucleic acid sequence comprising all start codons in the nucleic acid sequence encoding nsP1* (in the case of the nucleic acid sequence encoding nsP1* from Semliki Forest virus 5×ATG corresponds to five specific start codons); Δ5ATG=nucleic acid sequence corresponding to a nucleic acid sequence encoding nsP1*; however not comprising any start codons of the nucleic acid sequence that encodes nsP1* in alphavirus found in nature (in the case of nsP1* derived from Semliki Forest virus, "Δ5ATG" corresponds to the removal of five specific start codons compared to Semliki Forest virus found in nature); EcoRV=EcoRV restriction site; nsP=nucleic acid sequence encoding an alphavirus non-structural protein (e.g. nsP1, nsP2, nsP3, nsP4); nsP1*=nucleic acid sequence encoding a fragment of nsP1, wherein the fragment does not comprise the C-terminal fragment of nsP1; *nsP4=nucleic acid sequence encoding a fragment of nsP4, wherein the 'fragment does not comprise the N-terminal fragment of nsP4; RRS=5' replication recognition sequence; SalI=SalI restriction site; SGP=subgenomic promoter; SL=stem loop (e.g. SL1, SL2, SL3, SL4); the positions of SL1-4 are graphically illustrated; UTR=untranslated region (e.g. 5'-UTR, 3'-UTR); WT=wild type; Transgene preferably relates to an open reading frame encoding a reprogramming factor.

When an open reading frame encoding functional alphavirus non-structural protein is provided on the RNA replicon, the replicon can preferably be replicated by the functional alphavirus non-structural protein. In particular, the RNA replicon that encodes functional alphavirus non-structural protein can be replicated by the functional alphavirus non-structural protein encoded by the replicon. This embodiment is strongly preferred when no nucleic acid molecule encoding functional alphavirus non-structural protein is provided in trans. In this embodiment, cis-replication of the replicon is aimed at. In a preferred embodiment, the RNA replicon comprises an open reading frame encoding functional alphavirus non-structural protein as well as a further open reading frame encoding a protein of interest, and can be replicated by the functional alphavirus non-structural protein. This embodiment is particularly suitable in some methods for producing a protein of interest according to the present invention. An example of a respective replicon is illustrated in FIG. 5 ("cisReplicon Δ5ATG-RRS").

If the replicon comprises an open reading frame encoding functional alphavirus non-structural protein, it is preferable that the open reading frame encoding functional alphavirus non-structural protein does not overlap with the 5' replication recognition sequence. In one embodiment, the open reading frame encoding functional alphavirus non-structural protein does not overlap with the subgenomic promoter, if present. An example of a respective replicon is illustrated in FIG. 5 ("cisReplicon Δ5ATG-RRS").

If multiple open reading frames are present on the replicon, then the functional alphavirus non-structural protein may be encoded by any one of them, optionally under control of a subgenomic promoter or not, preferably not under control of a subgenomic promoter. In a preferred embodiment, the functional alphavirus non-structural protein is encoded by the most upstream open reading frame of the RNA replicon. When the functional alphavirus non-structural protein is encoded by the most upstream open reading frame of the RNA replicon, the genetic information encoding functional alphavirus non-structural protein will be translated early after introduction of the RNA replicon into a host cell, and the resulting protein can subsequently drive replication, and optionally production of a subgenomic transcript, in the host cell. An example of a respective replicon is illustrated in FIG. 5 ("cisReplicon Δ5ATG-RRS").

Presence of an open reading frame encoding functional alphavirus non-structural protein, either comprised by the replicon or comprised by a separate nucleic acid molecule that is provided in trans, allows that the replicon is replicated, and consequently, that a gene of interest encoded by the replicon, optionally under control of a subgenomic promoter, is expressed at high levels. This is associated with a cost advantage compared to other transgene expression systems. Since the replicon of the present invention can be replicated in the presence of functional alphavirus non-structural protein, high levels of expression of a gene of interest may be achieved even if relatively low amounts replicon RNA are administered. The low amounts of replicon RNA positively influence the costs.

Position of the at Least One Open Reading Frame in the RNA Replicon

The RNA replicon is suitable for expression of one or more genes encoding a peptide of interest or a protein of interest, optionally under control of a subgenomic promoter. Various embodiments are possible. One or more open reading frames, each encoding a peptide of interest or a protein of interest, can be present on the RNA replicon. The most upstream open reading frame of the RNA replicon is referred to as "first open reading frame". In some embodiments, the "first open reading frame" is the only open reading frame of the RNA replicon. Optionally, one or more further open reading frames can be present downstream of the first open reading frame. One or more further open reading frames downstream of the first open reading frame may be referred to as "second open reading frame", "third open reading frame" and so on, in the order (5' to 3') in which they are present downstream of the first open reading frame. Preferably, each open reading frame comprises a start codon (base triplet), typically AUG (in the RNA molecule), corresponding to ATG (in a respective DNA molecule).

If the replicon comprises a 3' replication recognition sequence, it is preferred that all open reading frames are localized upstream of the 3' replication recognition sequence.

When the RNA replicon comprising one or more open reading frames is introduced into a host cell, translation is preferably not initiated at any position upstream of the first open reading frame, owing to the removal of at least one initiation codon from the 5' replication recognition sequence. Therefore, the replicon may serve directly as template for translation of the first open reading frame. Preferably, the replicon comprises a 5'-cap. This is helpful for expression of the gene encoded by the first open reading frame directly from the replicon.

In some embodiments, at least one open reading frame of the replicon is under the control of a subgenomic promoter, preferably an alphavirus subgenomic promoter. The alphavirus subgenomic promoter is very efficient, and is therefore suitable for heterologous gene expression at high levels. Preferably, the subgenomic promoter is a promoter for a subgenomic transcript in an alphavirus. This means that the subgenomic promoter is one which is native to an alphavirus and which preferably controls transcription of the open reading frame encoding one or more structural proteins in said alphavirus. Alternatively, the subgenomic promoter is a variant of a subgenomic promoter of an alphavirus; any variant which functions as promoter for subgenomic RNA transcription in a host cell is suitable. If the replicon comprises a subgenomic promoter, it is preferred that the replicon comprises a conserved sequence element 3 (CSE 3) or a variant thereof.

Preferably, the at least one open reading frame under control of a subgenomic promoter is localized downstream of the subgenomic promoter. Preferably, the subgenomic promoter controls production of subgenomic RNA comprising a transcript of the open reading frame In some embodiments the first open reading frame is under control of a subgenomic promoter. When the first open reading frame is under control of a subgenomic promoter, its localization resembles the localization of the open reading frame encoding structural proteins in the genome of an alphavirus. When the first open reading frame is under control of the subgenomic promoter, the gene encoded by the first open reading frame can be expressed both from the replicon as well as from a subgenomic transcript thereof (the latter in the presence of functional alphavirus non-structural protein). A respective embodiment is exemplified by the replicon "Δ5ATG-RRS" in FIG. 5. Preferably "Δ5ATG-RRS" does not comprise any initiation codon in the nucleic acid sequence encoding the C-terminal fragment of nsP4 (*nsP4). One or more further open reading frames, each under control of a subgenomic promoter, may be present downstream of the first open reading frame that is under control of a subgenomic promoter (not illustrated in FIG. 5). The genes encoded by the one or more further open reading frames, e.g. by the second open reading frame, may be translated from one or more subgenomic transcripts, each under control of a subgenomic promoter. For example, the RNA replicon may comprise a subgenomic promoter controlling production of a transcript that encodes a second protein of interest.

In other embodiments the first open reading frame is not under control of a subgenomic promoter. When the first open reading frame is not under control of a subgenomic promoter, the gene encoded by the first open reading frame can be expressed from the replicon. A respective embodiment is exemplified by the replicon "Δ5ATG-RRSΔSGP" in FIG. 5. One or more further open reading frames, each under control of a subgenomic promoter, may be present downstream of the first open reading frame (for illustration of two exemplary embodiments, see "Δ5ATG-RRS-bicistronic" and "cisReplicon Δ5ATG-RRS" in FIG. 5). The genes encoded by the one or more further open reading frames may be expressed from subgenomic transcripts.

In a cell which comprises the replicon according to the present invention, the replicon may be amplified by functional alphavirus non-structural protein. Additionally, if the replicon comprises one or more open reading frames under control of a subgenomic promoter, one or more subgenomic transcripts are expected to be prepared by functional alphavirus non-structural protein. Functional alphavirus non-structural protein may be provided in trans, or may be encoded by an open reading frame of the replicon.

If a replicon comprises more than one open reading frame encoding a protein of interest, it is preferable that each open reading frame encodes a different protein. For example, the protein encoded by the second open reading frame is different from the protein encoded by the first open reading frame.

In some embodiments, the protein of interest encoded by the first and/or a further open reading frame, preferably by the first open reading frame, is functional alphavirus non-structural protein. In some embodiments, the protein of interest encoded by the first and/or a further open reading frame, e.g. by the second open reading frame, is a reprogramming factor.

In one embodiment, the protein of interest encoded by the first open reading frame is functional alphavirus non-structural protein. In that embodiment the replicon preferably comprises a 5'-cap. Particularly when the protein of interest encoded by the first open reading frame is functional alphavirus non-structural protein, and preferably when the replicon comprises a 5'-cap, the nucleic acid sequence encoding functional alphavirus non-structural protein can be efficiently translated from the replicon, and the resulting protein can subsequently drive replication of the replicon and drive synthesis of subgenomic transcript(s). This embodiment may be preferred when no additional nucleic acid molecule encoding functional alphavirus non-structural protein is used or present together with the replicon. In this embodiment, cis-replication of the replicon is aimed at.

One embodiment wherein the first open reading frame encodes functional alphavirus non-structural protein is illustrated by "cisReplicon Δ5ATG-RRS" in FIG. 5. Following translation of the nucleic acid sequence encoding nsP1234, the translation product (nsP1234 or fragment(s) thereof) can act as replicase and drive RNA synthesis, i.e. replication of the replicon and synthesis of a subgenomic transcript comprising the second open reading frame ("Transgene" in FIG. 5).

Trans-Replication System

In a further aspect, the present invention provides a system comprising:

a RNA construct for expressing functional alphavirus non-structural protein, the RNA replicon according to the first aspect of the invention, which can be replicated by the functional alphavirus non-structural protein in trans.

In this aspect it is preferred that the RNA replicon does not comprise an open reading frame encoding functional alphavirus non-structural protein.

Thus, the present invention provides a system comprising two nucleic acid molecules: a first RNA construct for expressing functional alphavirus non-structural protein (i.e. encoding functional alphavirus non-structural protein); and a second RNA molecule, the RNA replicon. The RNA construct for expressing functional alphavirus non-structural protein is synonymously referred to herein as "RNA construct for expressing functional alphavirus non-structural protein" or as "replicase construct".

The functional alphavirus non-structural protein is as defined above and is typically encoded by an open reading frame comprised by the replicase construct. The functional alphavirus non-structural protein encoded by the replicase construct may be any functional alphavirus non-structural protein that is capable of replicating the replicon.

When the system of the present invention is introduced into a cell, preferably a eukaryotic cell, the open reading frame encoding functional alphavirus non-structural protein can be translated. After translation, the functional alphavirus non-structural protein is capable of replicating a separate RNA molecule (RNA replicon) in trans. Thus, the present invention provides a system for replicating RNA in trans. Consequently, the system of the present invention is a trans-replication system. According to the second aspect, the replicon is a trans-replicon.

Herein, trans (e.g. in the context of trans-acting, trans-regulatory), in general, means "acting from a different molecule" (i.e., intermolecular). It is the opposite of cis (e.g. in the context of cis-acting, cis-regulatory), which, in general, means "acting from the same molecule" (i.e., intramolecular). In the context of RNA synthesis (including transcription and RNA replication), a trans-acting element includes a nucleic acid sequence that contains a gene encoding an enzyme capable of RNA synthesis (RNA polymerase). The RNA polymerase uses a second nucleic acid molecule, i.e. a nucleic acid molecule other than the one by which it is encoded, as template for the synthesis of RNA. Both the RNA polymerase and the nucleic acid sequence that contains a gene encoding the RNA polymerase are said to "act in trans" on the second nucleic acid molecule. In the context of the present invention, the RNA polymerase encoded by the trans-acting RNA is functional alphavirus non-structural protein. The functional alphavirus non-structural protein is capable of using a second nucleic acid molecule, which is an RNA replicon, as template for the synthesis or RNA, including replication of the RNA replicon. The RNA replicon that can be replicated by the replicase in trans according to the present invention is synonymously referred to herein as "trans-replicon".

In the system of the present invention, the role of the functional alphavirus non-structural protein is to amplify the replicon, and to prepare a subgenomic transcript, if a subgenomic promoter is present on the replicon. If the replicon encodes a gene of interest for expression, the expression levels of the gene of interest and/or the duration of expression may be regulated in trans by modifying the levels of the functional alphavirus non-structural protein.

The fact that alphaviral replicase is generally able to recognize and replicate a template RNA in trans was initially discovered in the 1980s, but the potential of trans-replication for biomedical applications was not recognized, inter alia because trans-replicated RNA was considered to inhibit efficient replication: it was discovered in the case of defective interfering (DI) RNA that co-replicates with alphaviral genomes in infected cells (Barrett et al., 1984, J. Gen. Virol., vol. 65 (Pt 8), pp. 1273-1283; Lehtovaara et al., 1981, Proc. Natl. Acad. Sci. U. S. A, vol. 78, pp. 5353-5357; Pettersson, 1981, Proc. Natl. Acad. Sci. U. S. A, vol. 78, pp. 115-119). DI RNAs are trans-replicons that may occur quasi-naturally during infections of cell lines with high virus load. DI elements co-replicate so efficiently that they reduce the virulence of the parental virus and thereby act as inhibitory parasitic RNA (Barrett et al., 1984, J. Gen. Virol., vol. 65 (Pt 11), pp. 1909-1920). Although the potential for biomedical applications was not recognized, the phenomenon of trans-replication was used in several basic studies aiming to elucidate mechanisms of replication, without requiring to express the replicase from the same molecule in cis; further, the separation of replicase and replicon also allows functional studies involving mutants of viral proteins, even if respective mutants were loss-of-function mutants (Lemm et al., 1994, EMBO J., vol. 13, pp. 2925-2934). These loss-of function studies and DI RNA did not suggest that trans-activation systems based on alphaviral elements may eventually become available to suit therapeutic purposes.

The system of the present invention comprises at least two nucleic acid molecules. Thus, it may comprise two or more, three or more, four or more, five or more, six or more, seven or more, eight or more, nine or more, or ten or more nucleic acid molecules, which are preferably RNA molecules. In a preferred embodiment, the system consists of exactly two RNA molecules, the replicon and the replicase construct. In alternative preferred embodiments, the system comprises more than one replicon, each preferably encoding at least one protein of interest, and also comprises the replicase construct. In these embodiments, the functional alphavirus non-structural protein encoded by the replicase construct can act on each replicon to drive replication and production of subgenomic transcripts, respectively. For example, each replicon may encode a reprogramming factor. This is advantageous e.g. if expression of more than one reprogramming factor in a cell is desired so as to form a functional set of reprogramming factors.

Preferably, the replicase construct lacks at least one conserved sequence element (CSE) that is required for (−) strand synthesis based on a (+) strand template, and/or for (+) strand synthesis based on a (−) strand template. More preferably, the replicase construct does not comprise any alphaviral conserved sequence elements (CSEs). In particular, among the four CSEs of alphavirus (Strauss & Strauss, Microbial. Rev., 1994, vol. 58, pp. 491-562; José et al., Future Microbiol., 2009, vol. 4, pp. 837-856), any one or more of the following CSEs are preferably not present on the replicase construct: CSE 1; CSE 2; CSE 3; CSE 4. Particularly in the absence of any one or more alphaviral CSE, the replicase construct of the present invention resembles typical eukaryotic mRNA much more than it resembles alphaviral genomic RNA.

The replicase construct of the present invention is preferably distinguished from alphaviral genomic RNA at least in that it is not capable of self-replication and/or that it does not comprise an open reading frame under the control of a sub-genomic promoter. When unable to self-replicate, the replicase construct may also be termed "suicide construct".

The trans-replication system is associated with the following advantages:

First and foremost, the versatility of the trans-replication system allows that replicon and replicase construct can be designed and/or prepared at different times and/or at different sites. In one embodiment, the replicase construct is prepared at a first point in time, and the replicon is prepared at a later point in time. For example, following its preparation, the replicase construct may be stored for use at a later point in time. The present invention provides increased flexibility compared to cis-replicons: the system of the present invention may be designed for treatment, by cloning into the replicon a nucleic acid encoding a new reprogramming factor. A previously prepared replicase construct may be recovered from storage. In other words, the replicase construct can be designed and prepared independently of any particular replicon.

Second, the trans-replicon according to the present invention is typically a shorter nucleic acid molecule than a typical cis-replicon. This enables faster cloning of a replicon encoding a protein of interest, and provides high yields of the protein of interest.

Further advantages of the system of the present invention include the independence from nuclear transcription and the presence of key genetic information on two separate RNA molecules, which provides unprecedented design freedom. In view of its versatile elements, which are combinable with each other, the present invention allows to optimize replicase expression for a desired level of RNA amplification, for a desired target organism, for a desired level of production of a protein of interest, etc.

The system according to the invention allows to co-transfect varying amounts or ratios of replicon and replicase construct for any given cell type—resting or cycling, in vitro or in vivo.

The replicase construct according to the present invention is preferably a single stranded RNA molecule. The replicase construct according to the present invention is typically a (+)

stranded RNA molecule. In one embodiment, the replicase construct of the present invention is an isolated nucleic acid molecule.

Preferred Features of RNA Molecules According to the Invention

RNA molecules according to the invention may optionally be characterized by further features, e.g. by a 5'-cap, a 5'-UTR, a 3'-UTR, a poly(A) sequence, and/or adaptation of the codon usage. Details are described in the following.

Cap

In some embodiments, the replicon according to the present invention comprises a 5'-cap.

In some embodiments, the replicase construct according to the present invention comprises a 5'-cap.

The terms "5'-cap", "cap", "5'-cap structure", "cap structure" are used synonymously to refer to a dinucleotide that is found on the 5' end of some eukaryotic primary transcripts such as precursor messenger RNA. A 5'-cap is a structure wherein a (optionally modified) guanosine is bonded to the first nucleotide of an mRNA molecule via a 5' to 5' triphosphate linkage (or modified triphosphate linkage in the case of certain cap analogs). The terms can refer to a conventional cap or to a cap analog. For illustration, some particular cap dinucleotides (including cap analog dinucleotides) are shown in FIG. 6.

"RNA which comprises a 5'-cap" or "RNA which is provided with a 5'-cap" or "RNA which is modified with a 5'-cap" or "capped RNA" refers to RNA which comprises a 5'-cap. For example, providing an RNA with a 5'-cap may be achieved by in vitro transcription of a DNA template in presence of said 5'-cap, wherein said 5'-cap is co-transcriptionally incorporated into the generated RNA strand, or the RNA may be generated, for example, by in vitro transcription, and the 5'-cap may be attached to the RNA post-transcriptionally using capping enzymes, for example, capping enzymes of vaccinia virus. In capped RNA, the 3' position of the first base of a (capped) RNA molecule is linked to the 5' position of the subsequent base of the RNA molecule ("second base") via a phosphodiester bond.

Presence of a cap on an RNA molecule is strongly preferred if translation of a nucleic acid sequence encoding a protein at early stages after introduction of the respective RNA into host cells or into a host organism is desired. For example, presence of a cap allows that a gene of interest encoded by RNA replicon is translated efficiently at early stages after introduction of the respective RNA into host cells. "Early stages" typically means within the first 1 hour, or within the first two hours, or within the first three hours after introduction of the RNA.

Presence of a cap on an RNA molecule is also preferred if it is desired that translation occurs in the absence of functional replicase, or when only minor levels of replicase are present in a host cell. For example, even if a nucleic acid molecule encoding replicase is introduced into a host cell, at early stages after introduction the levels of replicase will typically be minor.

In the system according to the invention, it is preferred that the RNA construct for expressing functional alphavirus non-structural protein comprises a 5'-cap.

In particular when the RNA replicon according to the present invention is not used or provided together with a second nucleic acid molecule (e.g. mRNA) that encodes functional alphavirus non-structural protein, it is preferred that the RNA replicon comprises a 5'-cap. Independently, the RNA replicon may also comprise a 5'-cap even when it is used or provided together with a second nucleic acid molecule that encodes functional alphavirus non-structural protein.

The term "conventional 5'-cap" refers to a naturally occurring 5'-cap, preferably to the 7-methylguanosine cap. In the 7-methylguanosine cap, the guanosine of the cap is a modified guanosine wherein the modification consists of a methylation at the 7-position (top of FIG. 6).

In the context of the present invention, the term "5'-cap analog" refers to a molecular structure that resembles a conventional 5'-cap, but is modified to possess the ability to stabilize RNA if attached thereto, preferably in vivo and/or in a cell. A cap analog is not a conventional 5'-cap.

For the case of eukaryotic mRNA, the 5'-cap has been generally described to be involved in efficient translation of mRNA: in general, in eukaryotes, translation is initiated only at the 5' end of a messenger RNA (mRNA) molecule, unless an internal ribosomal entry site (IRES) is present. Eukaryotic cells are capable of providing an RNA with a 5'-cap during transcription in the nucleus: newly synthesized mRNAs are usually modified with a 5'-cap structure, e.g. when the transcript reaches a length of 20 to 30 nucleotides. First, the 5' terminal nucleotide pppN (ppp representing triphosphate; N representing any nucleoside) is converted in the cell to 5' GpppN by a capping enzyme having RNA 5'-triphosphatase and guanylyltransferase activities. The GpppN may subsequently be methylated in the cell by a second enzyme with (guanine-7)-methyltransferase activity to form the mono-methylated m$^7$GpppN cap. In one embodiment, the 5'-cap used in the present invention is a natural 5'-cap.

In the present invention, a natural 5'-cap dinucleotide is typically selected from the group consisting of a non-methylated cap dinucleotide (G(5')ppp(5')N; also termed GpppN) and a methylated cap dinucleotide ((m$^7$G(5')ppp(5')N; also termed m$^7$GpppN). m$^7$GpppN (wherein N is G) is represented by the following formula:

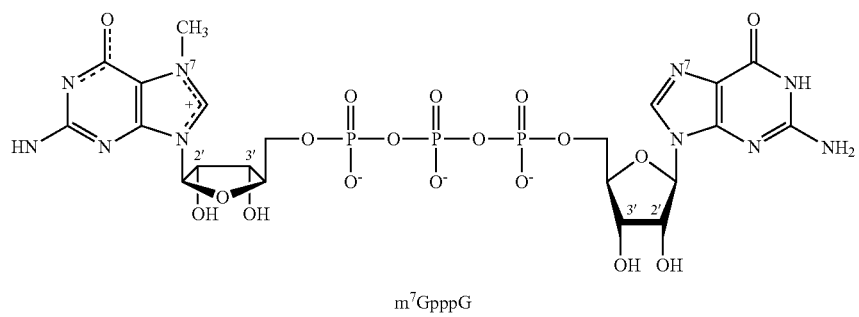

m$^7$GpppG

Capped RNA of the present invention can be prepared in vitro, and therefore, does not depend on a capping machinery in a host cell. The most frequently used method to make capped RNAs in vitro is to transcribe a DNA template with either a bacterial or bacteriophage RNA polymerase in the presence of all four ribonucleoside triphosphates and a cap dinucleotide such as m$^7$G(5')ppp(5')G (also called m$^7$GpppG). The RNA polymerase initiates transcription with a nucleophilic attack by the 3'-OH of the guanosine moiety of m$^7$GpppG on the α-phosphate of the next templated nucleoside triphosphate (pppN), resulting in the intermediate m$^7$GpppGpN (wherein N is the second base of the RNA molecule). The formation of the competing GTP-initiated product pppGpN is suppressed by setting the molar ratio of cap to GTP between 5 and 10 during in vitro transcription.

In preferred embodiments of the present invention, the 5'-cap (if present) is a 5'-cap analog. These embodiments are particularly suitable if the RNA is obtained by in vitro transcription, e.g. is an in vitro transcribed RNA (IVT-RNA). Cap analogs have been initially described to facilitate large scale synthesis of RNA transcripts by means of in vitro transcription.

For messenger RNA, some cap analogs (synthetic caps) have been generally described to date, and they can all be used in the context of the present invention. Ideally, a cap analog is selected that is associated with higher translation efficiency and/or increased resistance to in vivo degradation and/or increased resistance to in vitro degradation.

Preferably, a cap analog is used that can only be incorporated into an RNA chain in one orientation. Pasquinelli et al. (1995, RNA J., vol., 1, pp. 957-967) demonstrated that during in vitro transcription, bacteriophage RNA polymerases use the 7-methylguanosine unit for initiation of transcription, whereby around 40-50% of the transcripts with cap possess the cap dinucleotide in a reverse orientation (i.e., the initial reaction product is Gpppm$^7$GpN). Compared to the RNAs with a correct cap, RNAs with a reverse cap are not functional with respect to translation of a nucleic acid sequence into protein. Thus, it is desirable to incorporate the cap in the correct orientation, i.e., resulting in an RNA with a structure essentially corresponding to m$^7$GpppGpN etc. It has been shown that the reverse integration of the cap-dinucleotide is inhibited by the substitution of either the 2'- or the 3'—OH group of the methylated guanosine unit (Stepinski et al., 2001; RNA J., vol. 7, pp. 1486-1495; Peng et al., 2002; Org. Lett., vol. 24, pp. 161-164). RNAs which are synthesized in presence of such "anti reverse cap analogs" are translated more efficiently than RNAs which are in vitro transcribed in presence of the conventional 5'-cap m$^7$GpppG. To that end, one cap analog in which the 3' OH group of the methylated guanosine unit is replaced by OCH$_3$ is described e.g. by Holtkamp et al., 2006, Blood, vol. 108, pp. 4009-4017 (7-methyl(3'-O-methyl)GpppG; anti-reverse cap analog (ARCA)). ARCA is a suitable cap dinucleotide according to the present invention.

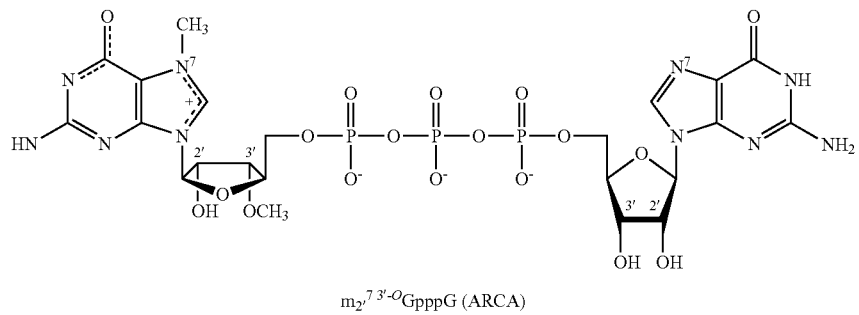

m$_2$$^{7\ 3'\text{-}O}$GpppG (ARCA)

In a preferred embodiment of the present invention, the RNA of the present invention is essentially not susceptible to decapping. This is important because, in general, the amount of protein produced from synthetic mRNAs introduced into cultured mammalian cells is limited by the natural degradation of mRNA. One in vivo pathway for mRNA degradation begins with the removal of the mRNA cap. This removal is catalyzed by a heterodimeric pyrophosphatase, which contains a regulatory subunit (Dcp1) and a catalytic subunit (Dcp2). The catalytic subunit cleaves between the α and β phosphate groups of the triphosphate bridge. In the present invention, a cap analog may be selected or present that is not susceptible, or less susceptible, to that type of cleavage. A suitable cap analog for this purpose may be selected from a cap dinucleotide according to formula (I):

formula (I)

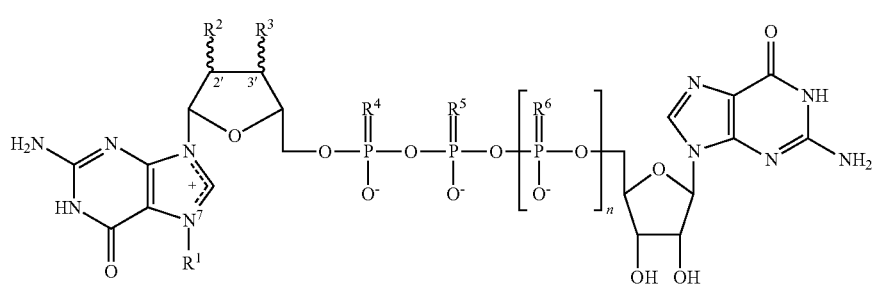

wherein R$^1$ is selected from the group consisting of optionally substituted alkyl, optionally substituted alkenyl, optionally substituted alkynyl, optionally substituted cycloalkyl, optionally substituted heterocyclyl, optionally substituted aryl, and optionally substituted heteroaryl, $R^2$ and $R^3$ are independently selected from the group consisting of H, halo, OH, and optionally substituted alkoxy, or $R^2$ and $R^3$ together form O—X—O, wherein X is selected from the group consisting of optionally substituted $CH_2$, $CH_2CH_2$, $CH_2CH_2CH_2$, $CH_2CH(CH_3)$, and $C(CH_3)_2$, or $R^2$ is combined with the hydrogen atom at position 4' of the ring to which $R^2$ is attached to form —O—$CH_2$— or —$CH_2$—O—, $R^5$ is selected from the group consisting of S, Se, and $BH_3$, binding proteins in both the translational and decapping machinery. At least some of these analogs are essentially resistant to pyrophosphatase Dcp1/Dcp2. Phosphorothioate-modified ARCAs were described to have a much higher affinity for eIF4E than the corresponding ARCAs lacking a phosphorothioate group.

A respective cap analog that is particularly preferred in the present invention, i.e., $m_2^{7,2'-O}Gpp_spG$, is termed beta-S-ARCA (WO 2008/157688 A2; Kuhn et al., Gene Ther., 2010, vol. 17, pp. 961-971). Thus, in one embodiment of the present invention, the RNA of the present invention is modified with beta-S-ARCA. beta-S-ARCA is represented by the following structure:

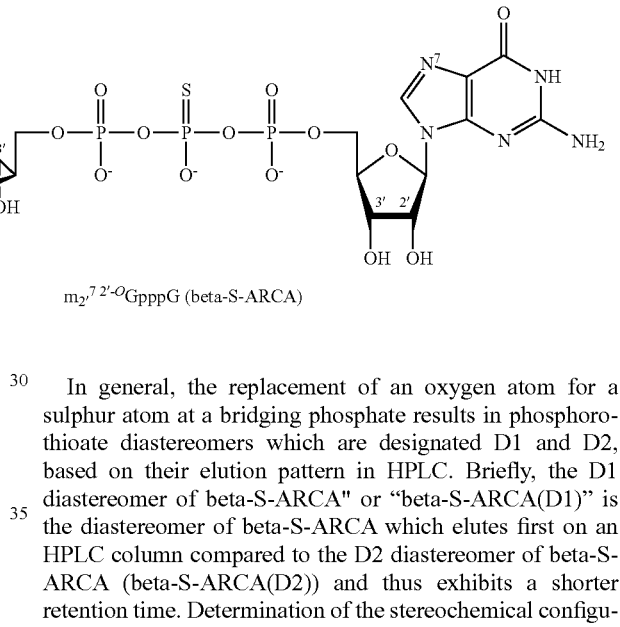

$m_2^{7\,2'-O}GpppG$ (beta-S-ARCA)

$R^4$ and $R^6$ are independently selected from the group consisting of O, S, Se, and $BH_3$.

n is 1, 2, or 3.

Preferred embodiments for $R^1$, $R^2$, R3, $R^4$, $R^5$, $R^6$ are disclosed in WO 2011/015347 A1 and may be selected accordingly in the present invention.

For example, in a preferred embodiment of the present invention, the RNA of the present invention comprises a phosphorothioate-cap-analog. Phosphorothioate-cap-analogs are specific cap analogs in which one of the three non-bridging O atoms in the triphosphate chain is replaced with an S atom, i.e. one of $R^4$, $R^5$ or $R^6$ in Formula (I) is S. Phosphorothioate-cap-analogs have been described by J. Kowalska et al., 2008, RNA, vol. 14, pp. 1119-1131, as a solution to the undesired decapping process, and thus to increase the stability of RNA in vivo. In particular, the substitution of an oxygen atom for a sulphur atom at the beta-phosphate group of the 5'-cap results in stabilization against Dcp2. In that embodiment, which is preferred in the present invention, $R^5$ in Formula (I) is S; and $R^4$ and $R^6$ are O.

In a further preferred embodiment of the present invention, the RNA of the present invention comprises a phosphorothioate-cap-analog wherein the phosphorothioate modification of the RNA 5'-cap is combined with an "anti-reverse cap analog" (ARCA) modification. Respective ARCA-phosphorothioate-cap-analogs are described in WO 2008/157688 A2, and they can all be used in the RNA of the present invention. In that embodiment, at least one of $R^2$ or $R^3$ in Formula (I) is not OH, preferably one among $R^2$ and $R^3$ is methoxy ($OCH_3$), and the other one among $R^2$ and $R^3$ is preferably OH. In a preferred embodiment, an oxygen atom is substituted for a sulphur atom at the beta-phosphate group (so that $R^5$ in Formula (I) is S; and $R^4$ and $R^6$ are O). It is believed that the phosphorothioate modification of the ARCA ensures that the α, β, and γ phosphorothioate groups are precisely positioned within the active sites of cap- In general, the replacement of an oxygen atom for a sulphur atom at a bridging phosphate results in phosphorothioate diastereomers which are designated D1 and D2, based on their elution pattern in HPLC. Briefly, the D1 diastereomer of beta-S-ARCA" or "beta-S-ARCA(D1)" is the diastereomer of beta-S-ARCA which elutes first on an HPLC column compared to the D2 diastereomer of beta-S-ARCA (beta-S-ARCA(D2)) and thus exhibits a shorter retention time. Determination of the stereochemical configuration by HPLC is described in WO 2011/015347 A1.

In a first particularly preferred embodiment of the present invention, RNA of the present invention is modified with the beta-S-ARCA(D2) diastereomer. The two diastereomers of beta-S-ARCA differ in sensitivity against nucleases. It has been shown that RNA carrying the D2 diastereomer of beta-S-ARCA is almost fully resistant against Dcp2 cleavage (only 6% cleavage compared to RNA which has been synthesized in presence of the unmodified ARCA 5'-cap), whereas RNA with the beta-S-ARCA(D1) 5'-cap exhibits an intermediary sensitivity to Dcp2 cleavage (71% cleavage). It has further been shown that the increased stability against Dcp2 cleavage correlates with increased protein expression in mammalian cells. In particular, it has been shown that RNAs carrying the beta-S-ARCA(D2) cap are more efficiently translated in mammalian cells than RNAs carrying the beta-S-ARCA(D1) cap. Therefore, in one embodiment of the present invention, RNA of the present invention is modified with a cap analog according to Formula (I), characterized by a stereochemical configuration at the P atom comprising the substituent $R^5$ in Formula (I) that corresponds to that at the $P_β$ atom of the D2 diastereomer of beta-S-ARCA. In that embodiment, $R^5$ in Formula (I) is S; and $R^4$ and $R^6$ are O. Additionally, at least one of $R^2$ or $R^3$ in Formula (I) is preferably not OH, preferably one among $R^2$ and $R^3$ is methoxy ($OCH_3$), and the other one among $R^2$ and $R^3$ is preferably OH.

In a second particularly preferred embodiment, RNA of the present invention is modified with the beta-S-ARCA (D1) diastereomer. It has been demonstrated that the beta-S-ARCA(D1) diastereomer, upon transfer of respectively capped RNA into immature antigen presenting cells, is particularly suitable for increasing the stability of the RNA, increasing translation efficiency of the RNA, prolonging translation of the RNA, increasing total protein expression of the RNA, and/or increasing the immune response against an antigen or antigen peptide encoded by said RNA (Kuhn et al., 2010, Gene Ther., vol. 17, pp. 961-971). Therefore, in an alternative embodiment of the present invention, RNA of the present invention is modified with a cap analog according to Formula (I), characterized by a stereochemical configuration at the P atom comprising the substituent $R^5$ in Formula (I) that corresponds to that at the $P_\beta$ atom of the D1 diastereomer of beta-S-ARCA. Respective cap analogs and embodiments thereof are described in WO 2011/015347 A1 and Kuhn et al., 2010, Gene Ther., vol. 17, pp. 961-971. Any cap analog described in WO 2011/015347 A1, wherein the stereochemical configuration at the P atom comprising the substituent $R^5$ corresponds to that at the $P_\beta$ atom of the D1 diastereomer of beta-S-ARCA, may be used in the present invention. Preferably, $R^5$ in Formula (I) is S; and $R^4$ and $R^6$ are O. Additionally, at least one of $R^2$ or $R^3$ in Formula (I) is preferably not OH, preferably one among $R^2$ and $R^3$ is methoxy ($OCH_3$), and the other one among $R^2$ and $R^3$ is preferably OH.

In one embodiment, RNA of the present invention is modified with a 5'-cap structure according to Formula (I) wherein any one phosphate group is replaced by a boranophosphate group or a phosphoroselenoate group. Such caps have increased stability both in vitro and in vivo. Optionally, the respective compound has a 2'-O- or 3'-O-alkyl group (wherein alkyl is preferably methyl); respective cap analogs are termed $BH_3$-ARCAs or Se-ARCAs. Compounds that are particularly suitable for capping of mRNA include the β-$BH_3$-ARCAs and β-Se-ARCAs, as described in WO 2009/149253 A2. For these compounds, a stereochemical configuration at the P atom comprising the substituent $R^5$ in Formula (I) that corresponds to that at the $P_\beta$ atom of the D1 diastereomer of beta-S-ARCA is preferred.

UTR

The term "untranslated region" or "UTR" relates to a region in a DNA molecule which is transcribed but is not translated into an amino acid sequence, or to the corresponding region in an RNA molecule, such as an mRNA molecule. An untranslated region (UTR) can be present 5' (upstream) of an open reading frame (5'-UTR) and/or 3' (downstream) of an open reading frame (3'-UTR).

A 3'-UTR, if present, is located at the 3' end of a gene, downstream of the termination codon of a protein-encoding region, but the term "3'-UTR" does preferably not include the poly(A) tail. Thus, the 3'-UTR is upstream of the poly(A) tail (if present), e.g. directly adjacent to the poly(A) tail.

A 5'-UTR, if present, is located at the 5' end of a gene, upstream of the start codon of a protein-encoding region. A 5'-UTR is downstream of the 5'-cap (if present), e.g. directly adjacent to the 5'-cap.

5'- and/or 3'-untranslated regions may, according to the invention, be functionally linked to an open reading frame, so as for these regions to be associated with the open reading frame in such a way that the stability and/or translation efficiency of the RNA comprising said open reading frame are increased.

In some embodiments, the replicase construct according to the present invention comprises a 5'-UTR and/or a 3'-UTR.

In a preferred embodiment, the replicase construct according to the present invention comprises (1) a 5'-UTR, (2) an open reading frame, and (3) a 3'-UTR.

UTRs are implicated in stability and translation efficiency of RNA. Both can be improved, besides structural modifications concerning the 5'-cap and/or the 3' poly(A)-tail as described herein, by selecting specific 5' and/or 3' untranslated regions (UTRs). Sequence elements within the UTRs are generally understood to influence translational efficiency (mainly 5'-UTR) and RNA stability (mainly 3'-UTR). It is preferable that a 5'-UTR is present that is active in order to increase the translation efficiency and/or stability of the replicase construct. Independently or additionally, it is preferable that a 3'-UTR is present that is active in order to increase the translation efficiency and/or stability of the replicase construct.

The terms "active in order to increase the translation efficiency" and/or "active in order to increase the stability", with reference to a first nucleic acid sequence (e.g. a UTR), means that the first nucleic acid sequence is capable of modifying, in a common transcript with a second nucleic acid sequence, the translation efficiency and/or stability of said second nucleic acid sequence in such a way that said translation efficiency and/or stability is increased in comparison with the translation efficiency and/or stability of said second nucleic acid sequence in the absence of said first nucleic acid sequence.

In one embodiment, the replicase construct according to the present invention comprises a 5'-UTR and/or a 3'-UTR which is heterologous or non-native to the alphavirus from which the functional alphavirus non-structural protein is derived. This allows the untranslated regions to be designed according to the desired translation efficiency and RNA stability. Thus, heterologous or non-native UTRs allow for a high degree of flexibility, and this flexibility is advantageous compared to native alphaviral UTRs. In particular, while it is known that alphaviral (native) RNA also comprises a 5'-UTR and/or a 3'-UTR, alphaviral UTRs fulfil a dual function, i.e. (i) to drive RNA replication as well as (ii) to drive translation. While alphaviral UTRs were reported to be inefficient for translation (Berben-Bloemheuvel et al., 1992, Eur. J. Biochem., vol. 208, pp. 581-587), they can typically not readily be replaced by more efficient UTRs because of their dual function. In the present invention, however, a 5'-UTR and/or a 3'-UTR comprised in a replicase construct for replication in trans can be selected independent of their potential influence on RNA replication.

Preferably, the replicase construct according to the present invention comprises a 5'-UTR and/or a 3'-UTR that is not of virus origin; particularly not of alphavirus origin. In one embodiment, the replicase construct comprises a 5'-UTR derived from a eukaryotic 5'-UTR and/or a 3'-UTR derived from a eukaryotic 3'-UTR.

A 5'-UTR according to the present invention can comprise any combination of more than one nucleic acid sequence, optionally separated by a linker. A 3'-UTR according to the present invention can comprise any combination of more than one nucleic acid sequence, optionally separated by a linker.

The term "linker" according to the invention relates to a nucleic acid sequence added between two nucleic acid sequences to connect said two nucleic acid sequences. There is no particular limitation regarding the linker sequence.

A 3'-UTR typically has a length of 200 to 2000 nucleotides, e.g. 500 to 1500 nucleotides. The 3'-untranslated regions of immunoglobulin mRNAs are relatively short (fewer than about 300 nucleotides), while the 3'-untranslated regions of other genes are relatively long. For example, the 3'-untranslated region of tPA is about 800 nucleotides in length, that of factor VIII is about 1800 nucleotides in length and that of erythropoietin is about 560 nucleotides in length. The 3'-untranslated regions of mammalian mRNA typically have a homology region known as the AAUAAA hexanucleotide sequence. This sequence is presumably the poly(A) attachment signal and is frequently located from 10 to 30 bases upstream of the poly(A) attachment site. 3'-untranslated regions may contain one or more inverted repeats which can fold to give stem-loop structures which act as barriers for exoribonucleases or interact with proteins known to increase RNA stability (e.g. RNA-binding proteins).

The human beta-globin 3'-UTR, particularly two consecutive identical copies of the human beta-globin 3'-UTR, contributes to high transcript stability and translational efficiency (Holtkamp et al., 2006, Blood, vol. 108, pp. 4009-4017). Thus, in one embodiment, the replicase construct according to the present invention comprises two consecutive identical copies of the human beta-globin 3'-UTR. Thus, it comprises in the 5'→3' direction: (a) optionally a 5'-UTR; (b) an open reading frame; (c) a 3'-UTR; said 3'-UTR comprising two consecutive identical copies of the human beta-globin 3'-UTR, a fragment thereof, or a variant of the human beta-globin 3'-UTR or fragment thereof.

In one embodiment, the replicase construct according to the present invention comprises a 3'-UTR which is active in order to increase translation efficiency and/or stability, but which is not the human beta-globin 3'-UTR, a fragment thereof, or a variant of the human beta-globin 3'-UTR or fragment thereof.

In one embodiment, the replicase construct according to the present invention comprises a 5'-UTR which is active in order to increase translation efficiency and/or stability.

A UTR-containing replicase construct according to the invention can be prepared e.g. by in vitro transcription. This may be achieved by genetically modifying a template nucleic acid molecule (e.g. DNA) in such a way that it allows transcription of RNA with 5'-UTRs and/or 3'-UTRs.

As illustrated in FIG. 5, also the replicon can be characterized by a 5'-UTR and/or a 3'-UTR. The UTRs of the replicon are typically alphaviral UTRs or variants thereof.

Poly(A) Sequence

In some embodiments, the replicon according to the present invention comprises a 3'-poly(A) sequence. If the replicon comprises conserved sequence element 4 (CSE 4), the 3'-poly(A) sequence of the replicon is preferably present downstream of CSE 4, most preferably directly adjacent to CSE 4.

In some embodiments, the replicase construct according to the present invention comprises a 3'-poly(A) sequence.

According to the invention, in one embodiment, a poly(A) sequence comprises or essentially consists of or consists of at least 20, preferably at least 26, preferably at least 40, preferably at least 80, preferably at least 100 and preferably up to 500, preferably up to 400, preferably up to 300, preferably up to 200, and in particular up to 150, A nucleotides, and in particular about 120 A nucleotides. In this context "essentially consists of" means that most nucleotides in the poly(A) sequence, typically at least 50%, and preferably at least 75% by number of nucleotides in the "poly(A) sequence", are A nucleotides (adenylate), but permits that remaining nucleotides are nucleotides other than A nucleotides, such as U nucleotides (uridylate), G nucleotides (guanylate), C nucleotides (cytidylate). In this context "consists of" means that all nucleotides in the poly(A) sequence, i.e. 100% by number of nucleotides in the poly(A) sequence, are A nucleotides. The term "A nucleotide" or "A" refers to adenylate.

Indeed, it has been demonstrated that a 3' poly(A) sequence of about 120 A nucleotides has a beneficial influence on the levels of RNA in transfected eukaryotic cells, as well as on the levels of protein that is translated from an open reading frame that is present upstream (5') of the 3' poly(A) sequence (Holtkamp et al., 2006, Blood, vol. 108, pp. 4009-4017).

In alphaviruses, a 3' poly(A) sequence of at least 11 consecutive adenylate residues, or at least 25 consecutive adenylate residues, is thought to be important for efficient synthesis of the minus strand. In particular, in alphaviruses, a 3' poly(A) sequence of at least 25 consecutive adenylate residues is understood to function together with conserved sequence element 4 (CSE 4) to promote synthesis of the (−) strand (Hardy & Rice, J. Virol., 2005, vol. 79, pp. 4630-4639).

The present invention provides for a 3' poly(A) sequence to be attached during RNA transcription, i.e. during preparation of in vitro transcribed RNA, based on a DNA template comprising repeated dT nucleotides (deoxythymidylate) in the strand complementary to the coding strand. The DNA sequence encoding a poly(A) sequence (coding strand) is referred to as poly(A) cassette.

In a preferred embodiment of the present invention, the 3' poly(A) cassette present in the coding strand of DNA essentially consists of dA nucleotides, but is interrupted by a random sequence having an equal distribution of the four nucleotides (dA, dC, dG, dT). Such random sequence may be 5 to 50, preferably 10 to 30, more preferably 10 to 20 nucleotides in length. Such a cassette is disclosed in WO 2016/005004 A1. Any poly(A) cassette disclosed in WO 2016/005004 A1 may be used in the present invention. A poly(A) cassette that essentially consists of dA nucleotides, but is interrupted by a random sequence having an equal distribution of the four nucleotides (dA, dC, dG, dT) and having a length of e.g. 5 to 50 nucleotides shows, on DNA level, constant propagation of plasmid DNA in E. coli and is still associated, on RNA level, with the beneficial properties with respect to supporting RNA stability and translational efficiency.

Consequently, in a preferred embodiment of the present invention, the 3' poly(A) sequence contained in an RNA molecule described herein essentially consists of A nucleotides, but is interrupted by a random sequence having an equal distribution of the four nucleotides (A, C, G, U). Such random sequence may be 5 to 50, preferably 10 to 30, more preferably 10 to 20 nucleotides in length.

Codon Usage

In general, the degeneracy of the genetic code will allow the substitution of certain codons (base triplets coding for an amino acid) that are present in an RNA sequence by other codons (base triplets), while maintaining the same coding capacity (so that the replacing codon encodes the same amino acid as the replaced codon). In some embodiments of the present invention, at least one codon of an open reading frame comprised by a RNA molecule differs from the respective codon in the respective open reading frame in the species from which the open reading frame originates. In that embodiment, the coding sequence of the open reading frame is said to be "adapted" or "modified". The coding sequence of an open reading frame comprised by the replicon may be adapted. Alternatively or additionally, the coding sequence for functional alphavirus non-structural protein comprised by the replicase construct may be adapted.

For example, when the coding sequence of an open reading frame is adapted, frequently used codons may be selected: WO 2009/024567 A1 describes the adaptation of a coding sequence of a nucleic acid molecule, involving the substitution of rare codons by more frequently used codons. Since the frequency of codon usage depends on the host cell or host organism, that type of adaptation is suitable to fit a nucleic acid sequence to expression in a particular host cell or host organism. Generally, speaking, more frequently used codons are typically translated more efficiently in a host cell or host organism, although adaptation of all codons of an open reading frame is not always required.

For example, when the coding sequence of an open reading frame is adapted, the content of G (guanylate) residues and C (cytidylate) residues may be altered by selecting codons with the highest GC-rich content for each amino acid. RNA molecules with GC-rich open reading frames were reported to have the potential to reduce immune activation and to improve translation and half-life of RNA (Thess et al., 2015, Mol. Ther. 23, 1457-1465).

When the replicon according to the present invention encodes alphavirus non-structural protein, the coding sequence for alphavirus non-structural protein can be adapted as desired. This freedom is possible because the open reading frame encoding alphavirus non-structural protein does not overlap with the 5' replication recognition sequence of the replicon.

Safety Features of Embodiments of the Present Invention

The following features are preferred in the present invention, alone or in any suitable combination:

Preferably, the replicon or the system of the present invention is not particle-forming. This means that, following inoculation of a host cell by the replicon or the system of the present invention, the host cell does not produce virus particles, such as next generation virus particles. In one embodiment, all RNA molecules according to the invention are completely free of genetic information encoding any alphavirus structural protein, such as core nucleocapsid protein C, envelope protein P62, and/or envelope protein E1. This aspect of the present invention provides an added value in terms of safety over prior art systems wherein structural proteins are encoded on trans-replicating helper RNA (e.g. Bredenbeek et al., J. Virol, 1993, vol. 67, pp. 6439-6446).

Preferably, the system of the present invention does not comprise any alphavirus structural protein, such as core nucleocapsid protein C, envelope protein P62, and/or envelope protein E1.

Preferably, the replicon and the replicase construct of the system of the present invention are non-identical to each other. In one embodiment, the replicon does not encode functional alphavirus non-structural protein. In one embodiment, the replicase construct lacks at least one sequence element (preferably at least one CSE) that is required for (−) strand synthesis based on a (+) strand template, and/or for (+) strand synthesis based on a (−) strand template. In one embodiment, the replicase construct does not comprise CSE 1 and/or CSE 4.

Preferably, neither the replicon according to the present invention nor the replicase construct according to the present invention comprises an alphavirus packaging signal. For example, the alphavirus packaging signal comprised in the coding region of nsP2 of SFV (White et al. 1998, J. Virol., vol. 72, pp. 4320-4326) may be removed, e.g. by deletion or mutation. A suitable way of removing the alphavirus packaging signal includes adaptation of the codon usage of the coding region of nsP2. The degeneration of the genetic code may allow to delete the function of the packaging signal without affecting the amino acid sequence of the encoded nsP2.

In one embodiment, the system of the present invention is an isolated system. In that embodiment, the system is not present inside a cell, such as inside a mammalian cell, or is not present inside a virus capsid, such as inside a coat comprising alphavirus structural proteins. In one embodiment, the system of the present invention is present in vitro.

DNA

In a further aspect, the present invention provides DNA comprising nucleic acid sequence encoding the RNA replicon, the set of RNA replicons or the system according to the present invention. According to the invention, instead of using RNA, e.g., for transfection of cells, DNA encoding the RNA may be used, e.g., for transfection of cells such that the RNA is produced in the cells.

Preferably, the DNA is double-stranded.

In a preferred embodiment, the DNA is a plasmid. The term "plasmid", as used herein, generally relates to a construct of extrachromosomal genetic material, usually a circular DNA duplex, which can replicate independently of chromosomal DNA.

The DNA of the present invention may comprise a promoter that can be recognized by a DNA-dependent RNA-polymerase. This allows for transcription of the encoded RNA in vivo or in vitro, e.g. of the RNA of the present invention. IVT vectors may be used in a standardized manner as template for in vitro transcription. Examples of promoters preferred according to the invention are promoters for SP6, T3 or T7 polymerase.

In one embodiment, the DNA of the present invention is an isolated nucleic acid molecule.

Methods of Preparing RNA

Any RNA molecule according to the present invention, be it part of the system of the present invention or not, may be obtainable by in vitro transcription. In vitro-transcribed RNA (IVT-RNA) is of particular interest in the present invention. IVT-RNA is obtainable by transcription from a nucleic acid molecule (particularly a DNA molecule). The DNA molecule(s) of the present invention are suitable for such purposes, particularly if comprising a promoter that can be recognized by a DNA-dependent RNA-polymerase.

RNA according to the present invention can be synthesized in vitro. This allows to add cap-analogs to the in vitro transcription reaction. Typically, the poly(A) tail is encoded by a poly-(dT) sequence on the DNA template. Alternatively, capping and poly(A) tail addition can be achieved enzymatically after transcription.

The in vitro transcription methodology is known to the skilled person. For example, as mentioned in WO 2011/015347 A1, a variety of in vitro transcription kits is commercially available.

Methods for Producing Cells and Cells Produced Thereby

In further aspects, the present invention provides a method for producing cells having stem cell characteristics comprising transducing somatic cells with one or more RNA replicons of the invention and optionally a RNA construct for expressing functional alphavirus non-structural protein.

In one embodiment, the present invention provides a method for providing cells having stem cell characteristics comprising the steps of:
(i) providing a cell population comprising somatic cells,
(ii) providing one or more RNA replicons, wherein each of the one or more RNA replicons comprises an open reading frame encoding functional alphavirus non-structural protein, can be replicated by the functional alphavirus non-structural protein and comprises at least one open reading frame encoding a reprogramming factor,
(iii) introducing the one or more RNA replicons into the somatic cells, such that the cells express a set of reprogramming factors useful in reprogramming somatic cells to cells having stem cell characteristics, and
(iv) allowing the development of cells having stem cell characteristics.

In a further embodiment, the present invention provides a method for providing cells having stem cell characteristics comprising the steps of:
(i) providing a cell population comprising somatic cells,
(ii) providing a RNA construct for expressing functional alphavirus non-structural protein,
(iii) providing one or more RNA replicons, wherein each of the one or more RNA replicons can be replicated by the functional alphavirus non-structural protein in trans and comprises at least one open reading frame encoding a reprogramming factor,
(iv) introducing the RNA construct and the one or more RNA replicons into the somatic cells, such that the cells express a set of reprogramming factors useful in reprogramming somatic cells to cells having stem cell characteristics, and
(v) allowing the development of cells having stem cell characteristics.

According to the invention, the term "introducing RNA into the somatic cells" includes and preferably relates to embodiments wherein the RNA is only introduced into a portion of the cells and a portion of the cells remains un-transfected. If more than one RNA molecule is to be introduced into cells, e.g., more than one RNA replicon or a RNA construct for expressing functional alphavirus non-structural protein and one or more RNA replicons, the term includes and preferably relates to embodiments wherein all RNA molecules are only introduced into a portion of the cells and a portion of the cells remains un-transfected or remain transfected by not all of said RNA molecules. In any case, if according to the invention more than one RNA molecule is to be introduced into cells, e.g., more than one RNA replicon expressing a functional set of reprogramming factors or a RNA construct for expressing functional alphavirus non-structural protein and one or more RNA replicons, the aim is to introduce all RNA molecules into a cell, e.g., to express a functional set of reprogramming factors within a single cell.

In one embodiment, the transfected cells express the functional alphavirus non-structural protein encoded by one or more transfected replicons and/or by a transfected replicase construct and/or the reprogramming factor(s) encoded by one or more transfected replicons. The different reprogramming factors may be encoded by different open reading frames residing on the same RNA replicon or on different RNA replicons. In the latter embodiment, the different replicons are preferably co-transfected into a cell.

In various embodiments of the method, the RNA construct for expressing functional alphavirus non-structural protein and/or the RNA replicon are as defined above for the system of the invention, as long as the RNA replicon can be replicated by the functional alphavirus non-structural protein in trans and comprises an open reading frame encoding a reprogramming factor. The RNA construct for expressing functional alphavirus non-structural protein and the one or more RNA replicons may either be inoculated at the same point in time, or may alternatively be inoculated at different points in time. In the second case, the RNA construct for expressing functional alphavirus non-structural protein is typically inoculated at a first point in time, and the one or more replicons are typically inoculated at a second, later, point in time. In that case, it is envisaged that the one or more replicons will be immediately replicated since replicase will already have been synthesized in the cell. The second point in time is typically shortly after the first point in time, e.g. 1 minute to 24 hours after the first point in time.

The cell into which one or more nucleic molecules can be inoculated or transfected can be referred to as "host cell". According to the invention, the term "host cell" refers to any cell which can be transformed or transfected with an exogenous nucleic acid molecule. The term "cell" preferably is an intact cell, i.e. a cell with an intact membrane that has not released its normal intracellular components such as enzymes, organelles, or genetic material. An intact cell preferably is a viable cell, i.e. a living cell capable of carrying out its normal metabolic functions. The term "host cell" comprises, according to the invention, prokaryotic (e.g. *E. coli*) or eukaryotic cells (e.g. human and animal cells, plant cells, yeast cells and insect cells). Particular preference is given to mammalian cells such as cells from humans, mice, hamsters, pigs, domesticated animals including horses, cows, sheep and goats, as well as primates. The cells may be derived from a multiplicity of tissue types and comprise primary cells and cell lines. Specific examples include keratinocytes, peripheral blood leukocytes, bone marrow stem cells and embryonic stem cells. In other embodiments, the host cell is an antigen-presenting cell, in particular a dendritic cell, a monocyte or a macrophage. A nucleic acid may be present in the host cell in a single or in several copies and, in one embodiment is expressed in the host cell.

The cell may be a prokaryotic cell or a eukaryotic cell. Prokaryotic cells are suitable herein e.g. for propagation of DNA according to the invention, and eukaryotic cells are suitable herein e.g. for expression of the open reading frame of the replicon.

For purposes of the present invention, terms such as "transduction" or "transfection" refer to the introduction or incorporation of a nucleic acid into a cell or the uptake of a nucleic acid by a cell in vitro or in vivo. According to the present invention, a cell for transfection of a nucleic acid described herein can be present in vitro or in vivo, e.g. the cell can form part of an organ, a tissue and/or an organism of a patient. According to the invention, transfection can be transient or stable. For some applications of transfection, it is sufficient if the transfected genetic material is only transiently expressed. Since the nucleic acid introduced in the transfection process is usually not integrated into the nuclear genome, the foreign nucleic acid will be diluted through mitosis or degraded. Cells allowing episomal amplification of nucleic acids greatly reduce the rate of dilution. If it is desired that the transfected nucleic acid actually remains in the genome of the cell and its daughter cells, a stable transfection must occur. RNA can be transfected into cells to transiently express its coded protein.

According to the present invention, any technique useful for introducing, i.e., incorporating, transferring or transfecting, nucleic acids into cells may be used. Preferably, nucleic acid such as RNA is transfected into cells by standard techniques. Such techniques include electroporation, lipofection and microinjection. In one particularly preferred embodiment of the present invention, RNA is introduced into cells by electroporation. Electroporation or electropermeabilization relates to a significant increase in the electrical conductivity and permeability of the cell plasma membrane caused by an externally applied electrical field. It is usually used in molecular biology as a way of introducing some substance into a cell. According to the invention it is preferred that introduction of nucleic acid encoding a protein or peptide into cells results in expression of said protein or peptide.

For transfection of cells in vivo a pharmaceutical composition comprising nucleic acid may be used. A delivery vehicle that targets the nucleic acid to a specific cell may be administered to a patient, resulting in transfection that occurs in vivo.

In one embodiment, a method for producing cells is an in vitro method. In one embodiment, a method for producing cells comprises or does not comprise the removal of cells from a human or animal subject by surgery or therapy.

In this embodiment, the cells produced according to the invention may be administered to a subject. The cell may be autologous, syngenic, allogenic or heterologous with respect to the subject. Cells may be (re)introduced into a subject using any means known in the art.

In other embodiments, the somatic cells may be present in a subject, such as a patient. In these embodiments, the method for producing cells having stem cell characteristics is an in vivo method which comprises administration of RNA and/or DNA molecules to the subject.

In this respect, the invention also provides a method for producing cells having stem cell characteristics in a subject comprising the steps of:
 (i) providing one or more RNA replicons, wherein each of the one or more RNA replicons comprises an open reading frame encoding functional alphavirus non-structural protein, can be replicated by the functional alphavirus non-structural protein and comprises at least one open reading frame encoding a reprogramming factor,
 (ii) administering the one or more RNA replicons to the subject, and
 (iii) allowing the development of cells having stem cell characteristics.

In various embodiments of the method, the RNA replicon is as defined above for the RNA replicon of the invention, as long as the RNA replicon comprises an open reading frame encoding functional alphavirus non-structural protein and an open reading frame encoding a reprogramming factor, and can be replicated by the functional alphavirus non-structural protein.

The invention further provides a method for producing cells having stem cell characteristics in a subject comprising the steps of:
 (i) providing a RNA construct for expressing functional alphavirus non-structural protein,
 (ii) providing one or more RNA replicons, wherein each of the one or more RNA replicons can be replicated by the functional alphavirus non-structural protein in trans and comprises at least one open reading frame encoding a reprogramming factor,
 (iii) administering the RNA construct and the one or more RNA replicons to the subject, and
 (v) allowing the development of cells having stem cell characteristics.

In various embodiments of the method, the RNA construct for expressing functional alphavirus non-structural protein and/or the RNA replicon are as defined above for the system of the invention, as long as the RNA replicon can be replicated by the functional alphavirus non-structural protein in trans and comprises an open reading frame encoding a reprogramming factor. The RNA construct for expressing functional alphavirus non-structural protein and the one or more RNA replicons may either be administered at the same point in time, or may alternatively be administered at different points in time. In the second case, the RNA construct for expressing functional alphavirus non-structural protein is typically administered at a first point in time, and the one or more RNA replicons are typically administered at a second, later, point in time. In that case, it is envisaged that the one or more replicons will be immediately replicated since replicase will already have been synthesized in the cell.

The second point in time is typically shortly after the first point in time, e.g. 1 minute to 24 hours after the first point in time. Preferably the administration of the one or more RNA replicons is performed at the same site and via the same route of administration as the administration of the RNA construct for expressing functional alphavirus non-structural protein, in order to increase the prospects that the one or more RNA replicons and the RNA construct for expressing functional aiphavirus non-structural protein reach the same target tissue or cell. "Site" refers to the position of a subject's body. Suitable sites are for example, the left arm, right arm, etc.

In one embodiment, an additional RNA molecule, preferably an mRNA molecule, may be administered to the subject. Optionally, the additional RNA molecule encodes a protein suitable for inhibiting IFN, such as E3. Optionally, the additional RNA molecule may be administered prior to administration of the one or more replicons or of the replicase construct or of the system according to the invention.

Any of the RNA replicon according to the invention, the set according to the invention, the system according to the invention, the kit according to the invention, or the pharmaceutical composition according to the invention can be used in the method for producing cells in a subject according to the invention. For example, in the method of the invention, RNA can be used in the format of a pharmaceutical composition, e.g. as described herein, or as naked RNA.

In one embodiment of the invention, a functional set of reprogramming factors may comprise more than reprogramming factor which have to be all present within a cell so as to achieve reprogramming. Accordingly, the present invention involves embodiment wherein a set of RNA replicons encodes the different reprogramming factors. For example, different RNA replicons may comprise different open reading frames encoding different reprogramming factors. These different RNA replicons, i.e., a set of RNA replicons, may be co-inoculated (optionally together with a RNA construct for expressing functional aiphavirus non-structural protein) into a cell to provide a functional set of reprogramming factors.

Kit

The present invention also provides a kit comprising an RNA replicon according to the invention, a set according to the invention, or a system according to the invention.

In one embodiment, the constituents of the kit are present as separate entities. For example, one nucleic acid molecule of the kit may be present in one entity, and the another nucleic acid of the kit may be present in a separate entity. For example, an open or closed container is a suitable entity. A closed container is preferred. The container used should preferably be RNAse-free or essentially RNAse-free.

In one embodiment, the kit of the present invention comprises RNA for inoculation with a cell and/or for administration to a human or animal subject.

The kit according to the present invention optionally comprises a label or other form of information element, e.g. an electronic data carrier. The label or information element preferably comprises instructions, e.g. printed written instructions or instructions in electronic form that are optionally printable. The instructions may refer to at least one suitable possible use of the kit.

Uses of Reprogrammed Cells

Using the present invention, RNA replicons encoding appropriate factors are incorporated into one or more somatic cells, e.g. by electroporation or lipofection. After incorporation, cells are preferably cultured using conditions that support maintenance of de-differentiated cells (i.e. stem cell culture conditions). The de-differentiated cells can then be administered to a subject, e.g., in cell therapy, or optionally expanded and induced to re-differentiate into somatic cells that can then be administered to a subject, e.g., in cell therapy. Thus, de-differentiated cells obtained according to the present invention can be induced to differentiate into one or more desired somatic cell types in vitro or in vivo.

The term "cell therapy" (also called cellular therapy or cytotherapy) is a therapy in which cellular material, generally intact, living cells, is provided in a patient and preferably is administered to a patient. The term includes allogeneic cell therapy wherein the donor is a different person to the recipient of the cells and autologous cell therapy. Cell therapy is targeted at many clinical indications in multiple organs and by several modes of cell delivery. Accordingly, the specific mechanisms of action involved in the therapies are wide ranging. However, there are two main principles by which cells facilitate therapeutic action: (1) cells replacing damaged tissue, and thus facilitating improved function of the organ or tissue. An example of this is the use of cells to replace cardiomyocytes after myocardial infarction. (2) cells that have the capacity to release soluble factors such as cytokines, chemokines, and growth factors which act in a paracrine or endocrine manner. These factors facilitate self-healing of the organ or region. Examples of this include cells that secrete factors which facilitate angiogenesis, anti-inflammation, and anti-apoptosis.

Preferably, the de-differentiated cells obtained according to the present invention may give rise to cells from any of three embryonic germ layers, i.e., endoderm, mesoderm, and ectoderm. For example, the de-differentiated cells may differentiate into skeletal muscle, skeleton, dermis of skin, connective tissue, urogenital system, heart, blood (lymph cells), and spleen (mesoderm); stomach, colon, liver, pancreas, urinary bladder; lining of urethra, epithelial parts of trachea, lungs, pharynx, thyroid, parathyroid, intestine (endoderm); or central nervous system, retina and lens, cranial and sensory, ganglia and nerves, pigment cells, head connective tissue, epidermis, hair, mammary glands (ectoderm). The de-differentiated cells obtained according to the present invention can be re-differentiated in vitro or in vivo using techniques known in the art.

In one embodiment of the present invention, the reprogrammed cells resulting from the methods of this invention are used to produce differentiated progeny. Thus, in one aspect, the present invention provides a method for producing differentiated cells, comprising: (i) obtaining reprogrammed cells using the methods of this invention; and (ii) inducing differentiation of the reprogrammed cells to produce differentiated cells. Step (ii) can be performed in vivo or in vitro. Furthermore, differentiation can be induced through the presence of appropriate differentiation factors which can either be added or are present in situ, e.g. in a body, organ or tissue into which the reprogrammed cells have been introduced. The differentiated cells can be used to derive cells, tissues and/or organs which are advantageously used in the area of cell, tissue, and/or organ transplantation. If desired, genetic modifications can be introduced, for example, into somatic cells prior to reprogramming. The differentiated cells of the present invention preferably do not possess the pluripotency of an embryonic stem cell, or an embryonic germ cell, and are, in essence, tissue-specific partially or fully differentiated cells.

One advantage of the methods of the present invention is that the reprogrammed cells obtained by the present invention can be differentiated without prior selection or purification or establishment of a cell line. Accordingly in certain embodiments, a heterogeneous population of cells comprising reprogrammed cells are differentiated into a desired cell type. In one embodiment, a mixture of cells obtained from the methods of the present invention is exposed to one or more differentiation factors and cultured in vitro.

Methods of differentiating reprogrammed cells obtained by the methods disclosed herein may comprise a step of permeabilization of the reprogrammed cell. For example, cells generated by the reprogramming techniques described herein, or alternatively a heterogeneous mixture of cells comprising reprogrammed cells, may be permeabilized before exposure to one or more differentiation factors or cell extract or other preparation comprising differentiation factors.

For example, differentiated cells may be obtained by culturing undifferentiated reprogrammed cells in the presence of at least one differentiation factor and selecting differentiated cells from the culture. Selection of differentiated cells may be based on phenotype, such as the expression of certain cell markers present on differentiated cells, or by functional assays (e.g., the ability to perform one or more functions of a particular differentiated cell type).

In another embodiment, the cells reprogrammed according to the present invention are genetically modified through the addition, deletion, or modification of their DNA sequence(s).

The reprogrammed or de-differentiated cells prepared according to the present invention or cells derived from the reprogrammed or de-differentiated cells are useful in research and in therapy. Reprogrammed pluripotent cells may be differentiated into any of the cells in the body including, without limitation, skin, cartilage, bone skeletal muscle, cardiac muscle, renal, hepatic, blood and blood forming, vascular precursor and vascular endothelial, pancreatic beta, neurons, glia, retinal, neuronal, intestinal, lung, and liver cells.

The reprogrammed cells are useful for regenerative/reparative therapy and may be transplanted into a patient in need thereof. In one embodiment, the cells are autologous with the patient.

The reprogrammed cells provided in accordance with the present invention may be used, for example, in therapeutic strategies in the treatment of cardiac, neurological, endocrinological, vascular, retinal, dermatological, muscular-skeletal disorders, and other diseases.

For example, and not intended as a limitation, the reprogrammed cells of the present invention can be used to replenish cells in animals whose natural cells have been depleted due to age or ablation therapy such as cancer radiotherapy and chemotherapy. In another non-limiting example, the reprogrammed cells of the present invention are useful in organ regeneration and tissue repair. In one embodiment of the present invention, reprogrammed cells can be used to reinvigorate damaged muscle tissue including dystrophic muscles and muscles damaged by ischemic events such as myocardial infarcts. In another embodiment of the present invention, the reprogrammed cells disclosed herein can be used to ameliorate scarring in animals, including humans, following a traumatic injury or surgery. In this embodiment, the reprogrammed cells of the present invention are administered systemically, such as intravenously, and migrate to the site of the freshly traumatized tissue recruited by circulating cytokines secreted by the damaged cells. In another embodiment of the present invention, the reprogrammed cells can be administered locally to a treatment site in need or repair or regeneration.

Pharmaceutical Composition

The agents and compositions such as nucleic acids and cells described herein may be administered in the form of any suitable pharmaceutical composition.

The pharmaceutical compositions of the invention are preferably sterile and contain an effective amount of the agents described herein and optionally of further agents as discussed herein to generate the desired reaction or the desired effect.

Pharmaceutical compositions are usually provided in a uniform dosage form and may be prepared in a manner known per se. A pharmaceutical composition may e.g. be in the form of a solution or suspension.

A pharmaceutical composition may comprise salts, buffer substances, preservatives, carriers, diluents and/or excipients all of which are preferably pharmaceutically acceptable. The term "pharmaceutically acceptable" refers to the non-toxicity of a material which does not interact with the action of the active component of the pharmaceutical composition.

Salts which are not pharmaceutically acceptable may be used for preparing pharmaceutically acceptable salts and are included in the invention. Pharmaceutically acceptable salts of this kind comprise in a non limiting way those prepared from the following acids: hydrochloric, hydrobromic, sulfuric, nitric, phosphoric, maleic, acetic, salicylic, citric, formic, malonic, succinic acids, and the like. Pharmaceutically acceptable salts may also be prepared as alkali metal salts or alkaline earth metal salts, such as sodium salts, potassium salts or calcium salts.

Suitable buffer substances for use in a pharmaceutical composition include acetic acid in a salt, citric acid in a salt, boric acid in a salt and phosphoric acid in a salt.

Suitable preservatives for use in a pharmaceutical composition include benzalkonium chloride, chlorobutanol, paraben and thimerosal.

An injectable formulation may comprise a pharmaceutically acceptable excipient such as Ringer Lactate.

The term "carrier" refers to an organic or inorganic component, of a natural or synthetic nature, in which the active component is combined in order to facilitate, enhance or enable application. According to the invention, the term "carrier" also includes one or more compatible solid or liquid fillers, diluents or encapsulating substances, which are suitable for administration to a patient.

Possible carrier substances for parenteral administration are e.g. sterile water, Ringer, Ringer lactate, sterile sodium chloride solution, polyalkylene glycols, hydrogenated naphthalenes and, in particular, biocompatible lactide polymers, lactide/glycolide copolymers or polyoxyethylene/polyoxypropylene copolymers.

The term "excipient" when used herein is intended to indicate all substances which may be present in a pharmaceutical composition and which are not active ingredients such as, e.g., carriers, binders, lubricants, thickeners, surface active agents, preservatives, emulsifiers, buffers, flavoring agents, or colorants.

In one embodiment, if the pharmaceutical composition comprises nucleic acids, it comprises at least one cationic entity. In general, cationic lipids, cationic polymers and other substances with positive charges may form complexes with negatively charged nucleic acids. It is possible to stabilize the RNA according to the invention by complexation with cationic compounds, preferably polycationic compounds such as for example a cationic or polycationic peptide or protein. In one embodiment, the pharmaceutical composition according to the present invention comprises at least one cationic molecule selected from the group consisting protamine, polyethylene imine, a poly-L-lysine, a poly-L-arginine, a histone or a cationic lipid.

According to the present invention, a cationic lipid is a cationic amphiphilic molecule, e.g., a molecule which comprises at least one hydrophilic and lipophilic moiety. The cationic lipid can be monocationic or polycationic. Cationic lipids typically have a lipophilic moiety, such as a sterol, an acyl or diacyl chain, and have an overall net positive charge. The head group of the lipid typically carries the positive charge. The cationic lipid preferably has a positive charge of 1 to 10 valences, more preferably a positive charge of 1 to 3 valences, and more preferably a positive charge of 1 valence. Examples of cationic lipids include, but are not limited to 1,2-di-O-octadecenyl-3-trimethylamonium propane (DOTMA); dimethyldioctadecylammonium (DDAB); 1,2-dioleoyl-3-trimethylammonium-propane (DOTAP); 1,2-dioleoyl-3-dimethylammonium-propane (DODAP); 1,2-diacyloxy-3-dimethylammonium propanes; 1,2-dialkyloxy-3-dimethylammonium propanes; dioctadecyldimethyl ammonium chloride (DODAC), 1,2-dimyristoyloxypropyl-1,3-dimethylhydroxyethyl ammonium (DMRIE), and 2,3-dioleoyloxy-N-[2(spermine carboxamide)ethyl]-N,N-dimethyl-1-propanamium trifluoroacetate (DOSPA). Cationic lipids also include lipids with a tertiary amine group, including 1,2-dilinoleyloxy-N,N-dimethyl-3-aminopropane (DLinDMA). Cationic lipids are suitable for formulating RNA in lipid formulations as described herein, such as liposomes, emulsions and lipoplexes. Typically positive charges are contributed by at least one cationic lipid and negative charges are contributed by the RNA. In one embodiment, the pharmaceutical composition comprises at least one helper lipid, in addition to a cationic lipid. The helper lipid may be a neutral or an anionic lipid. The helper lipid may be a natural lipid, such as a phospholipid, or an analogue of a natural lipid, or a fully synthetic lipid, or lipid-like molecule, with no similarities with natural lipids. In the case where a pharmaceutical composition includes both a cationic lipid and a helper lipid, the molar ratio of the cationic lipid to the neutral lipid can be appropriately determined in view of stability of the formulation and the like.

In one embodiment, the pharmaceutical composition according to the present invention comprises protamine. According to the invention, protamine is useful as cationic carrier agent. The term "protamine" refers to any of various strongly basic proteins of relatively low molecular weight that are rich in arginine and are found associated especially with DNA in place of somatic histones in the sperm cells of animals such as fish. In particular, the term "protamine" refers to proteins found in fish sperm that are strongly basic, are soluble in water, are not coagulated by heat, and comprise multiple arginine monomers. According to the invention, the term "protamine" as used herein is meant to comprise any protamine amino acid sequence obtained or derived from native or biological sources including fragments thereof and multimeric forms of said amino acid sequence or fragment thereof. Furthermore, the term encompasses (synthesized) polypeptides which are artificial and specifically designed for specific purposes and cannot be isolated from native or biological sources.

The pharmaceutical composition according to the invention can be buffered, (e.g., with an acetate buffer, a citrate buffer, a succinate buffer, a Tris buffer, a phosphate buffer).

RNA-Containing Particles

In some embodiments, owing to the instability of non-protected RNA, it is advantageous to provide the RNA molecules of the present invention in complexed or encapsulated form. Respective pharmaceutical compositions are provided in the present invention. In particular, in some embodiments, the pharmaceutical composition of the present invention comprises nucleic acid-containing particles, preferably RNA-containing particles. Respective pharmaceutical compositions are referred to as particulate formulations. In particulate formulations according to the present invention, a particle comprises nucleic acid according to the invention and a pharmaceutically acceptable carrier or a pharmaceutically acceptable vehicle that is suitable for delivery of the nucleic acid. The nucleic acid-containing particles may be, for example, in the form of proteinaceous particles or in the form of lipid-containing particles. Suitable proteins or lipids are referred to as particle forming agents. Proteinaceous particles and lipid-containing particles have been described previously to be suitable for delivery of alphaviral RNA in particulate form (e.g. Strauss & Strauss, Microbiol. Rev., 1994, vol. 58, pp. 491-562). In particular, alphavirus structural proteins (provided e.g. by a helper virus) are a suitable carrier for delivery of RNA in the form of proteinaceous particles.

When the system according to the present invention is formulated as a particulate formulation, it is possible that each RNA species (e.g. replicon, replicase construct, and optional additional RNA species such as an RNA encoding a protein suitable for inhibiting IFN) is separately formulated as an individual particulate formulation. In that case, each individual particulate formulation will comprise one RNA species. The individual particulate formulations may be present as separate entities, e.g. in separate containers. Such formulations are obtainable by providing each RNA species separately (typically each in the form of an RNA-containing solution) together with a particle-forming agent, thereby allowing the formation of particles. Respective particles will contain exclusively the specific RNA species that is being provided when the particles are formed (individual particulate formulations).

In one embodiment, a pharmaceutical composition according to the invention comprises more than one individual particle formulation. Respective pharmaceutical compositions are referred to as mixed particulate formulations. Mixed particulate formulations according to the invention are obtainable by forming, separately, individual particulate formulations, as described above, followed by a step of mixing of the individual particulate formulations. By the step of mixing, one formulation comprising a mixed population of RNA-containing particles is obtainable (for illustration: e.g. a first population of particles may contain replicon according to the invention, and a second formulation of particles may contain replicase construct according to the invention). Individual particulate populations may be together in one container, comprising a mixed population of individual particulate formulations.

Alternatively, it is possible that all RNA species of the pharmaceutical composition (e.g. replicon, replicase construct, and optional additional species such as RNA encoding a protein suitable for inhibiting IFN) are formulated together as a combined particulate formulation. Such formulations are obtainable by providing a combined formulation (typically combined solution) of all RNA species together with a particle-forming agent, thereby allowing the formation of particles. As opposed to a mixed particulate formulation, a combined particulate formulation will typically comprise particles which comprise more than one RNA species. In a combined particulate composition different RNA species are typically present together in a single particle.

In one embodiment, the particulate formulation of the present invention is a nanoparticulate formulation. In that embodiment, the composition according to the present invention comprises nucleic acid according to the invention in the form of nanoparticles. Nanoparticulate formulations can be obtained by various protocols and with various complexing compounds. Lipids, polymers, oligomers, or amphipiles are typical constituents of nanoparticulate formulations.

As used herein, the term "nanoparticle" refers to any particle having a diameter making the particle suitable for systemic, in particular parenteral, administration, of, in particular, nucleic acids, typically a diameter of 1000 nanometers (nm) or less. In one embodiment, the nanoparticles have an average diameter in the range of from about 50 nm to about 1000 nm, preferably from about 50 nm to about 400 nm, preferably about 100 nm to about 300 nm such as about 150 nm to about 200 nm. In one embodiment, the nanoparticles have a diameter in the range of about 200 to about 700 nm, about 200 to about 600 nm, preferably about 250 to about 550 nm, in particular about 300 to about 500 nm or about 200 to about 400 nm.

In one embodiment, the polydispersity index (PI) of the nanoparticles described herein, as measured by dynamic light scattering, is 0.5 or less, preferably 0.4 or less or even more preferably 0.3 or less. The "polydispersity index" (PI) is a measurement of homogeneous or heterogeneous size distribution of the individual particles (such as liposomes) in a particle mixture and indicates the breadth of the particle distribution in a mixture. The PI can be determined, for example, as described in WO 2013/143555 A1.

As used herein, the term "nanoparticulate formulation" or similar terms refer to any particulate formulation that contains at least one nanoparticle. In some embodiments, a nanoparticulate composition is a uniform collection of nanoparticles. In some embodiments, a nanoparticulate composition is a lipid-containing pharmaceutical formulation, such as a liposome formulation or an emulsion.

Lipid-Containing Pharmaceutical Compositions

In one embodiment, the pharmaceutical composition of the present invention comprises at least one lipid. Preferably, at least one lipid is a cationic lipid. Said lipid-containing pharmaceutical composition comprises nucleic acid according to the present invention. In one embodiment, the pharmaceutical composition according to the invention comprises RNA encapsulated in a vesicle, e.g. in a liposome. In one embodiment, the pharmaceutical composition according to the invention comprises RNA in the form of an emulsion. In one embodiment, the pharmaceutical composition according to the invention comprises RNA in a complex with a cationic compound, thereby forming e.g. so-called lipoplexes or polyplexes. Encapsulation of RNA within vesicles such as liposomes is distinct from, for instance, lipid/RNA complexes. Lipid/RNA complexes are obtainable e.g. when RNA is e.g. mixed with pre-formed liposomes.

In one embodiment, the pharmaceutical composition according to the invention comprises RNA encapsulated in a vesicle. Such formulation is a particular particulate formulation according to the invention. A vesicle is a lipid bilayer rolled up into a spherical shell, enclosing a small space and separating that space from the space outside the vesicle. Typically, the space inside the vesicle is an aqueous space, i.e. comprises water. Typically, the space outside the vesicle is an aqueous space, i.e. comprises water. The lipid bilayer is formed by one or more lipids (vesicle-forming lipids). The membrane enclosing the vesicle is a lamellar phase, similar to that of the plasma membrane. The vesicle according to the present invention may be a multilamellar vesicle, a unilamellar vesicle, or a mixture thereof. When encapsulated in a vesicle, the RNA is typically separated from any external medium. Thus it is present in protected form, functionally equivalent to the protected form in a natural alphavirus. Suitable vesicles are particles, particularly nanoparticles, as described herein.

For example, RNA may be encapsulated in a liposome. In that embodiment, the pharmaceutical composition is or comprises a liposome formulation. Encapsulation within a liposome will typically protect RNA from RNase digestion. It is possible that the liposomes include some external RNA (e.g. on their surface), but at least half of the RNA (and ideally all of it) is encapsulated within the core of the liposome.

Liposomes are microscopic lipidic vesicles often having one or more bilayers of a vesicle-forming lipid, such as a phospholipid, and are capable of encapsulating a drug, e.g. RNA. Different types of liposomes may be employed in the context of the present invention, including, without being limited thereto, multilamellar vesicles (MLV), small unilamellar vesicles (SUV), large unilamellar vesicles (LUV), sterically stabilized liposomes (SSL), multivesicular vesicles (MV), and large multivesicular vesicles (LMV) as well as other bilayered forms known in the art. The size and lamellarity of the liposome will depend on the manner of preparation. There are several other forms of supramolecular organization in which lipids may be present in an aqueous medium, comprising lamellar phases, hexagonal and inverse hexagonal phases, cubic phases, micelles, reverse micelles composed of monolayers. These phases may also be obtained in the combination with DNA or RNA, and the interaction with RNA and DNA may substantially affect the phase state. Such phases may be present in nanoparticulate RNA formulations of the present invention.

Liposomes may be formed using standard methods known to the skilled person. Respective methods include the reverse evaporation method, the ethanol injection method, the dehydration-rehydration method, sonication or other suitable methods. Following liposome formation, the liposomes can be sized to obtain a population of liposomes having a substantially homogeneous size range.

In a preferred embodiment of the present invention, the RNA is present in a liposome which includes at least one cationic lipid. Respective liposomes can be formed from a single lipid or from a mixture of lipids, provided that at least one cationic lipid is used. Preferred cationic lipids have a nitrogen atom which is capable of being protonated; preferably, such cationic lipids are lipids with a tertiary amine group. A particularly suitable lipid with a tertiary amine group is 1,2-dilinoleyloxy-N,N-dimethyl-3-aminopropane (DLinDMA). In one embodiment, the RNA according to the present invention is present in a liposome formulation as described in WO 2012/006378 A1: a liposome having a lipid bilayer encapsulating an aqueous core including RNA, wherein the lipid bilayer comprises a lipid with a pKa in the range of 5.0 to 7.6, which preferably has a tertiary amine group. Preferred cationic lipids with a tertiary amine group include DLinDMA (pKa 5.8) and are generally described in WO 2012/031046 A2. According to WO 2012/031046 A2, liposomes comprising a respective compound are particularly suitable for encapsulation of RNA and thus liposomal delivery of RNA. In one embodiment, the RNA according to the present invention is present in a liposome formulation, wherein the liposome includes at least one cationic lipid whose head group includes at least one nitrogen atom (N) which is capable of being protonated, wherein the liposome and the RNA have a N:P ratio of between 1:1 and 20:1. According to the present invention, "N:P ratio" refers to the molar ratio of nitrogen atoms (N) in the cationic lipid to phosphate atoms (P) in the RNA comprised in a lipid containing particle (e.g. liposome), as described in WO 2013/006825 A1. The N:P ratio of between 1:1 and 20:1 is implicated in the net charge of the liposome and in efficiency of delivery of RNA to a vertebrate cell.

In one embodiment, the RNA according to the present invention is present in a liposome formulation that comprises at least one lipid which includes a polyethylene glycol (PEG) moiety, wherein RNA is encapsulated within a PEGylated liposome such that the PEG moiety is present on the liposome's exterior, as described in WO 2012/031043 A1 and WO 2013/033563 A1.

In one embodiment, the RNA according to the present invention is present in a liposome formulation, wherein the liposome has a diameter in the range of 60-180 nm, as described in WO 2012/030901 A1.

In one embodiment, the RNA according to the present invention is present in a liposome formulation, wherein the RNA-containing liposomes have a net charge close to zero or negative, as disclosed in WO 2013/143555 A1.

In other embodiments, the RNA according to the present invention is present in the form of an emulsion. Emulsions have been previously described to be used for delivery of nucleic acid molecules, such as RNA molecules, to cells. Preferred herein are oil-in-water emulsions. The respective emulsion particles comprise an oil core and a cationic lipid. More preferred are cationic oil-in-water emulsions in which the RNA according to the present invention is complexed to the emulsion particles. The emulsion particles comprise an oil core and a cationic lipid. The cationic lipid can interact with the negatively charged RNA, thereby anchoring the RNA to the emulsion particles. In an oil-in-water emulsion, emulsion particles are dispersed in an aqueous continuous phase. For example, the average diameter of the emulsion particles may typically be from about 80 nm to 180 nm. In one embodiment, the pharmaceutical composition of the present invention is a cationic oil-in-water emulsion, wherein the emulsion particles comprise an oil core and a cationic lipid, as described in WO 2012/006380 A2. The RNA according to the present invention may be present in the form of an emulsion comprising a cationic lipid wherein the N:P ratio of the emulsion is at least 4:1, as described in WO 2013/006834 A1. The RNA according to the present invention may be present in the form of a cationic lipid emulsion, as described in WO 2013/006837 A1. In particular, the composition may comprise RNA complexed with a particle of a cationic oil-in-water emulsion, wherein the ratio of oil/lipid is at least about 8:1 (mole:mole).

In other embodiments, the pharmaceutical composition according to the invention comprises RNA in the format of a lipoplex. The term, "lipoplex" or "RNA lipoplex" refers to a complex of lipids and nucleic acids such as RNA. Lipoplexes can be formed of cationic (positively charged) liposomes and the anionic (negatively charged) nucleic acid. The cationic liposomes can also include a neutral "helper" lipid. In the simplest case, the lipoplexes form spontaneously by mixing the nucleic acid with the liposomes with a certain mixing protocol, however various other protocols may be applied. It is understood that electrostatic interactions between positively charged liposomes and negatively charged nucleic acid are the driving force for the lipoplex formation (WO 2013/143555 A1). In one embodiment of the present invention, the net charge of the RNA lipoplex particles is close to zero or negative. It is known that electro-neutral or negatively charged lipoplexes of RNA and liposomes lead to substantial RNA expression in spleen dendritic cells (DCs) after systemic administration and are not associated with the elevated toxicity that has been reported for positively charged liposomes and lipoplexes (cf. WO 2013/143555 A1). Therefore, in one embodiment of the present invention, the pharmaceutical composition according to the invention comprises RNA in the format of nanoparticles, preferably lipoplex nanoparticles, in which (i) the number of positive charges in the nanoparticles does not exceed the number of negative charges in the nanoparticles and/or (ii) the nanoparticles have a neutral or net negative charge and/or (iii) the charge ratio of positive charges to negative charges in the nanoparticles is 1.4:1 or less and/or (iv) the zeta potential of the nanoparticles is 0 or less. As described in WO 2013/143555 A1, zeta potential is a scientific term for electrokinetic potential in colloidal systems. In the present invention, (a) the zeta potential and (b) the charge ratio of the cationic lipid to the RNA in the nanoparticles can both be calculated as disclosed in WO 2013/143555 A1. In summary, pharmaceutical compositions which are nanoparticulate lipoplex formulations with a defined particle size, wherein the net charge of the particles is close to zero or negative, as disclosed in WO 2013/143555 A1, are preferred pharmaceutical compositions in the context of the present invention.

Therapeutic Treatments

In view of the capacity to be administered to a subject, each of the RNA replicon according to the invention, the set according to the invention, the system according to the invention, the DNA according to the invention, the cells according to the invention, the kit according to the invention, or the pharmaceutical composition according to the invention, may be referred to as "medicament", or the like. The present invention foresees that the RNA replicon, the set, the system, the DNA, the cells, the kit, or the pharmaceutical composition of the present invention are provided for use as a medicament.

The medicament can be used to treat a subject. By "treat" is meant to administer a compound or composition or other entity as described herein to a subject. The term includes methods for treatment of the human or animal body by therapy.

The term "treatment" or "therapeutic treatment" preferably relates to any treatment which improves the health status and/or prolongs (increases) the lifespan of an individual. Said treatment may eliminate the disease in an individual, arrest or slow the development of a disease in an individual, inhibit or slow the development of a disease in an individual, decrease the frequency or severity of symptoms in an individual, and/or decrease the recurrence in an individual who currently has or who previously has had a disease.

The terms "prophylactic treatment" or "preventive treatment" relate to any treatment that is intended to prevent a disease from occurring in an individual. The terms "prophylactic treatment" or "preventive treatment" are used herein interchangeably.

In particular, cells, e.g., de-differentiated cells or differentiated cells described herein, are useful for cell transplantation and, in particular, in the treatment of a disease wherein the provision of these cells results in a prophylactic and/or therapeutic treatment of the disease.

Accordingly, the agents, compositions and methods described herein can be used to treat a subject with a disease, e.g., a disease characterized by the loss or degeneration of cells. The agents, compositions and methods described herein may also be used to prevent a disease described herein.

The term "disease" refers to an abnormal condition that affects the body of an individual. A disease is often construed as a medical condition associated with specific symptoms and signs. A disease may be caused by factors originally from an external source, such as infectious disease, or it may be caused by internal dysfunctions, such as autoimmune diseases. In humans, "disease" is often used more broadly to refer to any condition that causes pain, dysfunction, distress, social problems, or death to the individual afflicted, or similar problems for those in contact with the individual. In this broader sense, it sometimes includes injuries, disabilities, disorders, syndromes, infections, isolated symptoms, deviant behaviors, and atypical variations of structure and function, while in other contexts and for other purposes these may be considered distinguishable categories. Diseases usually affect individuals not only physically, but also emotionally, as contracting and living with many diseases can alter one's perspective on life, and one's personality.

The terms "individual" and "subject" are used herein interchangeably. They refer to human beings, non-human primates or other mammals (e.g. mouse, rat, rabbit, dog, cat, cattle, swine, sheep, horse or primate) that can be afflicted with or are susceptible to a disease or disorder (e.g., cancer) but may or may not have the disease or disorder. In many embodiments, the individual is a human being. Unless otherwise stated, the terms "individual" and "subject" do not denote a particular age, and thus encompass adults, elderlies, children, and newborns. In preferred embodiments of the present invention, the "individual" or "subject" is a "patient". The term "patient" means according to the invention a subject for treatment, in particular a diseased subject.

A prophylactic administration of an agent or composition of the invention, preferably protects the recipient from the development of a disease. A therapeutic administration of an agent or composition of the invention, may lead to the inhibition of the progression of the disease. This comprises the deceleration of the progression of the disease, in particular a disruption of the progression of the disease, which preferably leads to elimination of the disease.

The agents and compositions described herein may be administered via any conventional route, such as by parenteral administration including by injection or infusion.

Administration is preferably parenterally, e.g. intravenously, intraarterially, subcutaneously, intradermally or intramuscularly.

Compositions suitable for parenteral administration usually comprise a sterile aqueous or nonaqueous preparation of the active compound, which is preferably isotonic to the blood of the recipient. Examples of compatible carriers and solvents are Ringer solution and isotonic sodium chloride solution. In addition, usually sterile, fixed oils are used as solution or suspension medium.

The agents and compositions described herein are administered in effective amounts. An "effective amount" refers to the amount which achieves a desired reaction or a desired effect alone or together with further doses. In the case of treatment of a particular disease or of a particular condition, the desired reaction preferably relates to inhibition of the course of the disease. This comprises slowing down the progress of the disease and, in particular, interrupting or reversing the progress of the disease. The desired reaction in a treatment of a disease or of a condition may also be delay of the onset or a prevention of the onset of said disease or said condition.

An effective amount of an agent or composition described herein will depend on the condition to be treated, the severeness of the disease, the individual parameters of the patient, including age, physiological condition, size and weight, the duration of treatment, the type of an accompanying therapy (if present), the specific route of administration and similar factors. Accordingly, the doses administered of the agents described herein may depend on various of such parameters. In the case that a reaction in a patient is insufficient with an initial dose, higher doses (or effectively higher doses achieved by a different, more localized route of administration) may be used.

The agents and compositions described herein can be administered to patients, e.g., in vivo, to treat or prevent a variety of disorders such as those described herein.

Preferred patients include human patients having disorders that can be corrected or ameliorated by administering the agents and compositions described herein.

The pharmaceutical composition can be administered locally or systemically, preferably systemically.

The term "systemic administration" refers to the administration of an agent such that the agent becomes widely distributed in the body of an individual in significant amounts and develops a desired effect. For example, the agent may develop its desired effect in the blood and/or reaches its desired site of action via the vascular system. Typical systemic routes of administration include administration by introducing the agent directly into the vascular system or oral, pulmonary, or intramuscular administration wherein the agent is adsorbed, enters the vascular system, and is carried to one or more desired site(s) of action via the blood.

According to the present invention, it is preferred that the systemic administration is by parenteral administration. The term "parenteral administration" refers to administration of an agent such that the agent does not pass the intestine. The term "parenteral administration" includes intravenous administration, subcutaneous administration, intradermal administration or intraarterial administration but is not limited thereto.

Administration may also be carried out, for example, orally, intraperitoneally or intramuscularly.

The agents and compositions provided herein may be used alone or in combination with conventional therapeutic regimens.

EXAMPLES

Examples

Material and Methods:
DNA Encoding Replicon and Trans-Replicon Constructs:

Vectors systems used herein were engineered from Venezuelan Equine Encephalitis virus (VEEV; accession no. L01442), the overall vector design resembles a Semliki Forest virus vector system generated before (FIG. 1). In a first step, a plasmid encoding a self-replicating RNA (cis-replicon) based on VEEV was obtained by gene synthesis from a commercial provider. This construct lacks VEEV structural genes, but contains all conserved sequence elements (CSE) of VEEV that serve as replication-recognition sequence (RRS) and control viral replication into pST1 plasmid backbone (Holtkamp et al., 2006, Blood, vol. 108, pp. 4009-4017) under the transcriptional control of a T7 phage RNA-polymerase promoter. A plasmid-encoded poly (A) cassette consisting of 30 and 70 adenylate residues (polyA30-70), separated by a 10 nucleotide random sequence (WO 2016/005004 A1), was added immediately downstream of the very last nucleotide of the VEEV 3'CSE. A SapI restriction site for plasmid linearization was placed immediately downstream of the poly(A) cassette. Using further gene synthesis and PCR-based seamless cloning/recombination techniques we generated a plasmid serving as template for in vitro transcription of an mRNA encoding the complete open reading frame of the VEEV replicase into the pST1 plasmid backbone (Holtkamp et al., 2006, Blood, vol. 108, pp. 4009-4017). This vector contains the human alpha-globin 5'UTR upstream, and a plasmid-encoded poly(A30-70) cassette downstream of the replicase ORF. Again a SapI restriction site was placed immediately downstream of the poly(A) cassette for plasmid linearization. Upon in vitro transcription the resulting mRNA lacks functional RRS of VEEV and is unable to replicate. For in vitro transcription of RNA replicating in trans (trans-replicon) two different variants of template plasmids were generated. For the first variant a plasmid encoding a trans-replicon with WT-RRSs (non-modified 5' CSE, subgenomic promoter, 3'CSE) was obtained by removing the majority of VEEV-replicase coding sequences from the cis-replicon, keeping only those comprising functional RRSs (5'-CSE and the subgenomic promoter). Owing to the removal of the major part of the replicase ORF, the RNA encoded by the respective plasmid, when present in a host cell, is not capable to drive replication in cis, but requires for replication the presence of functional alphavirus non-structural protein in trans. Genes of interests are inserted downstream of the subgenomic promoter.

For the second trans-replicon version, the sequences comprising the subgenomic promoter were removed, and the 5'RRS was shortened to the first ~270 nts of the VEEV genome. Furthermore, the 5'RRS was mutated to remove any AUG codon that could serve as translation start codon. Compensation nucleotide changes were introduced to ensure proper folding and function of the 5'RRS, this trans-replicon was Δ5ATG-RRSΔSGP. The removal of 5'AUG ensures that translation starts exclusively with the start codon of the ORF of interest, which is inserted downstream of the mutated 5'CSE.

The major biological difference between both variant of trans-replicating RNA is that trans-replicons with WT-RRS and subgenomic promoter encode transgenes on the subgenomic transcript which is generated only upon replication. This means that no protein of interest is translated in absence of a replicase expressed in trans. In contrast, the Δ5ATG- RRSΔSGP trans-replicon can be translated to proteins even without replicase provided that in vitro transcriptions were performed with synthetic cap analogs.

Genes of interest herein are six reprogramming transcription factors (rTF) promoting pluripotency (OCT4, SOX2, MYC, KLF4, NANOG, LIN28) and three interferon escape proteins of Vaccinia virus (E3, K3 and B18).

Example 1: RNA-Reprogramming Using Trans-Replicon Technology (WT-RRS)

Figure 2:
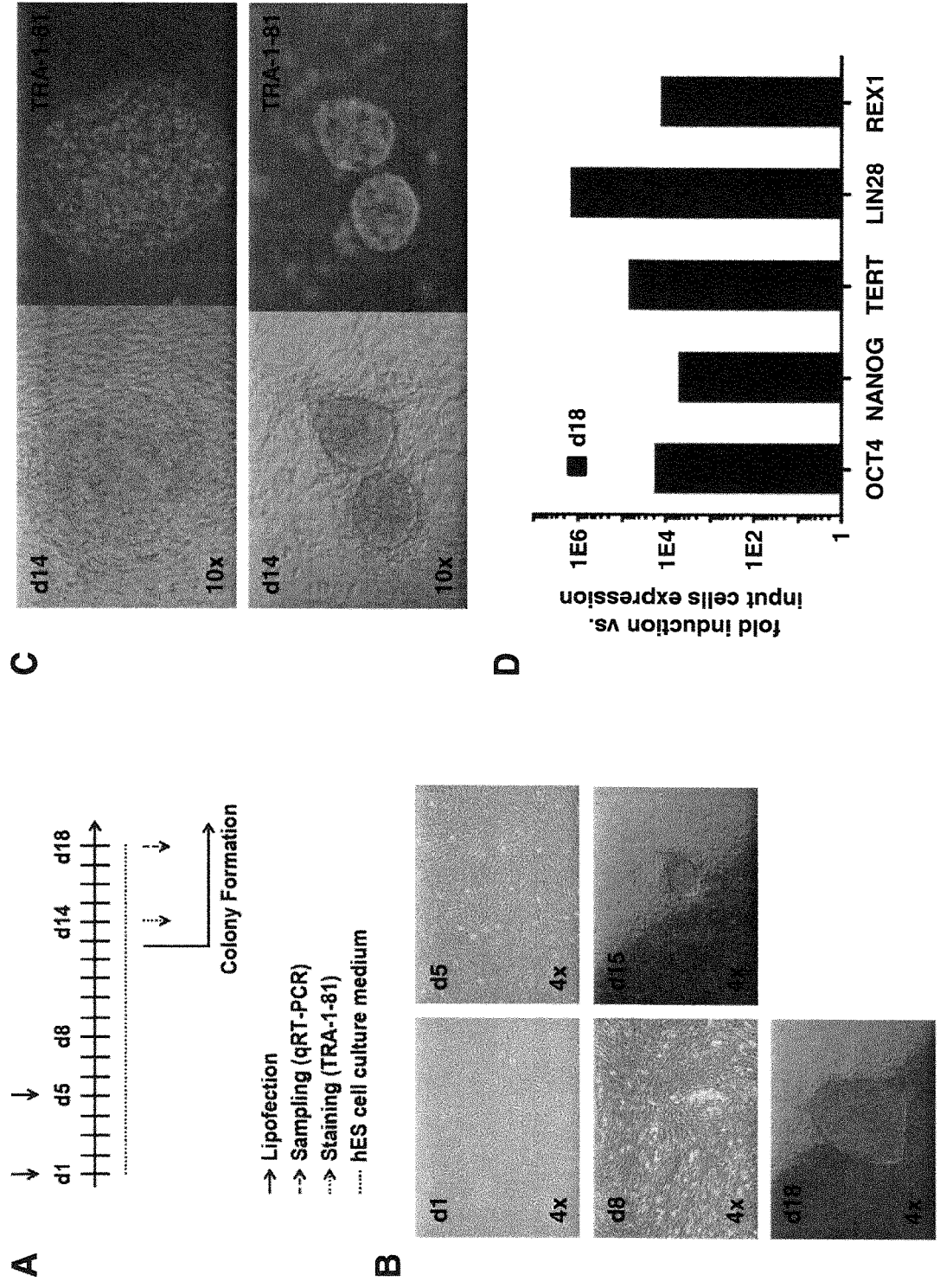
FIG. 2: RNA-Reprogramming using trans-Replicon Technology (WT-RRS)

Primary human dermal fibroblasts (HDFs, Innoprot) were plated into 6-wells (100,000 cells/well) and lipofected after 4h using per 6-well 6 µl RNAiMAX (Invitrogen) and 0.7 µg non-modified synthetic TR-WT-RRS mRNA mixture together with 0.7 µg Replicase mRNA and 0.4 µg of a miRNA mixture composed of miRNAs 302a-d and 367 (1:1:1:1:1:1). The TR-WT-RRS mRNA mixture was thereby composed of 0.4 µg synthetic mRNA encoding the reprogramming TF OSKMNL (1:1:1:1:1:1) together with 0.1 µg of each EKB. After 96h (day 5) cells were lipofected a second time using 1.7 µl RNAiMAX and 0.4 µg Replicase mRNA. Cells were cultivated in human embryonic stem (hES) cell medium (NutriStem media, Stemgent) supplemented with 10 ng/ml bFGF (Invitrogen) and 0.5 µM Thiazovivin (Stemgent) and all lipofections were performed according to the manufacturer's instructions. Colony formation was observed from d12 on and timeline of the experimental procedure is depictured (FIG. 2A). FIG. 2B shows a microscopy analysis of colony formation from d1 to d18. Colony morphology and growth behavior of resulting iPS-cell colonies using TR-WT-RRS mRNAs was hES cell-like with tightly packed small cells in distinct colonies and well-defined borders. The colonies could be stained positive for the hES cell surface marker TRA-1-81 (grey/green). TRA-1-81 live staining was performed with the Stain-Alive TRA-1-81 antibody (Stemgent) according to the manufacturer's instructions. Representative pictures of colonies are shown in FIG. 2C. To further assess pluripotency of colonies, cells were pelleted on d18, total RNA isolated and mRNA-expression of the hES-markers OCT4 (endogenous), NANOG (endogenous), LIN28 (endogenous), TERT and REX1 was quantified by qRT-PCR. mRNA expression was normalized to that of HPRT and is shown in FIG. 2D as fold induction compared to the transcript levels of input cells. All analyzed markers were highly expressed compared to input cells indicating pluripotency of reprogrammed cells.

The data shows that the TR-WT-RRS technology can be used for the RNA-based generation of iPS cells. Successful reprogramming of cells was confirmed by hES-cell like morphology and growth behavior and the expression of hES-cell surface and endogenous markers of resulting iPS-cell colonies.

Example 2: RNA-Reprogramming Using Trans-Replicon Technology (Δ5ATG-RRSΔSGP)

Figure 3:
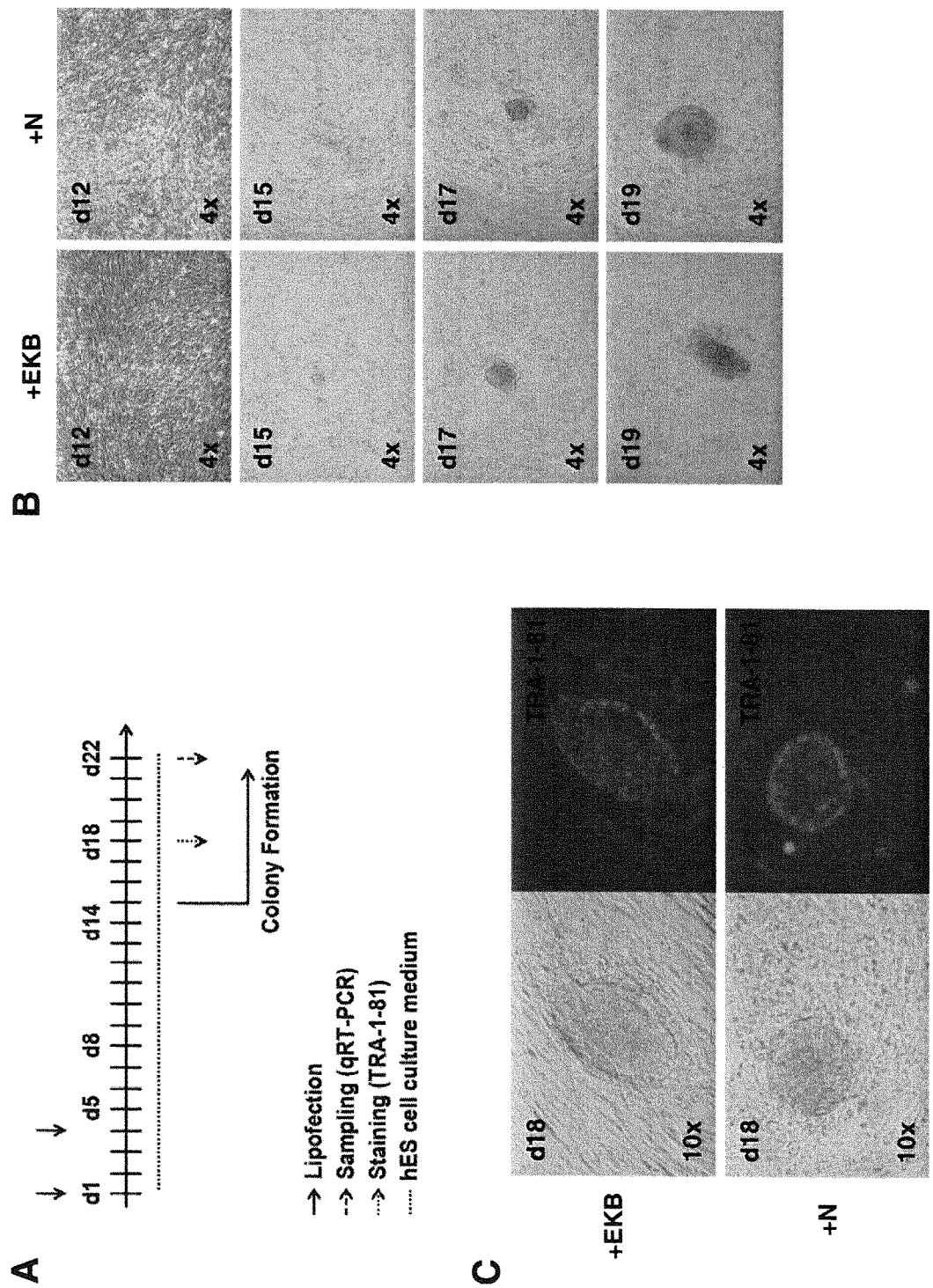
FIG. 3: RNA-Reprogramming using trans-Replicon Technology (Δ5ATG-RRSΔSGP)
Figure 3:
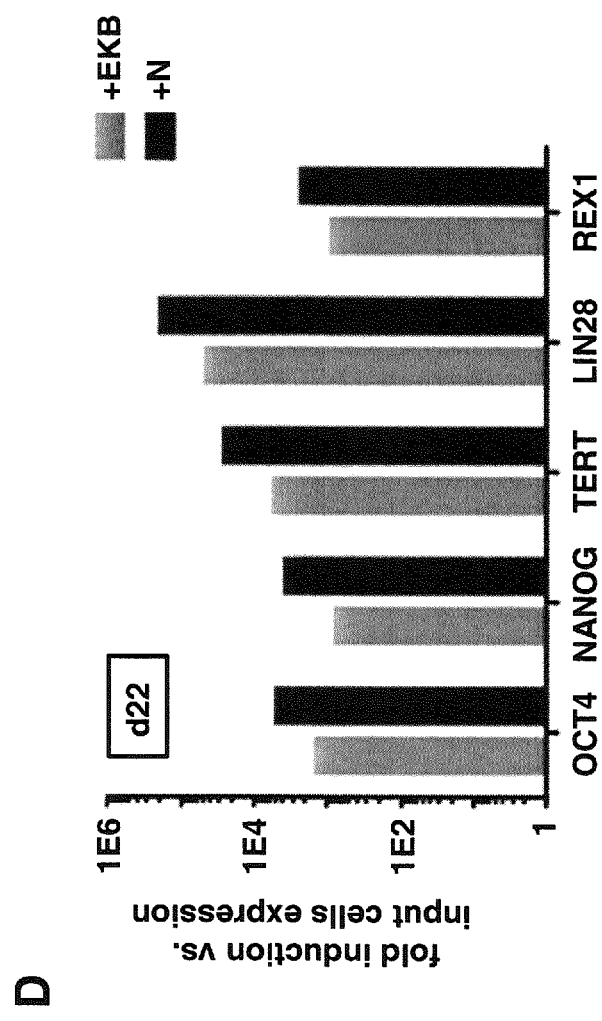

FIG. 3A shows the timeline for the reprogramming of primary human dermal fibroblasts (HDFs, Innoprot). 40,000 cells were plated into a 12-well-plate and lipofected 4h thereafter using per 12-well 2.5 µl RNAiMAX (Invitrogen) and mRNA mixtures that were composed either of 0.33 µg non-modified synthetic TR-Δ5ATG-RRSΔSGP mRNA encoding the reprogramming TF OSKMNL (1:1:1:1:1:1) together with 0.02 µg synthetic mRNA of each EKB (+"EKB") or 0.25 µg non-modified synthetic TR-Δ5ATG-RRSΔSGP mRNA encoding OSKMNL (1:1:1:1:1:1) together with 0.04 µg synthetic mRNA of N ("+N") alone (the viral escape protein NSs (N) from Toscana virus is a potent inhibitor of IFN-response and can be used to substitute EKB for successful RNA-based reprogramming). Both mixtures were combined with 0.3 µg Replicase mRNA and 0.17 µg of a miRNA mixture composed of miRNAs 302a-d and 367 (1:1:1:1:1:1). After 72h (day 4) cells were lipofected a second time using the exact procedures and mixtures as on d1. Cells were cultivated throughout the experiment in human embryonic stem (hES) cell medium (NutriStem media, Stemgent) supplemented with 10 ng/ml bFGF (Invitrogen) and 0.5 µM Thiazovivin (Stemgent) and all lipofections were performed according to the manufacturers instructions. As indicated colony formation could be observed from d15 on. FIG. 3B shows a microscopy analysis of colony formation from d12 on. Colony morphology and growth behavior of resulting iPS-cell colonies using TR-Δ5ATG-RRSΔSGP mRNAs and either EKB mRNA or N mRNA was hES cell-like with tightly packed small cells in distinct colonies and well-defined borders. The colonies could be stained positive for the hES cell surface marker TRA-1-81 (grey/green). TRA-1-81 live staining was performed with the Stain-Alive TRA-1-81 antibody (Stemgent) according to the manufacturers instructions. Representative pictures of colonies are shown in FIG. 3C. To further assess pluripotency of colonies, cells were pelleted on d22, total RNA isolated and mRNA-expression of the hES-markers OCT4 (endogenous), NANOG (endogenous), LIN28 (endogenous), TERT and REX1 was quantified by qRT-PCR. mRNA expression was normalized to that of HPRT and is shown in FIG. 3D as fold induction compared to the transcript levels of input cells. All analyzed markers were highly expressed in resulting iPS-cell colonies using TR-Δ5ATG-RRSΔSGP mRNAs and either EKB mRNA or N mRNA compared to input cells indicating pluripotency of reprogrammed cells.

The data shows that the TR technology (Δ5ATG-RRSΔSGP) can be used for the RNA-based generation of iPS cells. Thereby IFN-response to non-modified synthetic RNA can be blocked by using EKB or N mRNA leading to the formation of iPS colonies. Successful reprogramming of cells was confirmed by hES-cell like morphology and growth behavior and the expression of hES-cell surface and endogenous markers of resulting iPS-cell colonies.

Example 3: RNA-Based Reprogramming by One Transfection Using Trans-Replicon Technology (WT-RSS)

Figure 4:
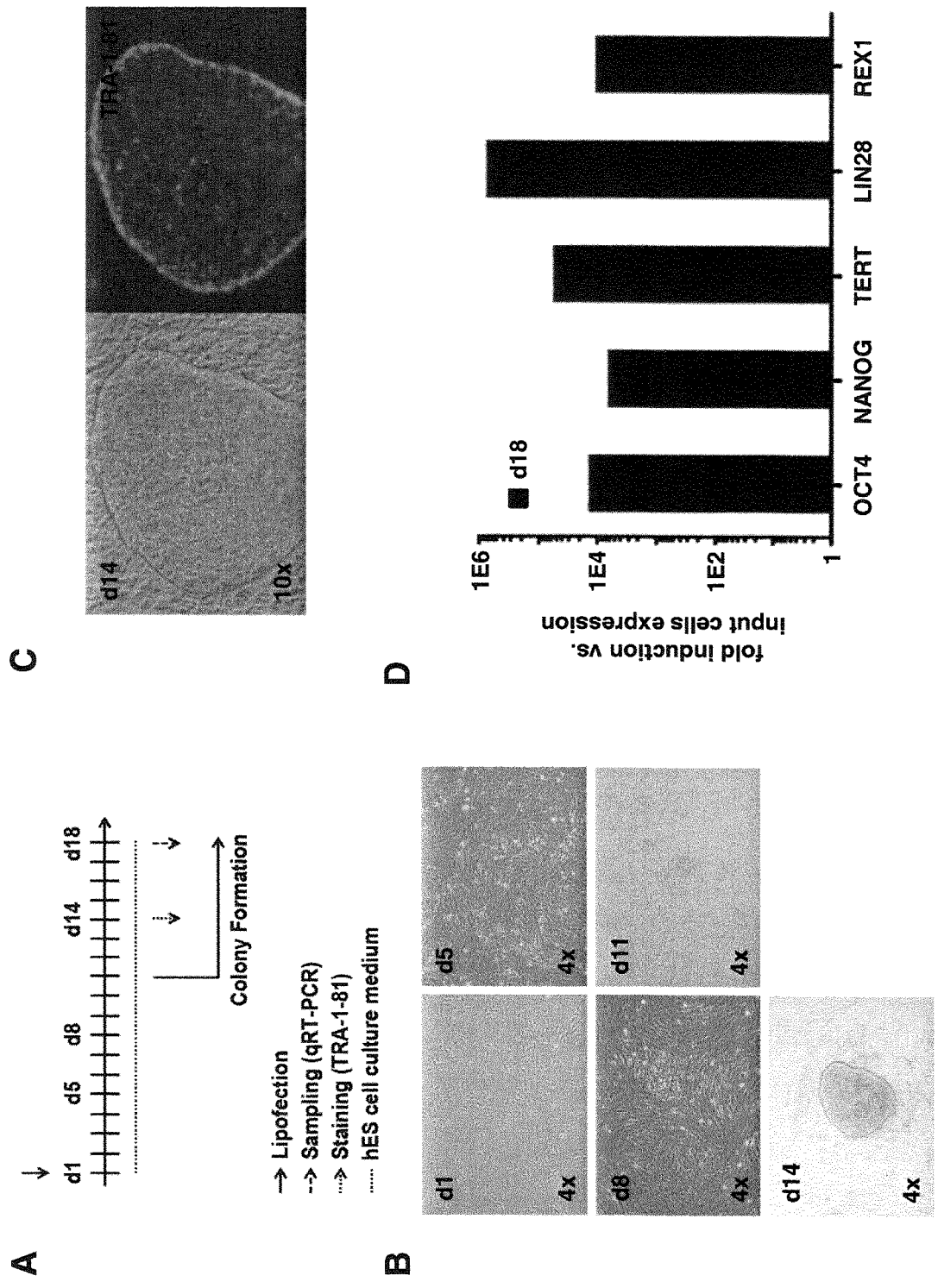
FIG. 4: RNA-based Reprogramming by one transfection using trans-Replicon Technology (WT-RSS)

Primary human dermal fibroblasts (HDFs, Innoprot) were plated into 6-wells (100,000 cells/well) and lipofected after 4h using per 6-well 6 µl RNAiMAX (Invitrogen) and 0.7 µg non-modified synthetic TR-WT-RRS mRNA mixture together with 0.7 µg Replicase mRNA and 0.4 µg of a miRNA mixture composed of miRNAs 302a-d and 367 (1:1:1:1:1:1). The TR-WT-RRS mRNA mixture was thereby composed of 0.4 µg synthetic mRNA encoding the reprogramming TF OSKMNL (1:1:1:1:1:1) together with 0.1 µg of each EKB. Cells were cultivated in human embryonic stem (hES) cell medium (NutriStem media, Stemgent) supplemented with 10 ng/ml bFGF (Invitrogen) and 0.5 µM Thiazovivin (Stemgent) and all lipofections were performed according to the manufacturers instructions. Colony formation was observed from d11 on and timeline of the experimental procedure is depictured (FIG. 4A). FIG. 4B shows a microscopy analysis of colony formation from d1 to d14. Colony morphology and growth behavior of resulting iPS-cell colonies using TR-WT-RRS mRNAs was hES cell-like with tightly packed small cells in distinct colonies and well-defined borders. The colonies could be stained positive for the hES cell surface marker TRA-1-81 (grey/green). TRA-1-81 live staining was performed with the Stain-Alive TRA-1-81 antibody (Stemgent) according to the manufacturers instructions. Representative pictures of colonies are shown in FIG. 4C. To further assess pluripotency of colonies, cells were pelleted on d18, total RNA isolated and mRNA-expression of the hES-markers OCT4 (endogenous), NANOG (endogenous), LIN28 (endogenous), TERT and REX1 was quantified by qRT-PCR. mRNA expression was normalized to that of HPRT and is shown in FIG. 4D as fold induction compared to the transcript levels of input cells. All analyzed markers were highly expressed compared to input cells indicating pluripotency of reprogrammed cells.

The data shows that the TR technology (WT-RRS) can even be used for the RNA-based generation of iPS cells with only a single transfection. Successful reprogramming of cells was confirmed by hES-cell like morphology and growth behavior and the expression of hES-cell surface and endogenous markers of resulting iPS-cell colonies.

The invention claimed is:

1. A system comprising:
   (i) an RNA construct for expressing a functional alphavirus non-structural protein, and
   (ii) an RNA replicon comprising an open reading frame encoding a reprogramming factor and a 5' replication recognition sequence, wherein the 5' replication recognition sequence can be recognized by an alphaviral replicase in trans and is characterized in that it does not contain any initiation codons, wherein the 5' replication recognition sequence does not overlap with a first open reading frame of the RNA replicon, and the initiation codon of the first open reading frame is in the 5'→3' direction of the RNA replicon and is the first functional initiation codon; wherein
   the RNA construct is an mRNA molecule comprising a 5'-cap; and
   the RNA replicon does not comprise an open reading frame encoding a functional alphavirus non-structural protein.

2. The system according to claim 1, wherein the RNA replicon comprises at least one further open reading frame encoding a different reprogramming factor.

3. The system according to claim 1, wherein the reprogramming factor is selected from the group consisting of OCT4, SOX2, KLF4, c-MYC, LIN28 and NANOG.

4. A method of producing cells having stem cell characteristics comprising the step of introducing into somatic cells a system comprising one or more RNA replicons according to claim 1.

5. The method according to claim 4, wherein the one or more RNA replicons encode a set of reprogramming factors.

6. The method according to claim 4, wherein each of the one or more RNA replicons comprises one open reading frame encoding a reprogramming factor.

7. The method according to claim 4, wherein the one or more RNA replicons comprise a set of RNA replicons, wherein each of the RNA replicons comprises at least one open reading frame encoding a reprogramming factor and the set of RNA replicons encodes a set of reprogramming factors.

8. A method for providing differentiated cell types comprising the steps of (i) providing cells having stem cell characteristics using the method of claim 4, and (ii) culturing the cells having stem cell characteristics under conditions that induce or direct partial or complete differentiation to a differentiated cell type.

9. The system according to claim 1, wherein the RNA replicon further comprises a subgenomic promoter.

10. A system comprising:
    (i) an RNA construct for expressing a functional alphavirus non-structural protein, and
    (ii) a set of RNA replicons, wherein each of the RNA replicons comprises at least one open reading frame encoding a reprogramming factor and a 5' replication recognition sequence, wherein the 5' replication recognition sequence can be recognized by an alphaviral replicase in trans and is characterized in that it does not contain any initiation codons, wherein the 5' replication recognition sequence does not overlap with a first open reading frame of the RNA replicon, and the initiation codon of the first open reading frame is in the 5'→3' direction of the RNA replicon and is the first functional initiation codon, and the set of RNA replicons encodes a set of reprogramming factors; wherein
    the RNA construct is an mRNA molecule comprising a 5'-cap; and
    the RNA replicons do not comprise an open reading frame encoding a functional alphavirus non-structural protein.

11. The system according to claim 10, wherein each of the RNA replicons comprises one open reading frame encoding a reprogramming factor.

12. The system according to claim 10, wherein the set of reprogramming factors comprises OCT4 and SOX2.

13. The system according to claim 12, wherein the set of reprogramming factors further comprises KLF4 and/or c-MYC.

14. The system according to claim 10, wherein the set of reprogramming factors comprises OCT4, SOX2, NANOG and LIN28.

15. The system according to claim 10, wherein at least one of the RNA replicons in the set of RNA replicons further comprises a subgenomic promoter.

16. A method for providing cells having stem cell characteristics comprising the steps of:
    (i) providing a cell population comprising somatic cells,
    (ii) providing an RNA construct for expressing a functional alphavirus non-structural protein, wherein the RNA construct is an mRNA molecule comprising a 5'-cap,
    (iii) providing one or more RNA replicons, wherein each of the one or more RNA replicons can be replicated by the functional alphavirus non-structural protein in trans and comprises at least one open reading frame encoding a reprogramming factor and a 5' replication recognition sequence, wherein the 5' replication recognition sequence can be recognized by an alphaviral replicase in trans and is characterized in that it does not contain any initiation codons, wherein the 5' replication recognition sequence does not overlap with a first open reading frame of the one or more RNA replicons, and the initiation codon of the first open reading frame is in the 5'→3' direction of the one or more RNA replicons and is the first functional initiation codon, wherein the one or more RNA replicons do not comprise an open reading frame encoding a functional alphavirus non-structural protein,
    (iv) introducing the RNA construct and the one or more RNA replicons into the somatic cells, such that the cells express a set of reprogramming factors useful in reprogramming somatic cells to cells having stem cell characteristics, and
(v) allowing the development of cells having stem cell characteristics.

17. The method according to claim 16, wherein at least one of the one or more RNA replicons further comprises a subgenomic promoter.

18. Cells comprising
(i) an RNA construct for expressing a functional alphavirus non-structural protein, and
(ii) an RNA replicon comprising an open reading frame encoding a reprogramming factor and a 5' replication recognition sequence, wherein the 5' replication recognition sequence can be recognized by an alphaviral replicase in trans and is characterized in that it does not contain any initiation codons, wherein the 5' replication recognition sequence does not overlap with a first open reading frame of the RNA replicon, and the initiation codon of the first open reading frame is in the 5'→3' direction of the RNA replicon and is the first functional initiation codon; wherein
the RNA construct is an mRNA molecule comprising a 5'-cap; and
the RNA replicon does not comprise an open reading frame encoding a functional alphavirus non-structural protein.

19. The cells according to claim 18, wherein the RNA replicon further comprises a subgenomic promoter.

* * * * *